United States Patent
Flynn et al.

(10) Patent No.: US 9,334,267 B2
(45) Date of Patent: *May 10, 2016

(54) RAF INHIBITOR COMPOUNDS

(71) Applicants: Deciphera Pharmaceuticals, LLC, Lawrence, KS (US); Eli Lilly and Company, Indianapolis, IN (US)

(72) Inventors: Daniel L. Flynn, Lawrence, KS (US); Michael D. Kaufman, Lawrence, KS (US); Lakshminarayana Vogeti, Lawrence, KS (US); Scott Wise, Lawrence, KS (US); Wei-Ping Lu, Lawrence, KS (US); Bryan Smith, Lawrence, KS (US); James R. Henry, Indianapolis, IN (US); Philip A. Hipskind, Indianapolis, IN (US); Sheng-Bin Peng, Indianapolis, IN (US)

(73) Assignee: Deciphera Pharmaceuticals, LLC, Lawrence, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/383,799

(22) PCT Filed: Mar. 5, 2013

(86) PCT No.: PCT/US2013/029098
§ 371 (c)(1),
(2) Date: Sep. 8, 2014

(87) PCT Pub. No.: WO2013/134252
PCT Pub. Date: Sep. 12, 2013

(65) Prior Publication Data
US 2015/0119392 A1    Apr. 30, 2015

Related U.S. Application Data
(60) Provisional application No. 61/607,702, filed on Mar. 7, 2012.

(51) Int. Cl.
*C07D 471/12* (2006.01)
*C07D 471/04* (2006.01)

(52) U.S. Cl.
CPC ............ *C07D 471/04* (2013.01); *C07D 471/12* (2013.01)

(58) Field of Classification Search
CPC ........................... C07D 471/12; C07D 471/04
See application file for complete search history.

(56) References Cited

U.S. PATENT DOCUMENTS 8,741,911 B2 * 6/2014 Allgeier et al. .......... 514/264.11

FOREIGN PATENT DOCUMENTS

WO    WO2008/034008    3/2008
WO    WO2011/100319    8/2011

OTHER PUBLICATIONS

Swords et al., 2015, http://www.nature.com/leu/journal/v26/n10/full/leu2012114a.html.*
Brilli et al., 2015, http://www.medscape.com/viewarticle/742987_2.*
Posadas et al., 2015, http://onlinelibrary.wiley.com/doi/10.1002/cncr.22757/full.*
Lang et al., 2005, caplus an 2005:1103581.*
Bhagwat et al., 2000, caplus an 2000:277982.*
Berge, et al., "Pharmaceutical Salts" Journal of Pharmaceutical Sciences, vol. 66, No. 1, Jan. 1977.
Davies et al, "Mutations of the BRAF Gene in Human Cancer" Nature, 2002, 417: 949-954.
Fukui et al., "Molecular Cloning and Characterization of an Activated Human c-*raf*-1 Gene", Molecular and Cellular Biology, May 1987, vol. 7, No. 5, p. 1776-1781.
Hatzivassiliou G, et al. "RAF Inhibitors Prime Wild-Type RAF to Activate the MAPK Pathway and Enhance Growth" Nature, 2010, 464: 431-435.
Heidorn, et al, "Kinase-Dead BRAF and Oncogenic RAS Cooperative to Drive Tumor Progression Through CRAF" Cell, 2010, 140: 209-221.
Johannessen et al, "COT/MAP3K8 Drives Resistance to RAF Inhibition Through Map Kinase Pathway Reactivation" Nature. 2010, 468: 968-72.
Lennartsson et al, "The Stem Cell Factor Receptor/C-Kit as a Drug Target in Cancer" Current Cancer Drug Targets, 2006, 6: 65.
Montagut et al, "Elevated CRAF as a Potential Mechanism of Acquired Resistance to BRAF Inhibition in Melanoma" Cancer Res. 2008, 68: 4853-61.
Moss, G.P. "Basic Terminology of Stereochemistry" Pure Appl. Chem. 1996, 68, pp. 2193-2222.
Muller, P. "Glossary of Terms Used in Physical Organic Chemistry" Pure Appl. Chem. 1994, 66, pp. 1077-1184.
Nazarian et al, "Melanomas Acquire Resistance to B-RAF (V600e) Inhibition by RTK or N-RAS Upregulation" Nature. 2010, 468: 973-7.

(Continued)

*Primary Examiner* — Sun Jae Yoo
(74) *Attorney, Agent, or Firm* — Cooley LLP

(57) ABSTRACT

This invention provides compounds of Formula I: (Formula I should be inserted here) or a pharmaceutically acceptable salt thereof; pharmaceutical compositions comprising a compound of Formula I; and use of a compound of Formula I for treating specified cancers.

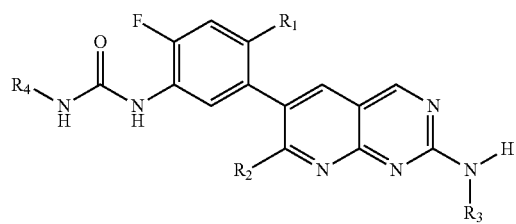

Formula I

17 Claims, No Drawings

(56) References Cited

OTHER PUBLICATIONS

Palmer, et al., "Structure-Activity Relationships for 2-Anilino-6-Phenylpyrido[2,3-d]Pyrimidin-7(8H)-Ones as Inhibitors of the Cellular Checkpoint Kinase WEE1", Bioorganic & Medicinal Chemistry Letters, 15 (2005) 1931-1935.

Poulikakos et al, "RAF Inhibitors Transactivate RAF Dimers and ERK Signalling in Cells With Wild-Type BRAF" Nature, 2010, 464: 427-430.

Poulikakos et al, RAF Inhibitor Resistance Is Mediated by Dimerization of Aberrantly Spliced BRAF (V600E) Nature, 2011, 480: 387-390.

Pylayeva-Gupta et al, "RAS Oncogenes: Waving a Tumorigenic Web" Nature Reviews Cancer, 2011, 11: 761.

Rominger, et al, "An Intrinsic Atpase Activity of Phospho-MEK-1 Uncoupled From Downstream ERK Phosphorylation" Arch. Biochem. Biophys. 2007, 464: 130-137.

Schindler et al, "Structural Mechanism for STI-571 Inhibition of Abelson Tyrosine Kinase" Science, 2000, 289: 1938-1942.

Schubbert et al, "Hyperactive RAS in Developmental Disorders and Cancer" Nature Reviews Cancer, 2007, 7: 295.

Sebolt-Leopold et al, "Targeting the Mitogen Activated Protein Kinase Casecade to Treat Cancer" Nat Rev Cancer, 2004, 4: 937-947.

International Search Report from corresponding PCT application No. PCT/US2013/029098, dated Jun. 24, 2013.

Shi et al, "Combinatorial Treatments That Overcome PDGFRβ-Driven Resistance of Melanoma Cells to $^{V600E}$ B-RAF Inhibition" Cancer Res. 2011, 71: 5067-74.

Smith et al., "Single-Step Purification of Polypeptides Expressed in *Escherichia coli* as Fusions With Glutathione S-Transferase", Gene, 67 (1988) 31-40.

Smith, D., "Purification of Glutathione S-Transferase Fusion Proteins", Methods in Molecular and Cellular Biology, 4:220-229 (1993).

Su et al, "RAS Mutations in Cutaneous Squamous-Cell Carcinomas in Patients Treated With BRAF Inhibitors" New England Journal of Medicine. 2012 366: 207-215.

Tsai et al., "Discovery of a Selective Inhibitor of Oncogenic B-RAF Kinase With Potent Antimelanoma Activity", PNAS, Feb. 26, 2008, vol. 105., No. 8, p. 3041-3046.

Villanueva et al, "Acquired Resistance to BRAF Inhibitors Mediated by a RAF Kinase Switch in Melanoma Can be Overcome by Cotargeting MEDK and IGF-1R/P13K" Cancer Cell. 2010, 18: 683-95.

Wagle, et al., "Dissecting Therapeutic Resistance to RAF Inhibition in Melanoma by Tumor Genomic Profiling" Journal of Clinical Onology, vol. 29, No. 22, p. 3085-3096, Aug. 1, 2011.

Wan et al, "Mechanism of Activation of the RAF-ERK Signaling Pathway by Onvogenic Mutations of B-RAF" Cell, 2004, 116: 855-867.

Wellbrock et al, "The RAF Proteins Take Centre Stage" Nat Rev Mol Cell Biol, 2004, 5: 875-885.

Whittaker et al, "Gatekeeper Mutations Mediate Resistance to BRAF-Targeted Therapies" Sci Transl Med. 2010, 2: 35-41.

Zheng et al., Cloning and Characterization of Two Distinct Human Extracellular Single-Regulated Kinase Activator Kinases, MEK1 and MEK2, The Journal of Biological Chemistry, vol. 268, No. 15, May 25, 1993, p. 11435-11439.

\* cited by examiner

RAF INHIBITOR COMPOUNDS

The Ras/Raf/mitogen-activated protein kinase kinase (also known as MAP2K; MAPK kinase; and MAPK/ERK kinase or MEK)/extracellular signal-regulated kinase (ERK) signaling cascade (referred to herein as "Ras/Raf/MEK/ERK" or "Ras/Raf/MEK/MAPK") is an evolutionary conserved pathway that plays an integral role in development and tissue homeostasis in mammals. This signaling pathway consists of a kinase cascade that relays extracellular signals to the nucleus to regulate gene expression and key cellular functions. Gene expression controlled by the Ras/Raf/MEK/ERK signaling pathway regulates fundamental cellular processes including proliferation, differentiation, apoptosis, and angiogenesis. These diverse roles of Ras/Raf/MEK/ERK signaling are aberrantly activated in various types of cancer. Mutations in genes within this pathway may lead to constitutively active proteins resulting in increased cell proliferation, and resistance to apoptosis.

Raf (a serine/threonine-protein kinase) is encoded by a gene family consisting of three genes affording three Raf isoform members (B-Raf, C-Raf (Raf-1) and A-Raf). Each of these proteins share highly conserved amino-terminal regulatory regions and catalytic domains at the carboxy terminus. Unless otherwise indicated, Raf refers to all three members. Although each isoform plays a role in the Ras/Raf/MEK/ERK pathway, B-Raf has been shown to be the main activator of MEK. B-Raf is recruited by Ras:GTP to the intracellular cell membrane where B-Raf becomes activated. In turn, B-Raf is responsible for activation of MEK1/2 and MEK1/2 activate ERK1/ERK2. Mutations in the B-Raf gene allow for B-Raf to signal independently of upstream signals. As a result, mutated B-Raf protein (such as V600E) causes excessive downstream signaling of MEK and ERK. This leads to excessive cell proliferation and survival and oncogenesis. Overactivation of the signaling cascade by mutated B-Raf has been implicated in multiple malignancies.

The receptor tyrosine kinase (RTK) c-Kit (also called CD117), is expressed on a wide variety of cell types. The ligand for c-KIT is stem cell factor (SCF). The binding of SCF to the extracellular domain of c-KIT induces receptor dimerization and activation of downstream signaling pathways, including the RAS/RAF/MEK/ERK pathway. Mutant c-KIT has been implicated in the pathogenesis of several cancers.

Despite B-Raf specific inhibitors (such as vemurafenib), and compounds such as those disclosed in WO 2006/039718 and WO 2008/034008, there is a need for a Raf inhibitor active in inhibiting all isoforms of Raf proteins including A-Raf, B-Raf, C-Raf, and B-Raf V600E mutation. There is a further need for a Raf inhibitor that is active against tumor cells with upstream pathway activation by N-Ras mutations, K-Ras mutations, and cKit mutations. Furthermore, there remains a need to provide alternative Raf inhibitors for treatment of cancer. There also remains a need to provide alternative Raf inhibitors active in inhibiting A-Raf, B-Raf, C-Raf, and B-Raf V600E mutation for treatment of cancer. Accordingly, the present invention provides a Raf inhibitor which may be active in inhibiting all isoforms of Raf proteins. Also, the present invention provides a Raf inhibitor which may be active against tumor cells with upstream pathway activation by N-Ras mutations, K-Ras mutations, and cKit mutations. Additionally, the present invention provides an alternative inhibitor of Raf. Furthermore, the present invention provides an alternative inhibitor of Raf which may be useful for treating cancer. The present invention also provides an alternative inhibitor of Raf active in inhibiting A-Raf, B-Raf, C-Raf, and/or B-Raf V600E mutation. Still further, the present invention provides an alternative inhibitor of Raf active in inhibiting A-Raf, B-Raf, C-Raf, and/or B-Raf V600E mutation which may be useful for treating cancer.

One aspect of the present invention are compounds of Formula I:

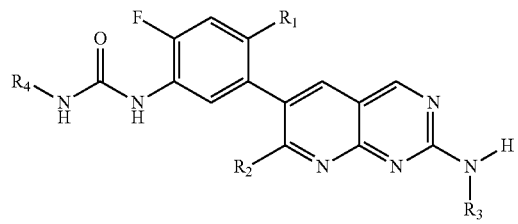

Formula I wherein:
$R_1$ is hydrogen, methyl, ethyl or halo;
$R_2$ is hydrogen, methyl or ethyl;
$R_3$ is hydrogen, acetyl, oxetan-3-yl, $C_1$-$C_4$ alkyl optionally substituted with imidazol-4-yl optionally substituted with a methyl or ethyl, $C_2$-$C_4$ alkyl substituted with hydroxyl, $C_1$-$C_2$ alkoxy, ($C_1$-$C_4$ alkyl)$_n$ amino-, and n is 0, 1, or 2, N-morpholino, N-piperidinyl, or N-pyrrolidinyl;
$R_4$ is $R_5$—($CH_2$)—, or $C_4$-$C_6$ cycloalkyl optionally substituted with one or two of the same or different methyl, ethyl, or fluoro;
$R_5$ is —$CHR_6R_7$ or $C_3$-$C_6$ cycloalkyl optionally substituted with one or two of the same or different $C_1$-$C_2$ alkyl;
$R_6$ is hydrogen or hydroxyl;
$R_7$ is isopropyl, t-butyl, 1-fluoro-1-methyl-ethyl, 1-cyano-1-methyl-ethyl, 1-methoxy-1-methyl-ethyl, 1-methylcycloprop-1-yl, 1-trifluoromethylcycloprop-1-yl, or 2,2,2-trifluoro-1,1-dimethyl-ethyl;
provided that the following substituents as a group are not simultaneously allowed:
$R_1$ is methyl;
$R_2$ is methyl;
$R_3$ is methyl;
$R_4$ is $R_5$—($CH_2$)—;
$R_5$ is —$CHR_6R_7$;
$R_6$ is hydrogen;
$R_7$ is t-butyl;
or a pharmaceutically acceptable salt thereof.

A second aspect of the present invention provides a pharmaceutical composition comprising a compound of Formula I, or a pharmaceutically acceptable salt thereof, in association with a pharmaceutically acceptable carrier.

A third aspect of the present invention provides a method of inhibiting Raf in a cancer patient in need thereof, comprising administering a therapeutically effective amount of a compound of Formula I, or a pharmaceutically acceptable salt thereof, to said patient.

A fourth aspect of the present invention provides a method of treating a cancer which is acute myelogenous leukemia (AML), chronic myelogenous leukemia (CML), chronic lymphoblastic leukemia (CLL), myelodysplastic syndrome, ovarian cancer, melanoma, small-cell lung cancer, non-small-cell lung cancer, colorectal cancer, pancreatic cancer, prostate cancer, liver cancer or thyroid cancer in a patient comprising administering to a patient in need thereof a therapeutically effective amount of a compound of Formula I, or a pharmaceutically acceptable salt thereof.

A fifth aspect of the present invention provides a method of treating a cancer which is thyroid cancer, ovarian cancer, melanoma, AML or colorectal cancer in a patient comprising administering to a patient in need thereof a therapeutically effective amount of a compound of Formula I, or a pharmaceutically acceptable salt thereof.

A sixth aspect of the present invention provides a compound of Formula I, or a pharmaceutically acceptable salt thereof, for use in therapy.

A seventh aspect of the present invention provides a compound of Formula I, or a pharmaceutically acceptable salt thereof, for use in the treatment of a cancer which is acute myelogenous leukemia (AML), chronic myelogenous leukemia (CML), chronic lymphoblastic leukemia (CLL), myelodysplastic syndrome, ovarian cancer, melanoma, small-cell lung cancer, non-small-cell lung cancer, colorectal cancer, pancreatic cancer, prostate cancer, liver cancer or thyroid cancer.

An eighth aspect of the present invention provides a compound of Formula I, or a pharmaceutically acceptable salt thereof, for use in the treatment of a cancer which is thyroid cancer, ovarian cancer, melanoma, AML or colorectal cancer.

A ninth aspect of the present invention provides use of a compound of Formula I or a pharmaceutically acceptable salt thereof, for the manufacture of a medicament for the treatment of a cancer which is acute myelogenous leukemia (AML), chronic myelogenous leukemia (CML), chronic lymphoblastic leukemia (CLL), myelodysplastic syndrome, ovarian cancer, melanoma, small-cell lung cancer, non-small-cell lung cancer, colorectal cancer, pancreatic cancer, prostate cancer, liver cancer or thyroid cancer.

A tenth aspect of the present invention provides use of a compound of Formula I, or a pharmaceutically acceptable salt thereof, for the manufacture of a medicament for the treatment of a cancer which is thyroid cancer, ovarian cancer, melanoma, AML or colorectal cancer.

An eleventh aspect of the present invention provides use of a compound of Formula I, or a pharmaceutically acceptable salt thereof, for use in the treatment of cancer.

In one embodiment, the compounds of Formula I are those wherein:
$R_1$ is hydrogen, methyl, fluoro or bromo;
$R_2$ is hydrogen or methyl;
$R_3$ is hydrogen, methyl, ethyl, acetyl, 2-methoxyethyl, 2-hydroxyethyl, oxetan-3-yl, 2-dimethylaminoethyl, N-morpholinoethyl, (1-methylimidazol-4-yl)methyl;
$R_4$ is $R_5$—$(CH_2)$—, or 3,3-dimethylcyclobutyl;
$R_5$ is —$CHR_6R_7$, or 2,2-dimethylcycloprop-1-yl;
$R_6$ is hydrogen or hydroxyl;
$R_7$ is t-butyl, 1-fluoro-1-methyl-ethyl, 1-cyano-1-methylethyl, 1-methoxy-1-methyl-ethyl, 1-methylcycloprop-1-yl, 1-trifluoromethylcycloprop-1-yl, or 2,2,2-trifluoro-1,1-dimethyl-ethyl;
provided that the following substituents as a group are not simultaneously allowed:
$R_1$ is methyl;
$R_2$ is methyl;
$R_3$ is methyl;
$R_4$ is $R_5$—$(CH_2)$—;
$R_5$ is —$CHR_6R_7$;
$R_6$ is hydrogen;
$R_7$ is t-butyl;
or a pharmaceutically acceptable salt thereof.

In another embodiment, the compounds of Formula I are those wherein:
$R_1$ is hydrogen, methyl or fluoro;
$R_2$ is hydrogen or methyl;
$R_3$ is hydrogen, methyl, acetyl, 2-hydroxyethyl, or N-morpholinoethyl;
$R_4$ is $R_5$—$(CH_2)$—, or 3,3-dimethylcyclobutyl;
$R_5$ is —$CHR_6R_7$;
$R_6$ is hydrogen or hydroxyl;
$R_7$ is t-butyl, 1-cyano-1-methyl-ethyl, 1-methylcycloprop-1-yl, 1-trifluoromethylcycloprop-1-yl, or 2,2,2-trifluoro-1,1-dimethyl-ethyl;
provided that the following substituents as a group are not simultaneously allowed:
$R_1$ is methyl;
$R_2$ is methyl;
$R_3$ is methyl;
$R_4$ is $R_5$—$(CH_2)$—;
$R_5$ is —$CHR_6R_7$;
$R_6$ is hydrogen;
$R_7$ is t-butyl;
or a pharmaceutically acceptable salt thereof.

In another embodiment of the compounds of Formula I or pharmaceutically acceptable salts thereof, $R_1$ is hydrogen.

In another embodiment of the compounds of Formula I or pharmaceutically acceptable salts thereof, $R_1$ is methyl.

In another embodiment of the compounds of Formula I or pharmaceutically acceptable salts thereof, $R_1$ is fluoro.

In another embodiment of the compounds of Formula I or pharmaceutically acceptable salts thereof, $R_2$ is hydrogen.

In another embodiment of the compounds of Formula I or pharmaceutically acceptable salts thereof, $R_2$ is methyl.

In another embodiment of the compounds of Formula I or pharmaceutically acceptable salts thereof, $R_3$ is hydrogen.

In another embodiment of the compounds of Formula I or pharmaceutically acceptable salts thereof, $R_3$ is methyl.

In another embodiment of the compounds of Formula I or pharmaceutically acceptable salts thereof, $R_3$ is 2-hydroxyethyl.

In another embodiment of the compounds of Formula I or pharmaceutically acceptable salts thereof, $R_3$ is N-morpholinoethyl.

In another embodiment of the compounds of Formula I or pharmaceutically acceptable salts thereof, $R_4$ is 3,3-dimethylcyclobutyl.

In another embodiment of the compounds of Formula I or pharmaceutically acceptable salts thereof, $R_4$ is $R_5$—$(CH_2)$—.

In another embodiment of the compounds of Formula I or pharmaceutically acceptable salts thereof, $R_5$ is —$CHR_6R_7$, $R_6$ is hydroxyl, and $R_7$ is t-butyl.

In another embodiment of the compounds of Formula I or pharmaceutically acceptable salts thereof, $R_5$ is —$CHR_6R_7$, $R_6$ is hydrogen, and $R_7$ is t-butyl, 1-cyano-1-methyl-ethyl, 1-methylcycloprop-1-yl, 1-trifluoromethylcycloprop-1-yl, or 2,2,2-trifluoro-1,1-dimethyl-ethyl.

Another embodiment is a compound of the formula:

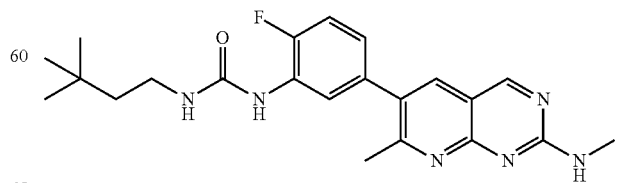

or a pharmaceutically acceptable salt thereof.

Another embodiment is a compound of the formula:

or a pharmaceutically acceptable salt.

Another embodiment is a compound of the formula:

or a pharmaceutically acceptable salt thereof.

Another embodiment is a compound of the formula:

or a pharmaceutically acceptable salt thereof.

Another embodiment is a compound of the formula:

or a pharmaceutically acceptable salt thereof.

Another embodiment is a compound of the formula:

or a pharmaceutically acceptable salt thereof.

Another embodiment is a compound of the formula:

or a pharmaceutically acceptable salt thereof.

Another embodiment is a compound of the formula:

or a pharmaceutically acceptable salt thereof.

Another embodiment is a compound of the formula:

or a pharmaceutically acceptable salt thereof.

Another embodiment is a compound of the formula:

or a pharmaceutically acceptable salt thereof.

Another embodiment is a compound of the formula:

Stereo Mixture or a pharmaceutically acceptable salt thereof.

Another aspect of the present invention provides compounds of Formula IA:

Formula IA wherein:
$R_1$ is hydrogen, $C_1$-$C_4$alkyl, or halo;
$R_2$ is $C_1$-$C_4$alkyl or hydrogen;
$R_3$ is $C_1$-$C_4$ alkyl, hydrogen, —C(O)$R_8$, oxetanyl, tetrahydrofuranyl, or tetrahydropyranyl;
and wherein the $C_1$-$C_4$ alkyl is optionally substituted with hydroxyl, $C_1$-$C_2$ alkoxy, oxetanyl, tetrahydrofuranyl, tetrahydropyranyl, N-azetidinyl, N-piperazinyl, $C_5$-$C_6$ heteroaryl, N-morpholino, N-piperidinyl, N-pyrrolidinyl, or ($C_1$-$C_4$ alkyl)$_n$ amino- wherein n is 0, 1, or 2; and wherein each of the rings as substituents on a $C_1$-$C_4$ alkyl are further optionally substituted with one to three of the same or different $C_1$-$C_4$ alkyl, fluoro, $C_1$-$C_4$ alkoxy, —C(O)$R_8$, or ($C_1$-$C_4$ alkyl)$_m$ amino, where m is 0, 1 or 2;
$R_4$ is $R_5$—(CH$_2$)—, or $C_4$-$C_6$ cycloalkyl optionally substituted with one or two of the same or different methyl, ethyl, or fluoro;
$R_5$ is —CHR$_6$R$_7$ or $C_3$-$C_6$ cycloalkyl optionally substituted with one or two of the same or different $C_1$-$C_2$ alkyl;
$R_6$ is hydrogen or hydroxyl, or $C_1$-$C_4$ alkoxy;
$R_7$ is isopropyl, t-butyl, 1-fluoro-1-methyl-ethyl, 1-cyano-1-methyl-ethyl, 1-($C_1$-$C_4$ alkoxy)-1-methyl-ethyl, 1-($C_1$-$C_4$ alkyl)-cycloprop-1-yl, 1-(fluoro($C_1$-$C_2$ alkyl)cycloprop-1-yl, or 2,2,2-trifluoro-1,1-dimethyl-ethyl where fluoro($C_1$-$C_2$ alkyl) has one to five fluoro substituents;
$R_8$ is hydrogen, $C_1$-$C_6$ linear or branched alkyl, or ($C_1$-$C_4$)$_p$ amino where p is 0, 1, or 2, and each alkyl is optionally substituted with the same or different $C_1$-$C_4$ alkoxy, hydroxyl, or ($C_1$-$C_4$ alkyl)$_q$amino and q is 0, 1, or 2;
provided that the following substituents as a group are not simultaneously allowed:
$R_1$ is methyl;
$R_2$ is methyl;
$R_3$ is methyl;
$R_4$ is $R_5$—(CH$_2$)—;
$R_5$ is —CHR$_6$R$_7$;
$R_6$ is hydrogen;
$R_7$ is t-butyl;
or a pharmaceutically acceptable salt thereof.

Another embodiment of the present invention provides compounds of Formula IA, wherein:
$R_1$ is hydrogen, methyl, ethyl or halo;
$R_2$ is hydrogen, methyl or ethyl;
$R_3$ is hydrogen, —C(O)$R_8$, oxetanyl, tetrahydrofuranyl, tetrahydropyranyl, or $C_1$-$C_4$ alkyl optionally substituted with hydroxyl, $C_1$-$C_2$ alkoxy, ($C_1$-$C_4$ alkyl)$_n$ amino-, and n is 0, 1, or 2, oxetanyl, tetrahydrofuranyl, tetrahydropyranyl, N-azetidinyl, N-piperazinyl, imidazolyl, N-morpholino, N-piperidinyl, or N-pyrrolidinyl, wherein each of the rings as substituents on a $C_1$-$C_4$ alkyl are optionally substituted with one to three of the same or different $C_1$-$C_4$ alkyl, fluoro, $C_1$-$C_4$ alkoxy, —C(O)$R_8$, or ($C_1$-$C_4$ alkyl)$_m$amino, where m is 0, 1 or 2;
$R_4$ is $R_5$—(CH$_2$)—, or $C_4$-$C_6$ cycloalkyl optionally substituted with one or two of the same or different methyl, ethyl, or fluoro;
$R_5$ is —CHR$_6$R$_7$ or $C_3$-$C_6$ cycloalkyl optionally substituted with one or two of the same or different $C_1$-$C_2$ alkyl;
$R_6$ is hydrogen or hydroxyl, or $C_1$-$C_4$ alkoxy;
$R_7$ is isopropyl, t-butyl, 1-fluoro-1-methyl-ethyl, 1-cyano-1-methyl-ethyl, 1-($C_1$-$C_4$ alkoxy)-1-methyl-ethyl, 1-($C_1$-$C_4$ alkyl)-cycloprop-1-yl, 1-(fluoro($C_1$-$C_2$ alkyl)cycloprop-1-yl, or 2,2,2-trifluoro-1,1-dimethyl-ethyl where fluoro($C_1$-$C_2$ alkyl) has one to five fluoro substituents;
$R_8$ is hydrogen, $C_1$-$C_6$ linear or branched alkyl, or ($C_1$-$C_4$)$_p$ amino where p is 0, 1, or 2, and each alkyl is optionally substituted with the same or different $C_1$-$C_4$ alkoxy, hydroxyl, or ($C_1$-$C_4$ alkyl)$_q$amino and q is 0, 1, or 2;
provided that the following substituents as a group are not simultaneously allowed:
$R_1$ is methyl;
$R_2$ is methyl;
$R_3$ is methyl;
$R_4$ is $R_5$—(CH$_2$)—;
$R_5$ is —CHR$_6$R$_7$;
$R_6$ is hydrogen;
$R_7$ is t-butyl;
or a pharmaceutically acceptable salt thereof.

The term "halo" means chloro, fluoro and bromo.

The term "alkyl" as used herein refers to straight chain or branched alkyl, wherein alkyl chain length is indicated by a range of numbers, In exemplary embodiments, "alkyl" refers to an alkyl chain as defined above containing 1, 2, 3, 4, 5, or 6 carbons (i.e., $C_1$-$C_6$ alkyl). Examples of an alkyl include, but are not limited to, methyl, ethyl, propyl, iso-propyl, butyl, iso-butyl, secondary-butyl, tertiary-butyl, n-pentyl, 2-pentyl, 3-pentyl, n-hexyl, 2-hexyl, and 3-hexyl.

The term "alkoxy" as used herein refers to —O-(alkyl), wherein "alkyl" is as defined above.

The term "heteroaryl" as used herein refers to a cyclic hydrocarbon, where at least one of the ring atoms is an O, N, or S, the ring is characterized by delocalized π electrons (aromaticity) shared among the ring members, and wherein the number of ring atoms is indicated by a range of numbers. Heteroaryl moieties as defined herein have C or N bonding hands. For example, in some embodiments, a ring N atom from the heteroaryl is the bonding atom of the heteroaryl moiety. In exemplary embodiments, "heteroaryl" refers to a cyclic hydrocarbon as described above containing 5 or 6 ring atoms (i.e., $C_5$-$C_6$ heteroaryl). Examples of a heteroaryl group include, but are not limited to, pyrrole, furan, thiene, oxazole, thiazole, isoxazole, isothiazole, imidazole, pyrazole, oxadiazole, thiadiazole, triazole, tetrazole, pyridine, pyrimidine, pyrazine, pyridazine, and triazine.

The term "cycloalkyl" as used herein refers to a monocyclic saturated carbon ring, wherein the number of ring atoms is indicated by a range of numbers. In exemplary embodiments, "cycloalkyl" refers to a carbon ring as defined above containing 3, 4, 5 or 6 ring atoms (i.e., $C_3$-$C_6$ cycloalkyl). Examples of a cycloalkyl group include, but are not limited to, cyclopropyl, cyclobutyl, cyclopentyl, and cyclohexyl.

The term "Stereo Mixture" means a mixture of stereoisomers.

The term "patient" means mammal and "mammal" includes, but is not limited to, a human.

"Therapeutically effective amount" or "effective amount" means the dosage of the compound, or pharmaceutically acceptable salt thereof, or pharmaceutical composition containing an exemplified compound of Formula I, or pharmaceutically acceptable salt thereof, necessary to inhibit B-Raf, C-Raf, A-Raf and/or B-Raf V600E signaling in a cancer patient, and either destroy the target cancer cells or slow or arrest the progression of the cancer in a patient. Anticipated dosages of the exemplified compounds of Formula I, or a pharmaceutically acceptable salt thereof, are in the range of 300 to 1500 mg/patient/day. Preferred dosages are anticipated to be in the range of 400 to 1400 mg/patient/day. Most preferred dosages are anticipated to be in the range of 600 to 1200 mg/patient/day. The exact dosage required to treat a patient and the length of treatment time will be determined by a physician in view of the stage and severity of the disease as well as the specific needs and response of the individual patient and the particular compound administered. Although expressed as dosage on a per day basis, the dosing regimen may be adjusted to provide a more optimal therapeutic benefit to a patient. In addition to daily dosing, twice-a-day (BID) or thrice-a-day (TID) dosing may be appropriate. BID dosing is currently preferred.

The terms "treatment," "treat," and "treating," are meant to include the full spectrum of intervention for the cancer from which the patient is suffering, such as administration of the active compound to alleviate, slow or reverse one or more of the symptoms of the cancer and to delay progression of the cancer even if the cancer is not actually eliminated.

The exemplified compounds of the present invention are preferably formulated as a pharmaceutical composition using a pharmaceutically acceptable carrier or using one or more pharmaceutically acceptable carriers, diluents, or excipients and administered by a variety of routes. Preferably, such compositions are for oral administration. Such pharmaceutical compositions and processes for preparing them are well known in the art. See, e.g., REMINGTON: THE SCIENCE AND PRACTICE OF PHARMACY (A. Gennaro, et al., eds., 21$^{st}$ ed., Mack Publishing Co., 2005).

The exemplified compounds of the present invention are capable of reaction with a number of inorganic and organic acids to form pharmaceutically acceptable acid addition salts. Such pharmaceutically acceptable salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," *Journal of Pharmaceutical Sciences*, Vol. 66, No. 1, January 1977.

It should be understood the compounds of Formula I and IA include only those compounds that satisfy steric requirements, are physically stable to unimolecular decomposition, and are isolable.

The compounds of Formula I, or a pharmaceutically acceptable salt thereof, may be prepared by a variety of procedures known in the art, as well as those described below. The specific synthetic steps may be combined in different ways to prepare the Formula I compounds, or a pharmaceutically acceptable salt thereof.

The compounds of Formula I may be named by various nomenclature systems to unambiguously identify them.

The compounds employed as initial starting materials in the synthesis of the compounds of Formula I are well known and, to the extent not commercially available, are readily synthesized using specific references provided, by standard procedures commonly employed by those of ordinary skill in the art, or are found in general reference texts.

Examples of known procedures and methods include those described in general reference texts such as Comprehensive Organic Transformations, VCH Publishers Inc, 1989; Compendium of Organic Synthetic Methods, Volumes 1-10, 1974-2002, Wiley Interscience; Advanced Organic Chemistry, Reactions Mechanisms, and Structure, 5$^{th}$ Edition, Michael B. Smith and Jerry March, Wiley Interscience, 2001; Advanced Organic Chemistry, 4$^{th}$ Edition, Part B, Reactions and Synthesis, Francis A. Carey and Richard J. Sundberg, Kluwer Academic/Plenum Publishers, 2000, etc., and references cited therein.

As used herein, the following terms have the meanings indicated: "DCM" refers to dichloromethane; "DMF" refers to dimethylformamide; "DMSO' refers to dimethyl sulfoxide; "DPPA" refers to diphenylphosphoryl azide, "EtOAc" refers to ethyl acetate; "EtOH" refers to ethanol; "HPLC" refers to high performance liquid chromatography; "IPA" refers to isopropyl alcohol; "mCPBA" refers to meta-chloroperoxybenzoic acid; "MS" refers to mass spectroscopy; "MeCN" refers to acetonitrile; "MeOH" refers to methanol; "MTBE" refers to tert-butyl methyl ether; "NMR" refers to nuclear magnetic resonance; "RT" refers to room temperature; "TEA" refers to triethylamine; "THF" refers to tetrahydrofuran.

Unless noted to the contrary, the compounds illustrated herein are named and numbered using either ACDLABS or Symyx Draw 3.2.

GENERAL CHEMISTRY

The compounds of the present invention can be prepared according to the following synthetic schemes by methods well known and appreciated in the art. Suitable reaction conditions for the steps of these schemes are well known in the art and appropriate substitutions of solvents and co-reagents are within the skill of the art. Likewise, it will be appreciated by those skilled in the art that synthetic intermediates may be isolated and/or purified by various well known techniques as needed or desired, and that frequently, it will be possible to use various intermediates directly in subsequent synthetic steps with little or no purification. Furthermore, the ordinary skilled artisan will appreciate that in some circumstances, the order in which moieties are introduced is not critical. The particular order of steps required to produce the compounds of Formula I is dependent upon the particular compound being synthesized, the starting compound, and the relative liability of the substituted moieties, as is well appreciated by the ordinary skilled chemist. All substituents, unless otherwise indicated, are as previously defined, and all reagents are well known and appreciated in the art Scheme I

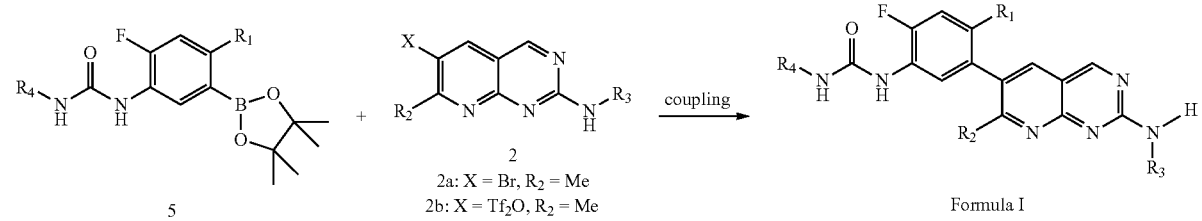

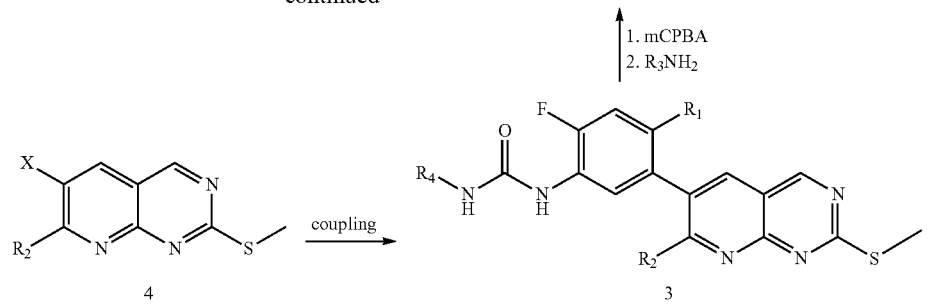

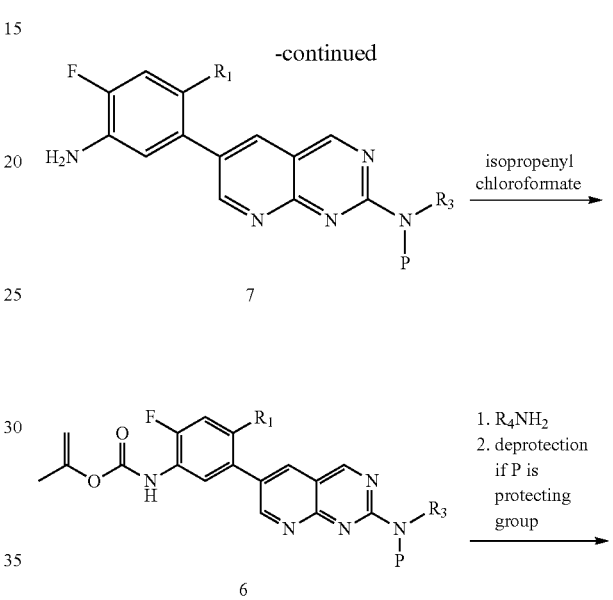

Compounds of Formula I can be synthesized as illustrated in Scheme I.

Compound 5 can react with compound 2 under well known palladium coupling conditions to provide the compound of Formula I. More specifically, compound 5 is reacted with compound 2 in the presence of a suitable base such as sodium bicarbonate or potassium carbonate, an appropriate catalyst such as tetrakis(triphenylphosphine)palladium (Pd(PPh$_3$)$_4$) in a suitable solvent mixture such as dioxane and water at elevated temperature to provide a compound of Formula I. Compounds of Formula I can also be synthesized through an alternative route. More specifically, compound 5 is reacted with compound 4 under the similar palladium coupling conditions just described to provide compound 3. Compound 3 is further reacted with a suitable oxidative reagent such as meta-chloroperoxybenzoic acid in a suitable solvent such as dichloromethane followed by reaction with an appropriate amine to provide a compound of Formula I.

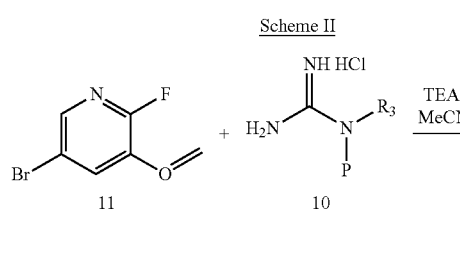

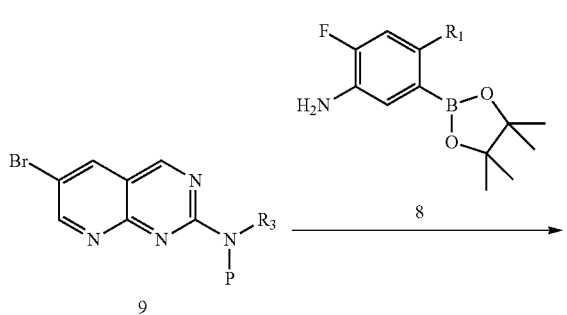

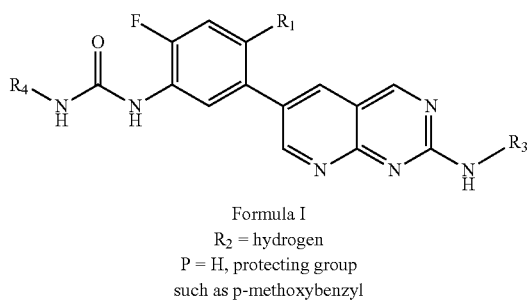

Compounds of Formula I can also be synthesized as illustrated in Scheme II when R$_2$ is hydrogen.

Compound 11 and compound 10 are reacted in a suitable solvent such as acetonitrile in the presence of a suitable base such as triethylamine at elevated temperature to provide compound 9. Compound 9 and compound 8 are reacted under well known palladium coupling conditions described above to provide compound 7, which is further reacted with isopropenyl chloroformate to give compound 6. Compound 6 is reacted with an appropriate amine to provide a compound of Formula I when P is hydrogen. When P is an amine protecting group such as p-methoxybenzyl, compound 6 is treated with a de-protecting reagent such as trifluoroacetic acid to provide a compound of Formula I Scheme III

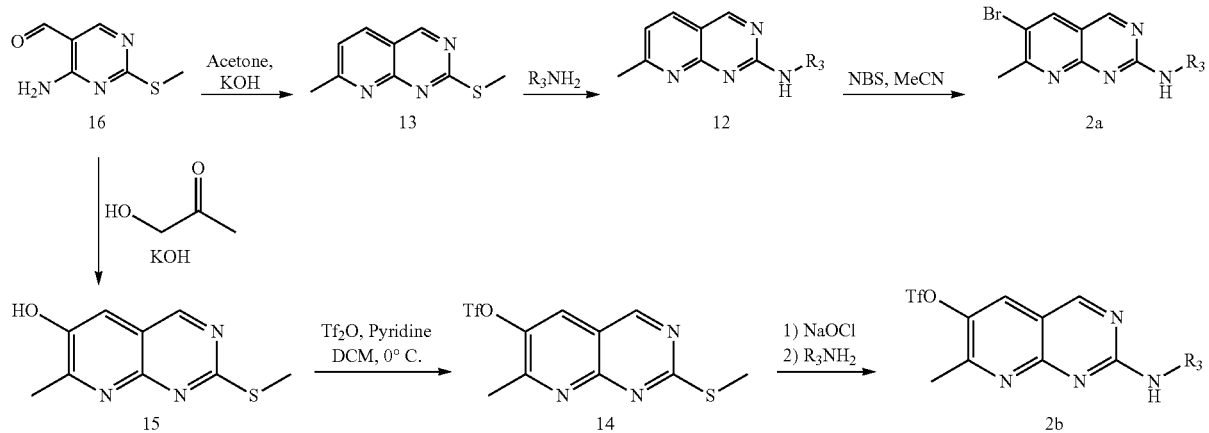

Compound 2a and 2b (2a: X=Br, 2b: X=TfO) can be synthesized as illustrated in Scheme III.

Compound 16 is reacted with acetone and a suitable base such as potassium hydroxide to provide compound 13, which is further reacted with an appropriate amine in a suitable solvent such as ethanol at elevated temperature to provide compound 12. Compound 12 is reacted with a suitable brominating reagent such as N-bromosuccinimide in a suitable solvent such as acetonitrile to provide compound 2a.

Compound 16 can also be reacted with 1-hydroxypropan-2-one and sodium hydroxide in a solution of water and ethanol to provide compound 15, which is further reacted with trifluoromethanesulfonic anhydride and a suitable base such as pyridine in an appropriate solvent such as dichloromethane to provide compound 14. Compound 14 is then reacted with a suitable oxidative reagent such as bleach followed by reaction with an appropriate amine to provide compound 2b.

Compound 5 can be synthesized as illustrated in Scheme IV.

Compound 18 is reacted with bis(pinacolato)diboron, a suitable base such as potassium acetate, and a suitable catalyst such as [1,1'-bis(diphenylphosphino)ferrocene]-dichloropalladium(II)-dichloromethane complex in an appropriate solvent such as dioxane at elevated temperature to provide compound 8. Compound 8 is reacted with a suitable carboxylic acid, diphenylphosphoryl azide, a suitable base such as triethylamine in an appropriate solvent such as dioxane at elevated temperature to provide compound 5. Alternatively, compound 8 is reacted with isopropenyl chloroformate to provide compound 17, which is further reacted with a suitable amine to provide compound 5.

Scheme IV

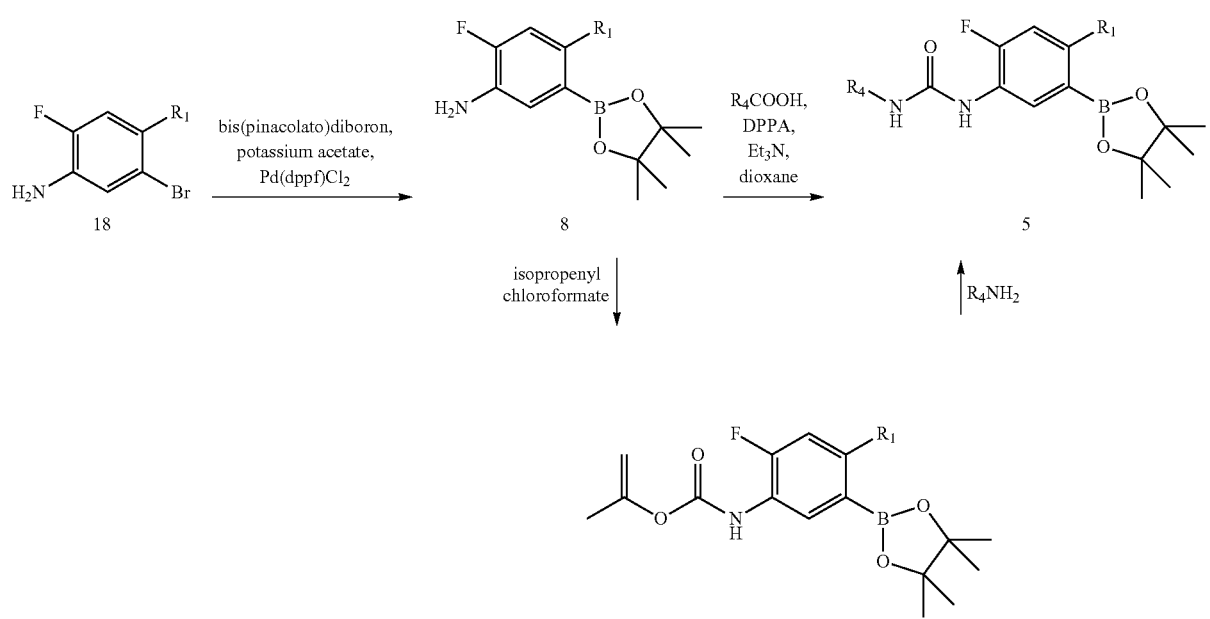

Preparation 1

Benzyl (2-bromoethyl)carbamate

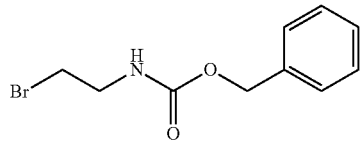 [SMILES: O=C(NCCBr)OCc1ccccc1]

Treat a 0° C. solution of 2-bromoethylamine hydrobromide (50 g, 0.246 mol) in dioxane (500 mL) with aqueous NaOH (1 M, 492 mL, 0.492 mol), add benzyl chloroformate (21.6 g, 0.127 mol) dropwise, warm to RT and stir overnight. Pour the mixture into $H_2O$, extract with EtOAc (3×), wash the combined organics with brine, dry over $Na_2SO_4$, concentrate to dryness and purify via silica gel chromatography (EtOAc/Petroleum ether) to afford the title compound (60 g, 95%) as a white solid. $^1$H NMR (400 MHz, CDCl$_3$): δ 7.37-7.33 (m, 5H), 5.12 (s, 2H), 3.61 (t, J=5.6 Hz, 2H), 3.47 (t, J=5.6 Hz, 2H).

Preparation 2

Benzyl (3-cyano-3-methylbutyl)carbamate

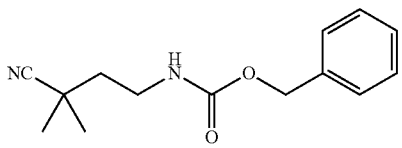 [SMILES: CC(C)(C#N)CCNC(=O)OCc1ccccc1]

Treat a −78° C. solution of diisopropylamine (35 g, 0.346 mol) in THF (300 mL), under $N_2$, dropwise with a solution of n-butyllithium (2.5 M, 127 mL, 0.317 mol), warm to −30° C. for 0.5 h, re-cool to −78° C. and treat dropwise with a solution of isobutyronitrile (19.9 g, 0.288 mol) in THF (100 mL). Stir the mixture at −78° C. for 0.5 h, treat with a solution of benzyl (2-bromoethyl)carbamate (74 g, 0.288 mol) in THF (100 mL), stir at −78° C. for 1 h, then warm to RT and stir overnight. Treat the mixture with $H_2O$, separate the layers, extract the aqueous layer with EtOAc, wash the combined organics with brine, dry over $Na_2SO_4$, concentrate to dryness and purify via silica gel chromatography (EtOAc/Petroleum ether) to afford the title compound (15 g, 21% yield). MS (m/z): 247.2 (M+1).

Preparation 3

4-Amino-2,2-dimethylbutanenitrile

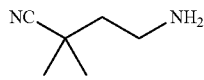

Treat a solution of benzyl (3-cyano-3-methylbutyl)carbamate (2.50 g, 10.15 mmol) in THF (75 mL) with 10% Pd/C (1.080 g) and stir at RT under a hydrogen balloon for 2 h. Filter the mixture through diatomaceous earth, rinse well with THF and concentrate the filtrate to dryness to afford the title compound (assume 100% yield). MS (m/z): 113.2 (M+1).

Preparation 4

Ethyl 3-(dibenzylamino)propanoate

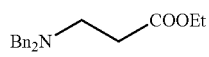

Heat a solution of ethyl 3-aminopropanoate hydrochloride (80.0 g, 0.52 mol), benzylbromide (186.7 g, 1.1 mol) and $K_2CO_3$ (179.4 g, 1.3 mol) in acetonitrile (1 L) at 40° C. overnight. Concentrate the mixture to dryness, treat with water, extract with EtOAc (3×), wash the combined organics with brine, dry over $Na_2SO_4$, concentrate to dryness and purify via silica gel chromatography chromatography (Pet Ether/EtOAc, 50:1) to afford the title compound (150 g, 97% yield). $^1$H NMR (400 MHz, CDCl$_3$): δ 7.35-7.21 (m, 10H), 4.09 (q, J=7.2 Hz, 2H), 3.58 (s, 4H), 2.82 (t, J=7.2 Hz, 2H), 2.50 (t, J=7.2 Hz, 2H), 1.21 (t, J=7.2 Hz, 3H).

Preparation 5

4-(Dibenzylamino)-2-methylbutan-2-ol

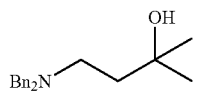

Cool a solution of ethyl 3-(dibenzylamino)propanoate (150 g, 0.51 mol) in THF (1 L) to 0° C. Add methylmagnesium bromide (505 mL, 1.51 mol) dropwise over 1 h, then heat at 70° C. under $N_2$ overnight. Re-cool the mixture to 0° C. and treat dropwise with saturated aqueous $NH_4OH$. Extract the mixture with EtOAc (3×), wash the combined organics with brine, dry over $Na_2SO_4$, concentrate to dryness and purify via silica gel chromatography to afford the title compound (140 g, 98%). MS (m/z): 284.2 (M+1).

Preparation 6

N,N-Dibenzyl-3-fluoro-3-methylbutan-1-amine

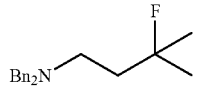

In a cooled solution (−78° C.) of 4-(dibenzylamino)-2-methylbutan-2-ol (110.0 g, 0.39 mol) in DCM (1 L), add diethylaminosulfur trifluoride (75 g, 0.47 mol) dropwise under $N_2$, allow it to warm to RT and stir overnight. Re-cool the mixture to −78° C., add dropwise with saturated NaHCO$_3$ (300 mL), warm to RT, extract with EtOAc (3×), wash the combined organics with brine, dry over $Na_2SO_4$, concentrate to dryness and purify via silica gel chromatography (0.1-0.2% EtOAc/pet ether) to afford the title compound (44.0 g, 40% yield). MS (m/z): 286.2 (M+1).

Preparation 7

3-Fluoro-3-methylbutan-1-amine acetic acid salt

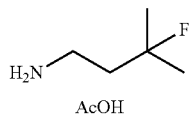

Treat a solution of N,N-dibenzyl-3-fluoro-3-methylbutan-1-amine (18.03 g, 63.2 mmol) in MeOH (150 mL) and acetic acid (7.23 mL, 126 mmol) with 10% Pd/C (3.36 g, 3.16 mmol) and hydrogenate (345 kPa) for 2.5 days. Add additional palladium on carbon (1 g) and hydrogenate the mixture (345 kPa) overnight. Filter the mixture through diatomaceous earth, rinse well with MeOH and concentrate the filtrate to dryness to afford the title compound MS (m/z): 106.1 (M-AcOH+1).

Preparation 8

N,N-Dibenzyl-3-methoxy-3-methylbutan-1-amine

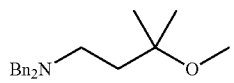

Add potassium hydride (30%, 2.6 g, 19.4 mmol) portionwise under $N_2$ to a cooled solution (0° C.) of 4-(dibenzylamino)-2-methylbutan-2-ol (5 g, 17.6 mmol) in THF (50 mL). Stir the mixture at 0° C. for 0.5 h, treat with MeI (2.76 g, 19.4 mmol) dropwise, allow the mixture to warm to RT and stir for 3 h. Re-cool the mixture to 0° C., treat with saturated. $NH_4Cl$, and remove the organics under reduced pressure. Extract the residue with EtOAc (3×), wash the combined organics with brine, dry over $Na_2SO_4$, concentrate and purify via silica gel chromatography (Pet ether/EtOAc, 50:1) to afford the title compound (3.0 g, 57% yield). $^1$H NMR (400 MHz, DMSO-$d_6$): δ 7.29 (m, 10H), 3.58 (s, 4H), 3.05 (s, 3H), 2.50 (m, 2H), 1.73 (m, 2H), 1.07 (s, 6H).

Preparation 9

3-Methoxy-3-methylbutan-1-amine hydrochloride

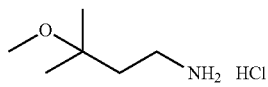

Treat a solution of N,N-dibenzyl-3-methoxy-3-methylbutan-1-amine (3 g, 10.1 mmol) in MeOH (50 mL) with palladium hydroxide on carbon (1 g) and stir the mixture under atmospheric $H_2$ at RT for 3 h. Remove the solids via filtration, wash with EtOAc, treat the filtrate dropwise with methanolic HCl and concentrate to dryness to afford the title compound (1.01 g, 66% yield). $^1$H NMR (400 MHz, DMSO-$d_6$): δ 8.04 (s, 2H), 3.05 (s, 3H), 2.52-2.49 (m, 2H), 1.74-1.70 (m, 2H), 1.07 (s, 6H).

Preparation 10

5-Bromo-2-fluoro-4-methylaniline

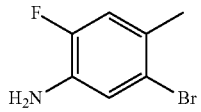

Combine 1-bromo-4-fluoro-2-methylbenzene (30.0 g, 159 mmol) in concentrated sulfuric acid (100 mL), cool to about −5° C., and treat dropwise with nitric acid (11.00 mL, 174 mmol) over 20 minutes. Allow reaction mixture to warm to RT and stir for 30 min. Pour onto crushed ice with stirring and partition with tert-butyl methyl ether (MTBE) (200 mL). Separate the aqueous layer and extract with MTBE (2×50 mL). Combine organic layers, dry and concentrate under reduced pressure to provide 1-bromo-4-fluoro-2-methyl-5-nitrobenzene as an orange-colored viscous oil (39.0 g).

Combine crude 1-bromo-4-fluoro-2-methyl-5-nitrobenzene (32.4 g, 138 mmol), ethanol (100 mL) and Raney Nickel (1.00 g, 17.04 mmol) in a shaker flask. Charge the flask with hydrogen (275 kPa) and agitate until the absorption of hydrogen ceases. De-pressurize the reaction vessel, remove the catalyst by filtration, and evaporate the filtrate to dryness. Add MTBE, then filter again and evaporate the filtrate. Stir residue in hexanes. Collect the solids by filtration, wash with cold hexanes and dry in vacuo to provide the title compound (17.8 g, 63% yield) as a dark solid. MS (m/z): 204.0 (M+1)/206.0 (M+3).

Preparation 11

2-Fluoro-4-methyl-5-(4,4,5,5-tetramethyl-1,3,2-dioxaborolan-2-yl)aniline

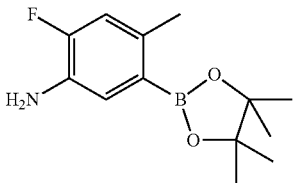 [SMILES: Cc1cc(F)c(N)cc1B1OC(C)(C)C(C)(C)O1]

Combine 5-bromo-2-fluoro-4-methylaniline (3.1 g, 15.2 mmol), bis(pinacolato)diboron (4.24 g, 16.7 mmol), and potassium acetate (4.47 g, 45.6 mmol) in dioxane (40 mL) and sparge with argon. Add [1,1'-bis(diphenylphosphino)ferrocene]-dichloropalladium(II)-dichloromethane complex (0.620 g, 0.760 mmol), sparge again with argon and heat at 100° C. overnight. Filter the reaction mixture and concentrate in vacuo. Purify by silica gel chromatography (0-50% EtOAc/hexanes) to give the title compound (3.24 g, 85% yield). MS (m/z): 252.1 (M+1).

The following compounds are prepared essentially by the method of Preparation 11.

| Prep No. | Chemical Name | Structure | Physical data MS (m/z): |
|---|---|---|---|
| 12 | 2,4-Difluoro-5-(4,4,5,5-tetramethyl-1,3,2-dioxaborolan-2-yl)aniline | 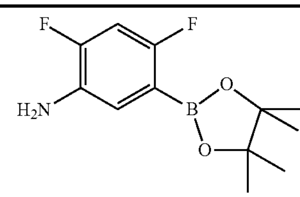 | 256.2 (M + 1) |
| | 2-Fluoro-5-(4,4,5,5-tetramethyl-1,3,2-dioxaborolan-2-yl)aniline | | 238.1 (M + 1) |

Preparation 14

Prop-1-en-2-yl 2-fluoro-4-methyl-5-(4,4,5,5-tetramethyl-1,3,2-dioxaborolan-2-yl)phenylcarbamate

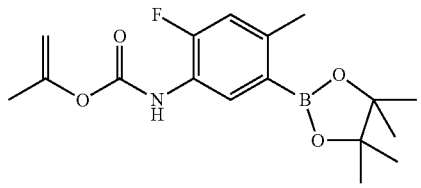 [SMILES: C=C(C)OC(=O)Nc1cc(B2OC(C)(C)C(C)(C)O2)c(C)cc1F]

Add 2-fluoro-4-methyl-5-(4,4,5,5-tetramethyl-1,3,2-dioxaborolan-2-yl)aniline (5.0 g, 19.91 mmol) and isopropenyl chloroformate (2.40 mL, 21.90 mmol) in EtOAc (60 mL) and saturated aqueous NaHCO$_3$ (60 mL) and stir at RT for 6 h. Separate the layers, extract the aqueous layer with EtOAc (2×), wash the combined organics with brine, dry over Na$_2$SO$_4$ and concentrate to obtain the title compound. Use for the next reaction without further purification (assuming 100% yield). MS (m/z): 336.2 (M+1).

The following compounds are prepared essentially by the method of Preparation 14.

| Prep No. | Chemical Name | Structure | Physical data |
|---|---|---|---|
| 15 | Prop-1-en-2-yl (2,4-difluoro-5-(4,4,5,5-tetramethyl-1,3,2-dioxaborolan-2-yl)phenyl)carbamate | 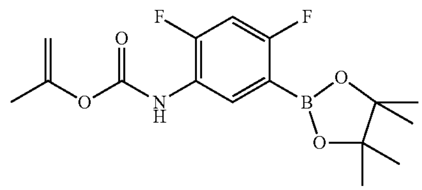 [SMILES: C=C(C)OC(=O)Nc1cc(B2OC(C)(C)C(C)(C)O2)c(F)cc1F] | MS(m/z): 340.1 (M + 1) |
| 16 | Prop-1-en-2-yl (2-fluoro-5-(4,4,5,5-tetramethyl-1,3,2-dioxaborolan-2-yl)phenyl)carbamate | 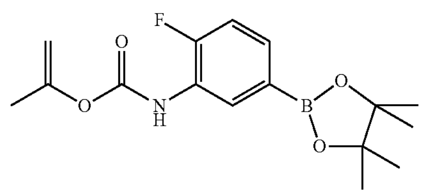 [SMILES: C=C(C)OC(=O)Nc1cc(B2OC(C)(C)C(C)(C)O2)ccc1F] | MS(m/z): 322.1 (M + 1) |
| 17 | Prop-1-en-2-yl (3,3-dimethylbutyl)carbamate | 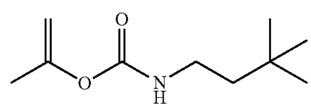 | $^1$H NMR (400 MHz, DMSO-d$_6$): δ 7.33 (s, 1 H), 4.55 (d, J = 12.6 Hz, 2 H), 3.00-2.93 (m, 2 H), 1.82 (s, 3 H), 1.36-1.29 (m, 2 H), 0.86 (s, 9 H). |

Preparation 18

1-(3,3-Dimethylbutyl)-3-(2-fluoro-4-methyl-5-(4,4,5,5-tetramethyl-1,3,2-dioxaborolan-2-yl)phenyl)urea

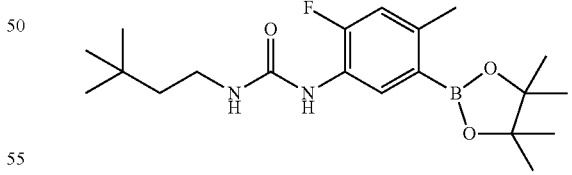

Treat a solution of prop-1-en-2-yl 2-fluoro-4-methyl-5-(4,4,5,5-tetramethyl-1,3,2-dioxaborolan-2-yl)phenylcarbamate (6.67 g, 19.90 mmol) in dioxane (60 mL) with 3,3-dimethylbutan-1-amine (2.42 g, 23.9 mmol) and 1-methylpyrrolidine (0.169 g, 1.99 mmol) and heat at 75° C. overnight. Cool the mixture to RT, collect the solid via filtration and wash with diethyl ether to obtain the title compound (6.62 g, 88% yield over two steps). MS (m/z): 379.2 (M+1).

The following compounds are prepared essentially by the method of Preparation 18.

| Prep No. | Chemical Name | Structure | Physical data MS(m/z): |
|---|---|---|---|
| 19 | 1-(3,3-Dimethylbutyl)-3-(2-fluoro-5-(4,4,5,5-tetramethyl-1,3,2-dioxaborolan-2-yl)phenyl)urea | 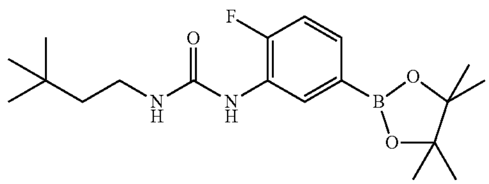 [SMILES: CC(C)(C)CCNC(=O)Nc1cc(B2OC(C)(C)C(C)(C)O2)ccc1F] | 365.2 (M + 1) |
| 20 | 1-(2,4-Difluoro-5-(4,4,5,5-tetramethyl-1,3,2-dioxaborolan-2-yl)phenyl)-3-(3,3-dimethylbutyl)urea | 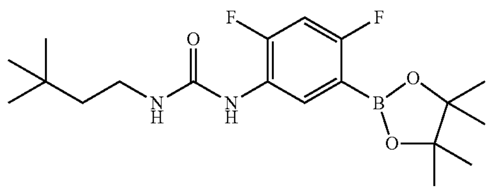 [SMILES: CC(C)(C)CCNC(=O)Nc1cc(B2OC(C)(C)C(C)(C)O2)c(F)cc1F] | 383.2 (M + 1) |
| 21 | 1-(3-Cyano-3-methylbutyl)-3-(2-fluoro-4-methyl-5-(4,4,5,5-tetramethyl-1,3,2-dioxaborolan-2-yl)phenyl)urea | 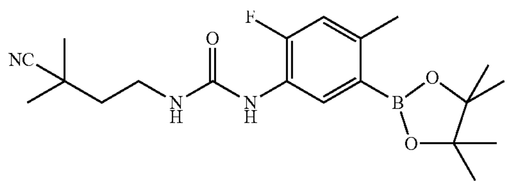 [SMILES: Cc1cc(F)c(NC(=O)NCCC(C)(C)C#N)cc1B1OC(C)(C)C(C)(C)O1] | 390.2 (M + 1) |
| 22 | 1-(3-Fluoro-3-methylbutyl)-3-(2-fluoro-4-methyl-5-(4,4,5,5-tetramethyl-1,3,2-dioxaborolan-2-yl)phenyl)urea | 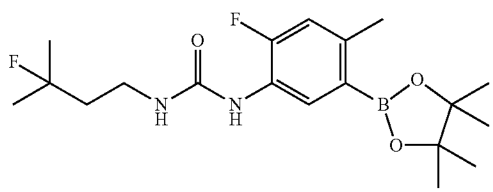 [SMILES: Cc1cc(F)c(NC(=O)NCCC(C)(C)F)cc1B1OC(C)(C)C(C)(C)O1] | 383.2 (M + 1) |
| 23 | 1-(2-Fluoro-4-methyl-5-(4,4,5,5-tetramethyl-1,3,2-dioxaborolan-2-yl)phenyl)-3-(3-methoxy-3-methylbutyl)urea | 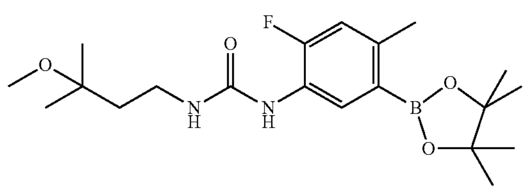 | 395.2 (M + 1) |
| 24 | 1-[2-Fluoro-4-methyl-5-(4,4,5,5-tetramethyl-1,3,2-dioxaborolan-2-yl)phenyl]-3-(2-hydroxy-3,3-dimethyl-butyl)urea | 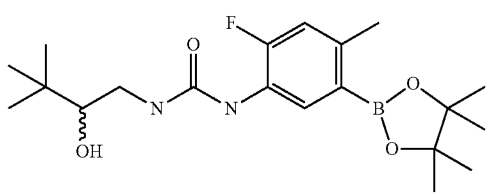 [SMILES: Cc1cc(F)c(NC(=O)NCC(O)C(C)(C)C)cc1B1OC(C)(C)C(C)(C)O1] | 395.2 (M + 1) |
| 25 | 1-[(2,2-Dimethylcycloprop-yl)methyl]-3-[2-fluoro-4-methyl-5-(4,4,5,5-tetramethyl-1,3,2-dioxaborolan-2-yl)phenyl]urea | 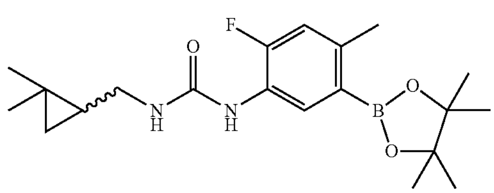 | 377.2 (M + 1) |
| 26 | 1-[2,4-Difluoro-5-(4,4,5,5-tetramethyl-1,3,2-dioxaborolan-2-yl)phenyl]-3-(2-hydroxy-3,3-dimethyl-butyl)urea | 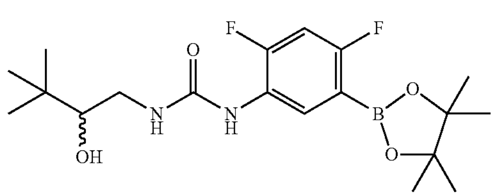 [SMILES: CC(C)(C)C(O)CNC(=O)Nc1cc(B2OC(C)(C)C(C)(C)O2)c(F)cc1F] | 398.8 (M + 1) |

Preparation 27

1-(3,3-Dimethylcyclobutyl)-3-(2-fluoro-4-methyl-5-(4,4,5,5-tetramethyl-1,3,2-dioxaborolan-2-yl)phenyl)urea

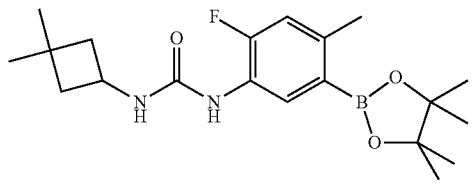

Heat a mixture of 3,3-dimethylcyclobutanecarboxylic acid (0.230 g, 1.792 mmol), 2-fluoro-4-methyl-5-(4,4,5,5-tetramethyl-1,3,2-dioxaborolan-2-yl)aniline (0.30 g, 1.195 mmol), triethylamine (TEA) (0.331 mL, 2.389 mmol) and diphenylphosphoryl azide (DPPA) (0.519 mL, 2.389 mmol) in dioxane (10 mL) at 100° C. for 2 h. Cool the mixture to RT, concentrate to dryness and purify via silica gel chromatography (10-100% EtOAc/Hexanes) to afford the title compound (220 mg, 49% yield). MS (m/z): 377.2 (M+1).

The following compound is prepared essentially by the method of Preparation 27.

| Prep No. | Chemical Name | Structure | Physical data MS (m/z): |
|---|---|---|---|
| 28 | 1-(2,4-Difluoro-5-(4,4,5,5-tetramethyl-1,3,2-dioxaborolan-2-yl)phenyl)-3-(3,3-dimethylcyclobutyl)urea | 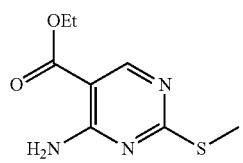 | 381.2 (M + 1) |

Preparation 29

Ethyl 4-amino-2-(methylthio)pyrimidine-5-carboxylate

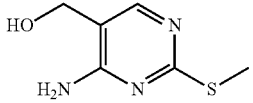

Add concentrated ammonium hydroxide (335 mL, 8.60 mol) to a vigorously stirred suspension of ethyl 4-chloro-2-(methylthio)pyrimidine-5-carboxylate (200 g, 860 mmol) in ethanol (EtOH) (450 mL) and allow to stir overnight. Collect the solids by filtration, rinse with EtOH (2×100 mL) and $H_2O$ (3×200 mL) and dry in a vacuum oven (65-70° C.) overnight to afford the title compound (164.4 g, 90% yield) as a white solid. MS (m/z): 214.1 (M+1).

Preparation 30

4-Amino-2-(methylthio)pyrimidin-5-yl)methanol

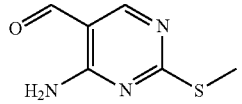

Cool a solution of ethyl 4-amino-2-(methylthio)pyrimidine-5-carboxylate (72.3 g, 339 mmol) in tetrahydrofuran (THF) (900 mL) to 0° C. Add a solution of $LiAlH_4$ (2 M in THF) (195 mL, 390 mmol) dropwise over 1 h. Stir for 2 h at 0° C. and allow the reaction to warm to RT overnight. Cool the mixture to 0° C. and cautiously quench by the sequential addition of water (15 mL), 20% aq. KOH (15 mL) and water (30 mL). Stir the resulting mixture for 1 h. Dry over $MgSO_4$, filter, concentrate under reduced pressure, and dry under vacuum to obtain the title compound (55.85 g, 96% yield). MS (m/z): 172.1 (M+1).

Preparation 31

4-amino-2-(methylthio)pyrimidine-5-carbaldehyde

Add $MnO_2$ (49.8 g, 572 mmol) to a suspension of 4-amino-2-(methylthio)pyrimidin-5-yl)methanol (28 g, 164 mmol) in chloroform (818 mL) and heat the reaction at 55° C. (measure internally) for 4 h. Filter the hot reaction mixture and rinse the filter cake with hot chloroform and THF. Concentrate the combined filtrates under reduced pressure and dry under vacuum to afford the title compound (26.7 g, 96% yield) as a pale yellow solid MS (m/z): 170.1 (M+1).

Preparation 32

7-Methyl-2-(methylthio)pyrido[2,3-d]pyrimidin-6-ol

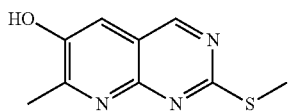

Add 1-hydroxypropan-2-one (24.3 mL, 355 mmol) and 4-amino-2-(methylthio)pyrimidine-5-carbaldehyde (50 g, 296 mmol) to a solution of sodium hydroxide (23.64 g, 591 mmol) and water (200 mL). Add EtOH (600 mL) to the suspension and stir at RT overnight. Slowly add a solution of concentrated HCl (50 mL) in water (350 mL). Add 1:1 EtOH/H$_2$O (100 mL) and collect the solids by filtration. Wash the solids with 1:1 EtOH/H$_2$O (250 mL), ice cold EtOH (4×25 mL) and hexanes (2×250 mL). Dry in the vacuum oven at 30-35° C. to provide the title compound as a tan solid (34 g, 56% yield). MS (m/z): 208.1 (M+1).

Preparation 33

7-Methyl-2-(methylthio)pyrido[2,3-d]pyrimidin-6-yl trifluoromethanesulfonate

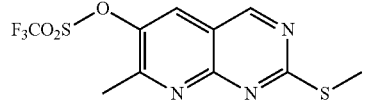

Combine 7-methyl-2-(methylthio)pyrido[2,3-d]pyrimidin-6-ol (25 g, 121 mmol), DCM (1100 mL) and pyridine (98 mL, 1206 mmol) and cool the mixture with an ice bath until the internal temperature <3° C. Add trifluoromethanesulfonic anhydride (24.5 mL, 145 mmol) slowly via syringe at such a rate that the internal temperature is maintained below 5° C. Stir the reaction mixture at 0° C. for 2 h. Wash with water (3×300 mL) and brine (300 mL), dry over MgSO$_4$, and filter. Concentrate the filtrate under reduced pressure (water bath temp ~35° C.) and dry under high vacuum for 2-3 h at RT. Dissolve the residue in DCM and purify by silica gel chromatography (EtOAc/hexanes). Concentrate fractions to afford a semi-pure solid. Triturate the solid with 20% EtOAc/hexanes (100 mL), collect by filtration, rinse with 20% EtOAc/hexanes (2×10 mL) and dry under vacuum at RT to afford the title compound as a pale pink solid (28.6 g, 70% yield). MS (m/z): 340.0 (M+1).

Preparation 34

(7-Methyl-2-methylsulfonyl-pyrido[2,3-d]pyrimidin-6-yl) trifluoromethanesulfonate

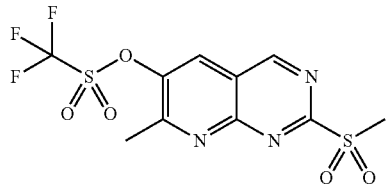 [SMILES: Cc1nc2nc(S(C)(=O)=O)ncc2cc1OS(=O)(=O)C(F)(F)F]

Add acetic acid (11.5 mmol; 0.66 mL) to a solution of (7-methyl-2-methylsulfanyl-pyrido[2,3-d]pyrimidin-6-yl) trifluoromethanesulfonate (5.76 mmol; 1.96 g) in dimethylformamide (4.6 mL) and heat to 55° C. Add sodium hypochlorite (35 mmol, 24 mL) dropwise over 1 h then stir at 55° C. overnight. Cool to RT, filter out solids, rinse with water, and dry on filter to obtain the title compound (1.54 g, 90%). $^1$H NMR (400 MHz, DMSO): δ 10.05 (s, 1H), 9.04 (s, 1H), 3.52 (s, 3H), 2.85 (s, 3H).

Preparation 35

7-Methyl-2-(methylamino)pyrido[2,3-d]pyrimidin-6-yl trifluoromethanesulfonate

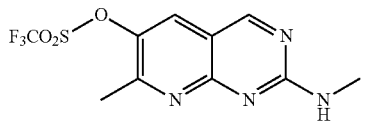

Heat a mixture 7-methyl-2-(methylthio)pyrido[2,3-d]pyrimidin-6-yl trifluoromethanesulfonate (28.6 g, 84 mmol), dimethylformamide (74 mL) and glacial acetic acid (9.61 mL, 169 mmol) to 45° C. and then add 6.15% aqueous NaOCl (bleach, 612 g, 506 mmol) dropwise over 2 h. Heat at 45-50° C. for 2 h, cool to RT, collect the solids by filtration and wash with water (300 mL). Add DCM (200 mL) to the solids, cool the suspension in an ice-water bath and treat with a solution of 2.0 M N-methylamine in THF (126 mL, 253 mmol). Allow the mixture to slowly warm to RT and stir for 2 h. Remove the solvent under reduced pressure, treat with methanol (MeOH) (50 mL) and stir at RT for 30 min. Collect the solid by filtration and wash with MeOH. Treat the solid with EtOAc (30 mL) and stir at RT for 30 min. Collect the solid by filtration and wash with EtOAc to obtain the title compound (19.82 g, 73% yield). MS (m/z): 323.0 (M+1).

The following compounds are prepared essentially by the procedure of Preparation 35.

| Prep No | Chemical Name | Structure | Physical data MS (m/z): |
|---|---|---|---|
| 36 | [2-(2-Hydroxyethylamino)-7-methyl-pyrido[2,3-d]pyrimidin-6-yl] trifluoromethanesulfonate | 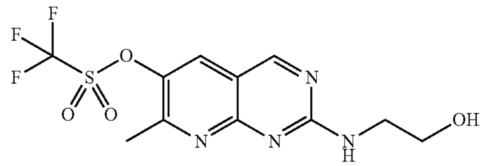 [SMILES: Cc1nc2nc(NCCO)ncc2cc1OS(=O)(=O)C(F)(F)F] | 353.0 (M + 1) |
| 37 | [2-(2-Dimethylaminoethylamino)-7-methyl-pyrido[2,3-d]pyrimidin-6-yl] trifluoromethanesulfonate | 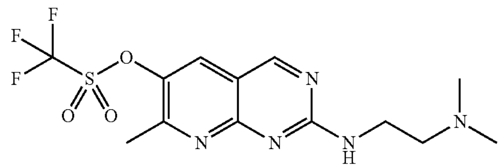 [SMILES: Cc1nc2nc(NCCN(C)C)ncc2cc1OS(=O)(=O)C(F)(F)F] | 380.0 (M + 1) |
| 38 | (2-Amino-7-methyl-pyrido[2,3-d]pyrimidin-6-yl) trifluoromethanesulfonate | 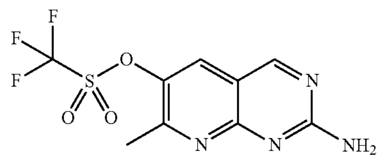 [SMILES: Cc1nc2nc(N)ncc2cc1OS(=O)(=O)C(F)(F)F] | 308.8 (M + 1) |

Preparation 39

N,7-Dimethylpyrido[2,3-d]pyrimidin-2-amine

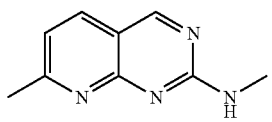

Treat a solution of 4-amino-2-(methylthio)pyrimidine-5-carbaldehyde (10 g, 59.1 mmol) in acetone (100 mL) with KOH (3.32 g, 59.1 mmol), stir at RT for 10 min, then concentrate to dryness. Treat the residue with EtOAc, wash with saturated. Aqueous NaHCO₃, then brine, dry over Na₂SO₄ and concentrate to obtain 7-methyl-2-(methylthio)pyrido[2,3-d]pyrimidine. MS (m/z): 192.1 (M+1). Add a solution of methylamine in ethanol (33%, 80 mL) and heat at 110° C. overnight in a pressure tube. Remove the solvent under reduced pressure and purify the crude product by silica gel chromatography (50-100% EtOAc/Hexanes) to obtain the title compound (6.73 g, 65%, over two steps). MS (m/z): 175.1 (M+1).

Preparation 40

6-Bromo-N,7-dimethylpyrido[2,3-d]pyrimidin-2-amine

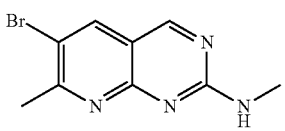

Cool a solution of N,7-dimethylpyrido[2,3-d]pyrimidin-2-amine (6.73 g, 38.6 mmol) in acetonitrile (160 mL) in an ice bath and shield from light with aluminum foil. Add N-bromosuccinimide (6.88 g, 38.6 mmol) and stir at 0° C. for 2 h. Transfer the reaction to a 5° C. refrigerator for 4 days. Collect the solid by filtration. Wash the solid with DCM and concentrate the washings to obtain the title compound (3.0 g, 31% yield). MS (m/z): 253.0/255.0 (M+1).

Preparation 41

6-Bromo-N-(2-methoxyethyl)-7-methylpyrido[2,3-d]pyrimidin-2-amine

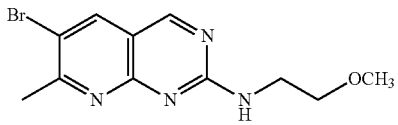 [SMILES: COCCNc1ncc2cc(Br)c(C)nc2n1]

Heat a solution of 7-methyl-2-(methylthio)pyrido[2,3-d]pyrimidine (2.6 g, 13.6 mmol) and 2-methoxyethanamine (6 mL) with microwave irradiation at 180° C. for 2 h. Cool the mixture to RT, dissolve in EtOAc, wash with water, then brine, dry over Na₂SO₄ and concentrate under reduced pressure to give N-(2-methoxyethyl)-7-methylpyrido[2,3-d]pyrimidin-2-amine (2.7 g, 91%). Treat a solution of N-(2-methoxyethyl)-7-methylpyrido[2,3-d]pyrimidin-2-amine (2.35 g, 10.7 mmol) in THF (100 mL) portion wise with NBS (1.8 g, 10.7 mmol) and stir at RT for 2 h. Concentrate the reaction mixture to dryness, dissolve in EtOAc, wash with water, then brine, dry the organics over Na$_2$SO$_4$, concentrate and purify by HPLC to afford the title compound (0.55 g, 26%). MS (m/z): 297.0 (M+1$^+$).

Preparation 42

1-(3,3-Dimethylbutyl)-3-(2-fluoro-4-methyl-5-(7-methyl-2-(methylthio)pyrido[2,3-d]pyrimidin-6-yl)phenyl)urea

Combine 1-(3,3-dimethylbutyl)-3-(2-fluoro-4-methyl-5-(4,4,5,5-tetramethyl-1,3,2-dioxaborolan-2-yl)phenyl)urea (0.669 g, 1.768 mmol), 7-methyl-2-(methylthio)pyrido[2,3-d]pyrimidin-6-yl trifluoromethanesulfonate (0.6 g, 1.768 mmol), K$_2$CO$_3$ (0.733 g, 5.30 mmol) and Pd(PPh$_3$)$_4$ (0.102 g, 0.088 mmol) in dioxane (8 mL) and water (2 mL) in a pressure tube, sparge with argon, seal and heat at 100° C. overnight. Cool the mixture to RT, treat with saturated aqueous. NaHCO$_3$ and extract with EtOAc (3×). Dry the combined organics over MgSO$_4$, concentrate to dryness and purify via silica gel chromatography (5-100% EtOAc/Hexanes) to afford the title compound (440 mg, 56%). MS (m/z): 442.2 (M+1).

The following compound is prepared essentially by the method of Preparation 42.

(2.93 g, 25.5 mmol) dropwise. Stir the mixture at 0° C. for 2 h, wash with H$_2$O then brine, dry over Na$_2$SO$_4$ and concentrate to dryness to afford the title compound (3.66 g, 96%) as an oil. $^1$H NMR (400 MHz, DMSO-d$_6$): δ 3.60 (s, 3H), 2.10 (m, 2H), 0.72 (s, 3H), 0.14 (m, 2H), 0.01 (m, 2H).

Preparation 45

2-(1-Methylcyclopropyl)acetonitrile

Treat a solution of (1-methylcyclopropyl)methyl methanesulfonate (3.66 g, 22.29 mmol) in DMSO (35 mL) with sodium cyanide (2.18 g, 44.6 mmol) and stir at RT for 5 h. Dilute the mixture with H$_2$O and extract with EtOAc (3×). Wash the combined organics with brine, dry over Na$_2$SO$_4$ and concentrate to dryness to afford the title compound as an oil. Use without further purification (assuming 100% yield). $^1$H NMR (400 MHz, DMSO-d$_6$): δ 1.45 (m, 2H), 0.76 (s, 3H), 0.09 (m, 2H), 0.01 (m, 2H).

| Prep No. | Chemical Name | Structure | Physical data MS (m/z): |
|---|---|---|---|
| 43 | 1-(3-Fluoro-3-methylbutyl)-3-(2-fluoro-4-methyl-5-(7-methyl-2-(methylthio)pyrido[2,3-d]pyrimidin-6-yl)phenyl)urea | 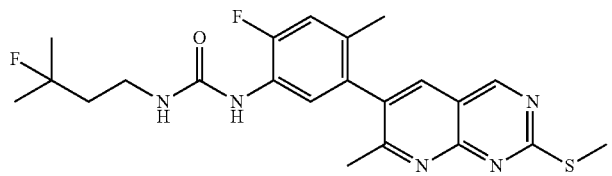 [SMILES: CSc1ncc2cc(-c3cc(NC(=O)NCCC(C)(C)F)c(F)cc3C)c(C)nc2n1] | 446.1 (M + 1) |

Preparation 44

(1-Methylcyclopropyl)methyl methanesulfonate

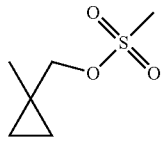

Treat a cooled solution (0° C.) of 1-methylcyclopropanemethanol (2.0 g, 23.22 mmol) in DCM (75 mL) with TEA (2.58 g, 25.5 mmol) and add methanesulfonyl chloride Preparation 46

2-(1-Methylcyclopropyl)ethanamine hydrochloride

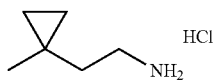

Treat a solution of 2-(1-methylcyclopropyl)acetonitrile (2.120 g, 22.28 mmol) in THF (25 mL) with borane dimethylsulfide complex (2N, 18.94 mL, 37.9 mmol) at RT then heat to reflux for 4 h. Carefully add 1.25 N HCl in MeOH (32 mL, 40 mmol), heat the mixture at 65° C. for 4 h, cool to RT and stir overnight. Concentrate the mixture to dryness, treat the residue with EtOAc, and concentrate to dryness again. Triturate the material with Et$_2$O, collect the solid via filtration and dry to afford the title compound as a solid (915 mg, 30% yield). $^1$H NMR (400 MHz, DMSO-$d_6$): δ 8.14 (s, 2H), 2.85-2.78 (m, 2H), 1.55-1.49 (m, 2H), 0.98 (s, 3H), 0.33-0.20 (m, 4H).

Preparation 47

4,4,4-Trifluoro-3,3-dimethylbutanamide

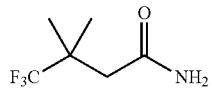

Treat a 0° C. solution of 4,4,4-trifluoro-3,3-dimethylbutanoic acid [See: US2010/0240663] (17 g, 100 mmol) in acetonitrile (200 mL) with 1-(3-dimethylaminopropyl)-3-ethylcarbodiimide hydrochloride (23 g, 120 mmol) and 1-hydroxybenzotriazole (16.2 g, 120 mmol), stir at 0° C. for 2 h, treat with concentrated ammonia in water (25 wt %, 15 mL), allow to warm to RT and stir overnight. Remove the organics under reduced pressure, dissolve the residue in EtOAc, and wash with saturated. NaHCO$_3$, then brine, dry over MgSO$_4$, and concentrate to dryness. Treat the material with pet ether, collect the solid via filtration and dry to afford the title compound (13 g, 77% yield). $^1$H NMR (400 MHz, DMSO-d6): δ 7.46 (s, 1H), 6.93 (s, 1H), 2.19 (s, 2H), 1.18 (s, 6H).

Preparation 48

4,4,4-Trifluoro-3,3-dimethylbutan-1-amine hydrochloride

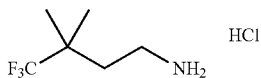

Treat a solution of 4,4,4-trifluoro-3,3-dimethylbutanamide (10 g, 59.1 mmol) in THF (120 mL) with BH$_3$ (1.0 M in THF, 295 mL, 295 mmol), stir for 15 min at RT, then heat to reflux overnight. Cool the mixture to 0° C., treat dropwise with MeOH, then methanolic HCl and partially concentrate under reduced pressure. Collect the solids via filtration, rinse with EtOAc and dry to afford the title compound as an off-white solid (5.2 g, 57% yield). $^1$H NMR (400 MHz, DMSO-d6): δ 8.10 (s, 3H), 2.83 (m, 2H), 1.81-1.76 (m, 2H), 1.11 (s, 6H).

Preparation 49

2-Fluoro-4-methyl-5-(7-methyl-2-(methylthio)pyrido[2,3-d]pyrimidin-6-yl)aniline

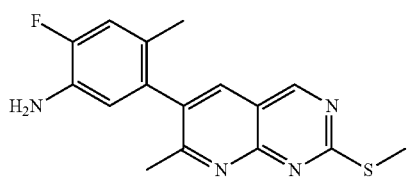 [SMILES: CSc1ncc2cc(-c3cc(N)c(F)cc3C)c(C)nc2n1]

Combine 2-fluoro-4-methyl-5-(4,4,5,5-tetramethyl-1,3,2-dioxaborolan-2-yl)aniline (370 mg, 1.474 mmol), 7-methyl-2-(methylthio)pyrido[2,3-d]pyrimidin-6-yl trifluoromethanesulfonate (500 mg, 1.474 mmol) and K$_2$CO$_3$ (611 mg, 4.42 mmol) in dioxane (12 mL) and H$_2$O (3 mL), sparge with argon, treat with Pd(PPh$_3$)$_4$ (85 mg, 0.074 mmol) and heat to 60° C. for 3 h. Cool the mixture to RT, stir overnight, treat with EtOAc and wash with brine. Filter the mixture, wash the organic layer again with brine, dry over Na$_2$SO$_4$, concentrate to dryness and purify via reverse-phase chromatography (MeCN/H$_2$O with 0.1% TFA). Combine fractions, remove the organics under reduced pressure and neutralize the aqueous residue with saturated. NaHCO$_3$. Extract the mixture with EtOAc (2×), wash the combined organics with brine, dry over Na$_2$SO$_4$ and concentrate to dryness to afford the title compound as an amorphous solid (373 mg, 81%). MS (m/z): 315.1 (M+1).

Preparation 50

Prop-1-en-2-yl (2-fluoro-4-methyl-5-(7-methyl-2-(methylthio)pyrido[2,3-d]pyrimidin-6-yl)phenyl)carbamate

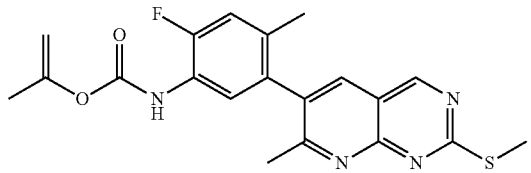 [SMILES: C=C(C)OC(=O)Nc1cc(-c2cc3cnc(SC)nc3nc2C)c(C)cc1F]

Add isopropenyl chloroformate (146 mg, 1.207 mmol) to a bi-phasic mixture of 2-fluoro-4-methyl-5-(7-methyl-2-(methylthio)pyrido[2,3-d]pyrimidin-6-yl)aniline (345 mg, 1.097 mmol) in EtOAc (15 mL) and saturated NaHCO$_3$ (20 mL) and stir at RT for 2 h. Add EtOAc, separate the layers, wash the organic layer with brine, dry over Na$_2$SO$_4$ and concentrate to dryness to afford the title compound as an amorphous solid (434 mg, 99%). MS (m/z): 399.1 (M+1).

Preparation 51

1-(2-Fluoro-4-methyl-5-(7-methyl-2-(methylthio)pyrido[2,3-d]pyrimidin-6-yl)phenyl)-3-(4,4,4-trifluoro-3,3-dimethylbutyl)urea

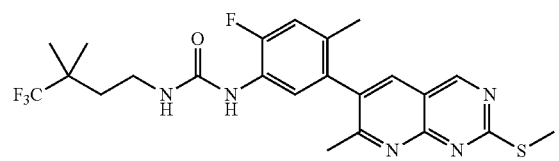 [SMILES: CSc1ncc2cc(-c3cc(NC(=O)NCCC(C)(C)C(F)(F)F)c(F)cc3C)c(C)nc2n1]

Add 1-methylpyrrolidine (1.214 mL, 11.54 mmol) in a mixture of prop-1-en-2-yl (2-fluoro-4-methyl-5-(7-methyl-2-(methylthio)pyrido[2,3-d]pyrimidin-6-yl)phenyl)carbamate (0.92 g, 2.31 mmol) and 4,4,4-trifluoro-3,3-dimethylbutan-1-amine hydrochloride (0.487 g, 2.54 mmol) in THF (23 mL) and heat at 65° C. for 4 h. Cool the mixture to RT, dilute with EtOAc, wash with brine (2×), dry over MgSO$_4$, concentrate to dryness and purify via silica gel chromatography (0-50% EtOAc/Hexanes) to afford the title compound (860 mg, 75% yield). MS (m/z): 496.2 (M+1).

The following compound is prepared essentially by the method of Preparation 51.

| Prep No. | Chemical Name | Structure | Physical data MS (ESI) m/z: |
|---|---|---|---|
| 52 | 1-(2-Fluoro-4-methyl-5-(7-methyl-2-(methylthio)pyrido[2,3-d]pyrimidin-6-yl)phenyl)-3-(2-(1-methylcyclopropyl)ethyl)urea | 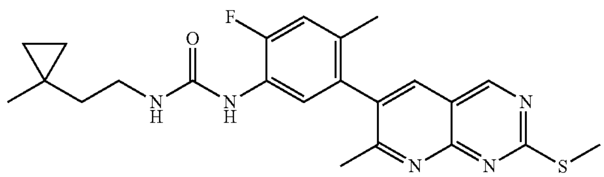 | 440.1 (M + 1) |

Preparation 53

(1-(Trifluoromethyl)cyclopropyl)methanol

Treat a cooled solution (0° C.) of 1-(trifluoromethyl)cyclopropanecarboxylic acid (9 g, 58.4 mmol) in Et$_2$O (140 mL) under N$_2$, with LiAlH$_4$ (2.9 g, 76 mmol) portion wise, allow to warm to RT and stir overnight. Re-cool the mixture to 0° C., treat slowly with HCl, warm to RT and separate the layers. Extract the aqueous layer with diethyl ether (2×), wash the combined organics with brine, dry over Na$_2$SO$_4$ and concentrate in a cool (<30° C.) water bath to afford the title compound (7 g, 86% yield). $^1$H NMR (400 MHz, DMSO-d$_6$): δ 4.94 (t, J=6.0 Hz, 1H), 3.54 (d, J=6.0 Hz, 2H), 0.87-0.84 (m, 2H), 0.81-0.79 (m, 2H).

Preparation 54

(1-(Trifluoromethyl)cyclopropyl)methyl 4-methylbenzenesulfonate

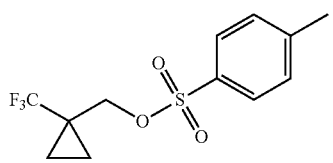 [SMILES: Cc1ccc(S(=O)(=O)OCC2(C(F)(F)F)CC2)cc1]

Treat a solution of (1-(trifluoromethyl)cyclopropyl)methanol (7 g, 50 mmol) and 4-methylbenzene-1-sulfonyl chloride (10.4 g, 55 mmol) in anhydrous DCM (100 mL) with TEA (10 g, 100 mmol) and N,N-dimethylpyridin-4-amine (0.6 g, 5 mmol). Stir at RT overnight. Wash the mixture successively with HCl (2M), saturated NaHCO$_3$, and brine, dry over Na$_2$SO$_4$ and concentrate under reduced pressure to give the title compound (12 g, 81% yield). $^1$H NMR (400 MHz, DMSO-d$_6$): δ 7.79 (d, J=8.0 Hz, 2H), 7.50 (d, J=8.0 Hz, 2H), 4.13 (s, 2H), 2.43 (s, 3H), 1.08-1.05 (m, 2H), 0.96-0.94 (m, 2H).

Preparation 55

2-(1-(Trifluoromethyl)cyclopropyl)acetonitrile

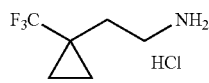

Treat a solution of (1-(trifluoromethyl)cyclopropyl)methyl 4-methylbenzenesulfonate (12 g, 40.8 mmol) in DMF (150 mL) with potassium cyanide (3.5 g, 53 mmol) and heat at 50-70° C. for 3 days. Treat the mixture with water, extract with EtOAc (3×), wash the combined organics with water, then brine, dry and concentrate under reduced pressure to give the title compound (2.4 g, 39% yield). $^1$H NMR (400 MHz, CDCl$_3$): δ 2.81 (s, 2H), 1.24-1.18 (m, 2H), 0.95-0.92 (m, 2H).

Preparation 56

2-(1-(Trifluoromethyl)cyclopropyl)ethanamine hydrochloride

Treat a solution of 2-(1-(trifluoromethyl)cyclopropyl)acetonitrile (2.2 g, 14.7 mmol) in THF (60 mL), under N$_2$, with BH$_3$ (10 M in dimethyl sulfide, 3 mL, 30 mmol) and heat at 70° C. overnight. Cool the mixture to 0° C., treat dropwise with methanolic HCl, concentrate to dryness, dissolve in MeOH, re-concentrate and treat the residue with EtOAc. Collect the solids via filtration and dry to afford the title compound (1.1 g, 40% yield). $^1$H NMR (400 MHz, DMSO-d$_6$): δ

8.05 (s, 3H), 2.87 (t, J=8.4 Hz, 2H), 1.90-1.86 (m, 2H), 0.96-0.93 (m, 2H), 0.82-0.81 (m, 2H).

Preparation 57

6-(5-Amino-4-fluoro-2-methylphenyl)-N,7-dimethylpyrido[2,3-d]pyrimidin-2-amine

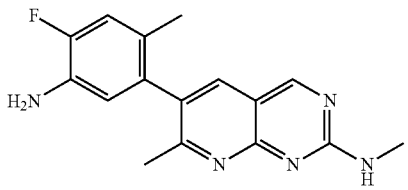 [SMILES: CNc1ncc2cc(-c3cc(N)c(F)cc3C)c(C)nc2n1]

Combine 7-methyl-2-(methylamino)pyrido[2,3-d]pyrimidin-6-yl trifluoromethanesulfonate (1.15 g, 3.57 mmol), 2-fluoro-4-methyl-5-(4,4,5,5-tetramethyl-1,3,2-dioxaborolan-2-yl)aniline (0.896 g, 3.57 mmol), and NaHCO$_3$ (0.899 g, 10.71 mmol) in dioxane (24 mL) and H$_2$O (6 mL), sparge with argon, treat with Pd(PPh$_3$)$_4$ (0.206 g, 0.178 mmol) and heat to 60° C. overnight. Add additional 7-methyl-2-(methylamino)pyrido[2,3-d]pyrimidin-6-yl trifluoromethanesulfonate (120 mg, 0.37 mmol) and Pd(PPh$_3$)$_4$ (80 mg, 0.07 mmol), sparge the mixture with argon, and heat at 60° C. overnight. Cool the mixture to RT, treat with brine and extract with EtOAc (3×). Wash the combined organics with brine, dry over Na$_2$SO$_4$, concentrate to dryness and purify via silica gel chromatography (50-100% EtOAc/Hexanes) to afford the title compound (940 mg, 89% yield). MS (m/z): 298.1 (M+1).

The following compound is prepared essentially by the method of Preparation 57.

| Prep No. | Chemical Name | Structure | Physical data MS (ESI) m/z: |
|---|---|---|---|
| 58 | Prop-1-en-2-yl (3,3-dimethylbutyl) carbamate | 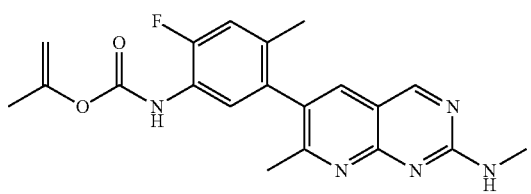 | 288.1 (M + 1) |

Preparation 59

Prop-1-en-2-yl (2-fluoro-4-methyl-5-(7-methyl-2-(methylamino)pyrido[2,3-d]pyrimidin-6-yl)phenyl) carbamate Treat a cooled solution (0° C.) of 6-(5-amino-4-fluoro-2-methylphenyl)-N,7-dimethylpyrido[2,3-d]pyrimidin-2-amine (0.85 g, 2.86 mmol) in pyridine (10 mL) dropwise with isopropenyl chloroformate (0.281 ml, 2.57 mmol) and stir the mixture for 20 min. at 0° C. Concentrate the mixture to dryness, dissolve the residue in DCM, wash with brine, dry over Na$_2$SO$_4$ and concentrate to dryness to afford the title compound. Use it without purification (assuming 100% yield). MS (m/z): 382.1 (M+1).

Preparation 60

6-(5-Amino-4-fluoro-2-methylphenyl)-N-(2-methoxyethyl)-7-methylpyrido[2,3-d]pyrimidin-2-amine

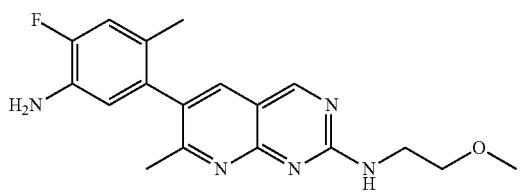 [SMILES: COCCNc1ncc2cc(-c3cc(N)c(F)cc3C)c(C)nc2n1]

Treat a solution of 2-fluoro-4-methyl-5-(7-methyl-2-(methylthio)pyrido[2,3-d]pyrimidin-6-yl)benzenamine (0.300 g, 0.954 mmol) in DMF (1 mL) with 2-methoxyethanamine (0.430 g, 5.73 mmol) in a screw-capped vial and heat at 100° C. for 20 h. Cool the mixture to RT, treat with H$_2$O and extract with EtOAc (2×). Wash the combined organics with brine, dry over Na$_2$SO$_4$ and concentrate to dryness to afford the title compound as a dark semi-solid (278 mg, 85% yield). MS (m/z): 342.2 (M+1).

Preparation 61

2-(2-Bromo-4-fluoro-5-nitrophenyl)acetic acid

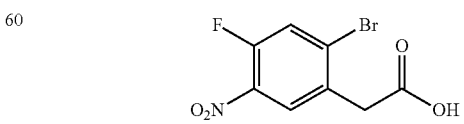

Add nitric acid (65%, 21.0 g, 0.22 mol) dropwise to a cooled mixture (−10° C.) of (2-bromo-4-fluorophenyl)acetic acid (50 g, 0.22 mol) in concentrated sulfuric acid (250 mL) and stir the resulting mixture at −10-0° C. for 20 min. Pour onto crushed ice, extract with EtOAc (3×200 mL), wash organics with brine (3×100 mL), dry over sodium sulfate, and concentrate in vacuo to give the title compound (50 g, 84% yield). $^1$H NMR (400 MHz, CDCl$_3$): δ 8.04 (d, J=7.6 Hz, 1H), 7.57 (d, J=9.0 Hz, 1H), 3.87 (s, 2H).

Preparation 62

1-(2-Bromo-4-fluoro-5-nitrophenyl)propan-2-one

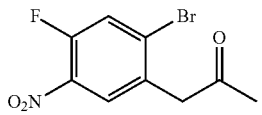

Treat a solution of 2-(2-bromo-4-fluoro-5-nitrophenyl) acetic acid (30.0 g, 0.11 mol) in acetic anhydride (30 mL) with 1-methylimidazole (4.5 g, 55 mmol), stir at RT for 2 h, treat with water, stir for 5 min, and extract with EtOAc. Wash the combined organics with water, saturated. Na$_2$CO$_3$, then brine, dry over Na$_2$SO$_4$, concentrate and purify via silica gel chromatography (EtOAc/petroleum ether) to afford the title compound (12 g, 40% yield). $^1$H NMR (400 MHz, DMSO-d$_6$): δ 8.19 (d, J=8.0 Hz, 1H), 8.02 (d, J=10.8 Hz, 1H), 4.09 (s, 2H), 2.23 (s, 3H).

Preparation 63

1-(5-Amino-2-bromo-4-fluorophenyl)propan-2-one

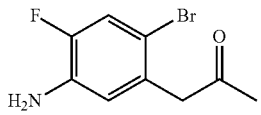

Treat a mixture of 1-(2-bromo-4-fluoro-5-nitrophenyl) propan-2-one (12 g, 43.6 mmol) in acetic acid (200 mL) with iron powder (24 g, 0.436 mol) and stir at 50° C. for 1 h. Add water and EtOAc, filter to remove solids, and extract the filtrate with EtOAc (2×). Wash the combined organics with saturated. Na$_2$CO$_3$, then brine, dry over Na$_2$SO$_4$ and concentrate to dryness to afford the title compound (10.2 g, 94% yield). $^1$H NMR (400 MHz, DMSO-d$_6$): δ 7.26 (d, J=10.8 Hz, 1H), 6.69 (d, J=9.6 Hz, 1H), 5.33 (s, 2H), 3.74 (s, 2H), 2.14 (s, 3H).

Preparation 64

4-Bromo-2-fluoro-5-(7-methyl-2-(methylthio)pyrido[2,3-d]pyrimidin-6-yl)aniline

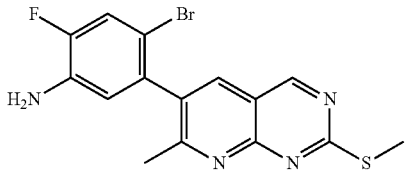 [SMILES: CSc1ncc2cc(-c3cc(N)c(F)cc3Br)c(C)nc2n1]

Treat a solution of 1-(5-amino-2-bromo-4-fluorophenyl) propan-2-one (5 g, 27.62 mmol) and 4-amino-2-methylsulfanyl-pyrimidine-5-carbaldehyde (4.67 g, 27.62 mmol) in EtOH (30 mL) with sodium ethoxide (3.76 g, 55.25 mmol) and stir at RT for 12 h. Concentrate the mixture to dryness, treat with water, extract with EtOAc (3×), wash the combined organics with brine, dry with Na$_2$SO$_4$, concentrate and purify by silica gel chromatography (EtOAc/Pet Ether, 1:4) to afford the title compound (1.7 g, 16% yield). MS (m/z): 379.1/381.1 (M+1).

Preparation 65

Isopropenyl N-[4-bromo-2-fluoro-5-(7-methyl-2-methylsulfanyl-pyrido[2,3-d]pyrimidin-6-yl)phenyl]carbamate

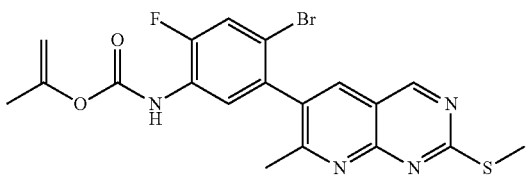 [SMILES: C=C(C)OC(=O)Nc1cc(-c2cc3cnc(SC)nc3nc2C)c(Br)cc1F]

Treat a mixture of 4-bromo-2-fluoro-5-(7-methyl-2-(methylthio)pyrido[2,3-d]pyrimidin-6-yl)aniline (0.20 g, 0.527 mmol) in EtOAc (10 mL) and saturated. NaHCO$_3$ (10 ml) with isopropenyl chloroformate (0.064 ml, 0.580 mmol) and stir the biphasic mixture vigorously at RT for 4 h. Separate the layers, extract the aqueous layer with additional EtOAc (1×), wash the combined organics with brine, dry over Na$_2$SO$_4$ and concentrate to dryness to afford the title compound (assume 100% yield). MS (m/z): 463.0.

Preparation 66

1-(4-Bromo-2-fluoro-5-(7-methyl-2-(methylthio)pyrido[2,3-d]pyrimidin-6-yl)phenyl)-3-(3,3-dimethylbutyl)urea

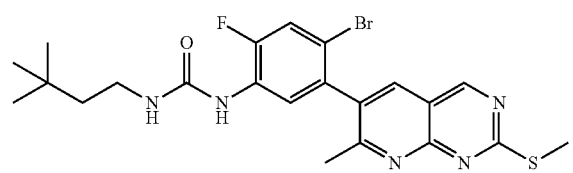 [SMILES: CSc1ncc2cc(-c3cc(NC(=O)NCCC(C)(C)C)c(F)cc3Br)c(C)nc2n1]

Treat a solution of 3,3-dimethylbutan-1-amine (0.080 g, 0.790 mmol) and prop-1-en-2-yl (4-bromo-2-fluoro-5-(7-methyl-2-(methylthio)pyrido[2,3-d]pyrimidin-6-yl)phenyl) carbamate (0.244 g, 0.527 mmol) in dioxane (5 mL) with 1-methylpyrrolidine (4.48 mg, 0.053 mmol), heat at 65° C. for 3 h, then cool to RT overnight. Collect the resulting solid via filtration; concentrate the filtrate to dryness and purify via silica gel chromatography (10-30% EtOAc/DCM). Combine the two solids to afford the title compound (260 mg, 97% yield). MS (m/z): 506.1/508.1 (M+1).

Preparation 67

6-Bromo-N-methylpyrido[2,3-d]pyrimidin-2-amine

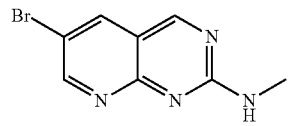

Treat a solution of 5-bromo-2-fluoropyridine-3-carboxaldehyde (0.50 g, 2.451 mmol) and 1-methylguanidine hydrochloride (0.322 g, 2.94 mmol) in acetonitrile (20 mL) with TEA (0.947 mL, 7.35 mmol) and heat to 180° C. in the microwave for 15 min. Concentrate the mixture to dryness, treat the residue with DCM and wash with H$_2$O, then brine. Dry the organic layer over Na$_2$SO$_4$, concentrate to dryness and purify via silica gel chromatography (20-100% EtOAc/Hexanes) to afford the title compound (140 mg, 24% yield). MS (m/z): 241.0 (M+1).

The following compound is prepared essentially by the method of Preparation 67.

| Prep No. | Chemical Name | Structure | Physical data MS (m/z) |
|---|---|---|---|
| 68 | 6-Bromo-N-[(4-methoxyphenyl)methyl]-N-methyl-pyrido[2,3-d]pyrimidin-2-amine | 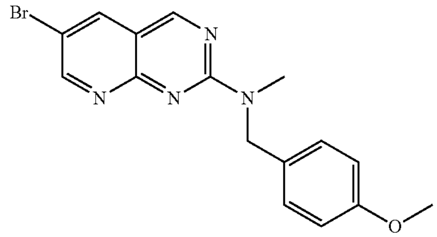 [SMILES: COc1ccc(CN(C)c2ncc3cc(Br)cnc3n2)cc1] | 359.0/361.0 (M + 1) |

Preparation 69 and 70

The following compounds are prepared essentially by the method of Preparation 49.

| Prep No. | Chemical Name | Structure | Physical data MS (m/z) |
|---|---|---|---|
| 69 | 6-(5-Amino-4-fluoro-2-methyl-phenyl)-N-methyl-pyrido[2,3-d]pyrimidin-2-amine | 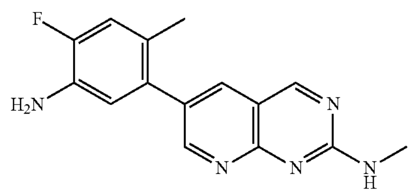 [SMILES: CNc1ncc2cc(-c3cc(N)c(F)cc3C)cnc2n1] | 284.2 (M + 1) |
| 70 | 6-(5-Amino-4-fluoro-2-methyl-phenyl)-N-[(4-methoxyphenyl)methyl]-N-methyl-pyrido[2,3-d]pyrimidin-2-amine | 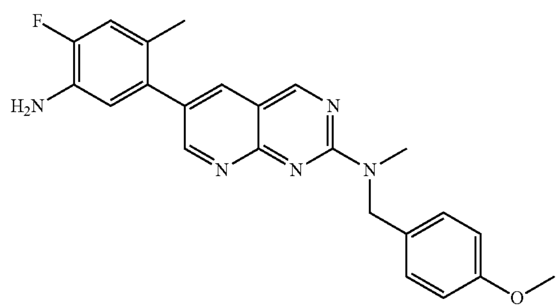 [SMILES: COc1ccc(CN(C)c2ncc3cc(-c4cc(N)c(F)cc4C)cnc3n2)cc1] | 404.2 (M + 1) |

Preparation 71 and 72

The following compounds are prepared essentially by the method of Preparation 50.

| Prep No. | Chemical Name | Structure | Physical data MS (m/z) |
|---|---|---|---|
| 71 | Isopropenyl N-[2-fluoro-4-methyl-5-(2-methylaminopyrido[2,3-d]pyrimidin-6-yl)phenyl]carbamate | 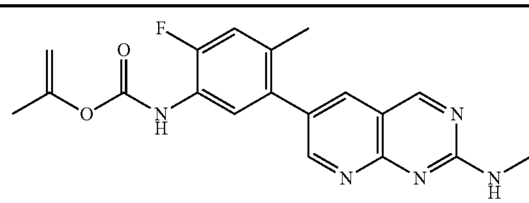 | 368.2 (M + 1) |

| Prep No. | Chemical Name | Structure | Physical data MS (m/z) |
|---|---|---|---|
| 72 | Isopropenyl N-[2-fluoro-5-[2-[(4-methoxyphenyl)methyl-methyl-amino]pyrido[2,3-d]pyrimidin-6-yl]-4-methyl-phenyl]carbamate | 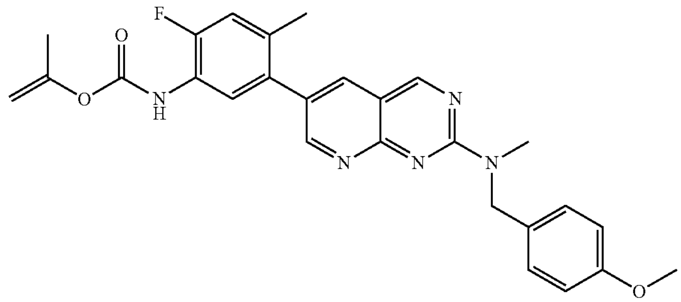 [SMILES: C=C(C)OC(=O)Nc1cc(-c2cnc3nc(N(C)Cc4ccc(OC)cc4)ncc3c2)c(C)cc1F] | 488.2 (M + 1) |

Preparation 73

1-(3,3-Dimethylbutyl)-3-[2-fluoro-5-[2-[(4-methoxyphenyl)methyl-methyl-amino]pyrido[2,3-d]pyrimidin-6-yl]-4-methyl-phenyl]urea

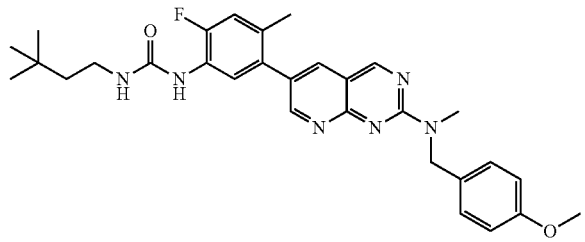 [SMILES: COc1ccc(CN(C)c2ncc3cc(-c4cc(NC(=O)NCCC(C)(C)C)c(F)cc4C)cnc3n2)cc1]

Preparation 73 is prepared essentially by the method of Preparation 51. MS (m/z): 530.6 (M+1).

EXAMPLE 1

1-(2,4-Difluoro-5-(7-methyl-2-(methylamino)pyrido[2,3-d]pyrimidin-6-yl)phenyl)-3-(3,3-dimethylbutyl)urea

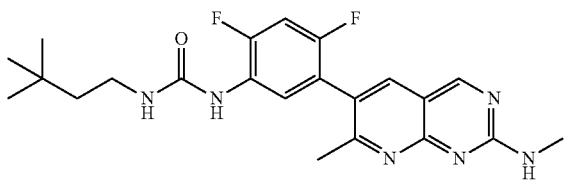 [SMILES: CNc1ncc2cc(-c3cc(NC(=O)NCCC(C)(C)C)c(F)cc3F)c(C)nc2n1]

Combine 1-(2,4-difluoro-5-(4,4,5,5-tetramethyl-1,3,2-dioxaborolan-2-yl)phenyl)-3-(3,3-dimethylbutyl)urea (3.90 g, 10.19 mmol), 6-bromo-N,7-dimethylpyrido[2,3-d]pyrimidin-2-amine (2.58 g, 10.19 mmol) and $K_2CO_3$ (4.23 g, 30.6 mmol) in dioxane (68 mL) and $H_2O$ (17 mL) and sparge with argon. Treat with tetrakis(triphenylphosphine)palladium (0.589 g, 0.510 mmol) and heat at 85° C. overnight. Cool the mixture to RT, dilute with EtOAc, filter through diatomaceous earth, and rinse well with EtOAc. Combine filtrates and wash with water (3×) and brine (1×), dry over $Na_2SO_4$, and concentrate to dryness. Treat the residue with acetonitrile and sonicate until solids precipitate. Heat the suspension at 80° C. for 2.5 h, cool to RT and collect the solids by filtration. Re-suspend solid in MeCN, heat at 80° C. for 1 h and collect by filtration. Concentrate filtrates to dryness and purify by silica gel chromatography (EtOAc/Hex, then EtOAc/MeOH/ $NH_4OH$). Treat the purified material with MeCN, sonicate, collect solids via filtration, rinsed with MeCN and dry in vacuo. Combine the crops of solids to provide title compound (2.05 g, 47%) as a pale tan solid. MS (ESI) m/z: 429.2 ($M+H^+$).

The following compounds are prepared essentially by the procedure of Example 1

| Ex | Chemical Name | Structure | Physical data MS (m/z): |
|---|---|---|---|
| 2 | 1-(3,3-Dimethylbutyl)-3-(2-fluoro-5-(7-methyl-2-(methylamino)pyrido[2,3-d]pyrimidin-6-yl)phenyl)urea | 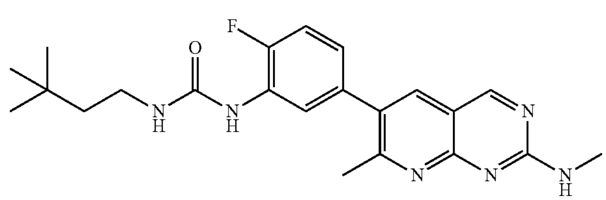 [SMILES: CNc1ncc2cc(-c3ccc(F)c(NC(=O)NCCC(C)(C)C)c3)c(C)nc2n1] | 411.2 (M + 1) |

| Ex | Chemical Name | Structure | Physical data MS (m/z): |
|---|---|---|---|
| 3 | 1-(3-Cyano-3-methylbutyl)-3-(2-fluoro-4-methyl-5-(7-methyl-2-(methylamino)pyrido[2,3-d]pyrimidin-6-yl)phenyl)urea | 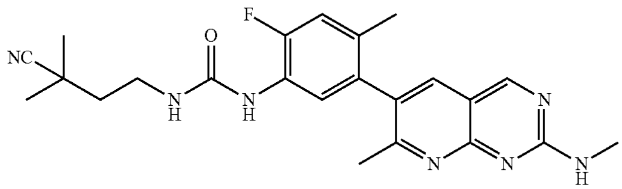 [SMILES: CNc1ncc2cc(-c3cc(NC(=O)NCCC(C)(C)C#N)c(F)cc3C)c(C)nc2n1] | 436.2 (M + 1) |
| 4 | 1-(3-Fluoro-3-methylbutyl)-3-(2-fluoro-4-methyl-5-(7-methyl-2-(methylamino)pyrido[2,3-d]pyrimidin-6-yl)phenyl)urea | 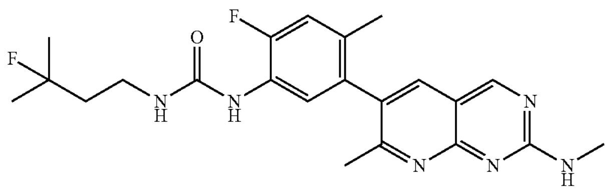 [SMILES: CNc1ncc2cc(-c3cc(NC(=O)NCCC(C)(C)F)c(F)cc3C)c(C)nc2n1] | 429.2 (M + 1) |
| 5 | 1-(3,3-Dimethylbutyl)-3-(2-fluoro-5-(2-((2-methoxyethyl)amino)-7-methylpyrido[2,3-d]pyrimidin-6-yl)-4-methylphenyl)urea | 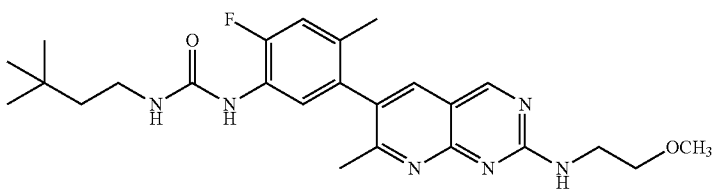 [SMILES: COCCNc1ncc2cc(-c3cc(NC(=O)NCCC(C)(C)C)c(F)cc3C)c(C)nc2n1] | 469.3 (M + 1) |
| 6 | 1-(3,3-Dimethylcyclobutyl)-3-(2-fluoro-4-methyl-5-(7-methyl-2-(methylamino)pyrido[2,3-d]pyrimidin-6-yl)phenyl)urea | 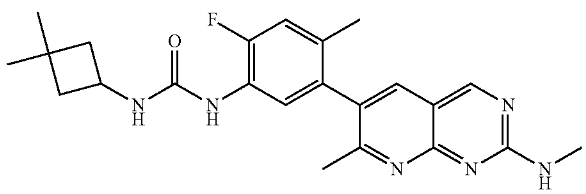 | 423.2 (M + 1) |
| 7 | 1-(2,4-Difluoro-5-(7-methyl-2-(methylamino)pyrido[2,3-d]pyrimidin-6-yl)phenyl)-3-(3,3-dimethylcyclobutyl)urea | 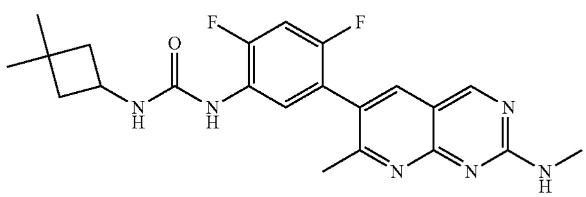 | 427.2 (M + 1) |
| 8 | 1-[2-Fluoro-4-methyl-5-(2-methylaminopyrido[2,3-d]pyrimidin-6-yl)phenyl]-3-(2-hydroxy-3,3-dimethyl-butyl)urea | 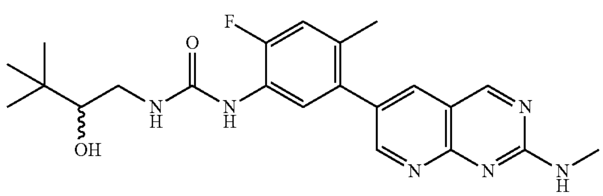 [SMILES: CNc1ncc2cc(-c3cc(NC(=O)NCC(O)C(C)(C)C)c(F)cc3C)cnc2n1] | 426.8 (M + 1) |
| 9 | 1-[(2,2-Dimethylcyclopropyl)methyl]-3-[2-fluoro-4-methyl-5-methylaminopyrido[2,3-d]pyrimidin-6-yl)phenyl]urea | 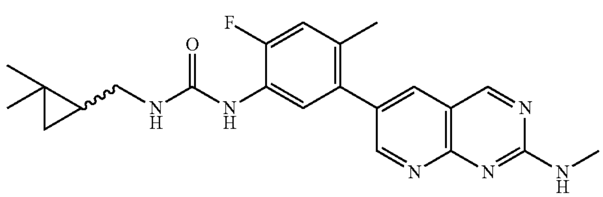 | 408.8 (M + 1) |
| 10 | 1-[5-(2-Amino-7-methyl-pyrido[2,3-d]pyrimidin-6-yl)-2-fluoro-4-methyl-phenyl]-3-2-hydroxy-3,3-dimethyl-butyl)urea | 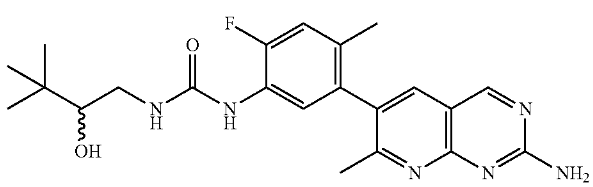 [SMILES: Cc1cc(F)c(NC(=O)NCC(O)C(C)(C)C)cc1-c1cc2cnc(N)nc2nc1C] | 426.8 (M + 1) |

| Ex | Chemical Name | Structure | Physical data MS (m/z): |
|---|---|---|---|
| 11 | 1-[2,4-Difluoro-5-(7-methyl-2-methylamino-pyrido[2,3-d]pyrimidin-6-yl)phenyl]-3-(2-hydroxy-3,3-dimethyl-butyl)urea | 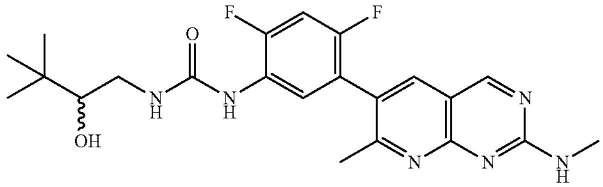 [SMILES: CNc1ncc2cc(-c3cc(NC(=O)NCC(O)C(C)(C)C)c(F)cc3F)c(C)nc2n1] | 445.0 (M + 1) |
| 12 | 1-(3-Cyano-3-methylbutyl)-3-(2,4-difluoro-5-(7-methyl-2-(methylamino)pyrido[2,3-d]pyrimidin-6-yl)phenyl)urea | 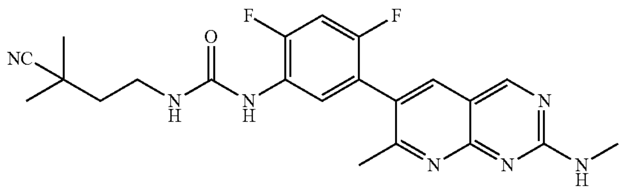 [SMILES: CNc1ncc2cc(-c3cc(NC(=O)NCCC(C)(C)C#N)c(F)cc3F)c(C)nc2n1] | 440.2 (M + 1) |
| 13 | 1-(3-Cyano-3-methylbutyl)-3-(2-fluoro-5-(7-methyl-2-(methylamino)pyrido[2,3-d]pyrimidin-6-yl)phenyl)urea | 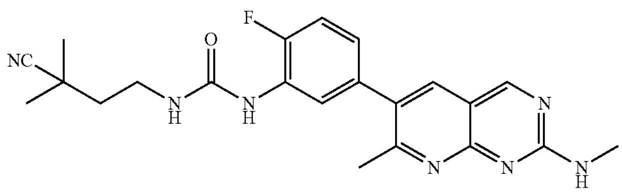 [SMILES: CNc1ncc2cc(-c3ccc(F)c(NC(=O)NCCC(C)(C)C#N)c3)c(C)nc2n1] | 422.1 (M + 1 |

EXAMPLE 14

1-(2-Fluoro-4-methyl-5-(7-methyl-2-(methylamino)pyrido[2,3-d]pyrimidin-6-yl)phenyl)-3-(3-methoxy-3-methylbutyl)urea

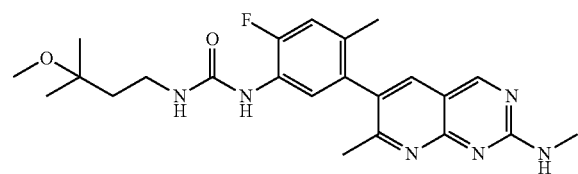

Combine 1-(2-fluoro-4-methyl-5-(4,4,5,5-tetramethyl-1,3,2-dioxaborolan-2-yl)phenyl)-3-(3-methoxy-3-methylbutyl)urea (0.17 g, 0.431 mmol), 7-methyl-2-(methylamino)pyrido[2,3-d]pyrimidin-6-yl trifluoromethanesulfonate (0.139 g, 0.431 mmol) and NaHCO₃ (0.109 g, 1.293 mmol) in dioxane (6 mL) and H₂O (1.5 mL). Sparge the mixture with argon. Treat with tetrakis(triphenylphosphine)palladium (0.025 g, 0.022 mmol), sparge again with argon and heat at 55° C. overnight. Add an additional portion of tetrakis(triphenylphosphine)palladium (25 mg, 0.022 mmol) and heat at 65° C. overnight. Cool the mixture to RT, remove solids by filtration, and wash solids with dioxane. Combine filtrates, dilute with EtOAc, wash with saturated NaHCO₃ and brine, dry over Na₂SO₄, concentrate to dryness and purify via silica gel chromatography (EtOAc/Hex). Dissolve in DCM, wash with saturated NaHCO₃ and brine, dry over Na₂SO₄, concentrate to dryness. Treat with 1:1 MeCN/H₂O, freeze in −78° C. bath and lyophilize to obtain the title compound (40 mg, 21% yield) as a pale yellow solid. MS (ESI) m/z: 441.2 (M+1).

The following compounds are prepared essentially by the procedure of Example 14

| Ex | Chemical Name | Structure | Physical data MS (m/z): |
|---|---|---|---|
| 15 | 1-[2-Fluoro-4-methyl-5-(7-methyl-2-methylamino-pyrido[2,3-d]pyrimidin-6-yl)phenyl]-3-(2-hydroxy-3,3-dimethyl-butyl)urea | 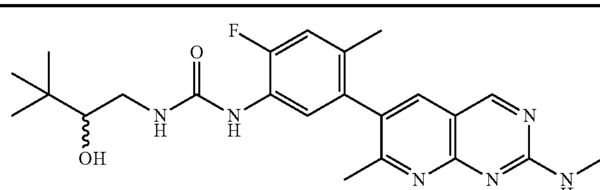 | 440.8 (M + 1) |

| Ex | Chemical Name | Structure | Physical data MS (m/z): |
|---|---|---|---|
| 16 | 1-(3,3-Dimethylbutyl)-3-[2-fluoro-5-[2-(2-hydroxyethylamino)-7-methyl-pyrido[2,3-d]pyrimidin-6-yl]-4-methyl-phenyl]urea | 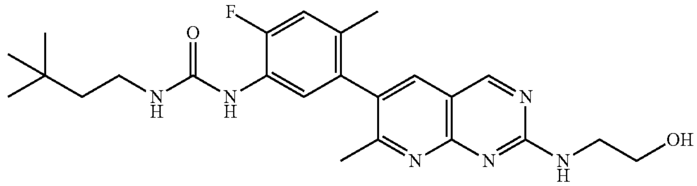 [SMILES: Cc1cc(F)c(NC(=O)NCCC(C)(C)C)cc1-c1cc2cnc(NCCO)nc2nc1C] | 454.8 (M + 1) |
| 17 | 1-[5-[2-(2-Dimethylaminoethylamino)-7-methyl-pyrido[2,3-d]pyrimidin-6-yl]-2-fluoro-4-methyl-phenyl]-3-(3,3-dimethylbutyl)urea | 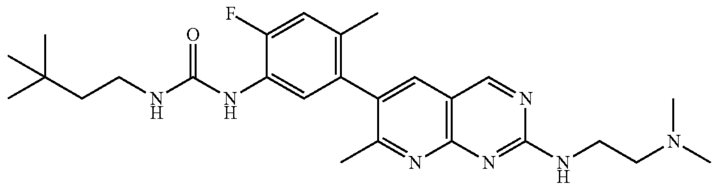 [SMILES: Cc1cc(F)c(NC(=O)NCCC(C)(C)C)cc1-c1cc2cnc(NCCN(C)C)nc2nc1C] | 482.0 (M + 1) |

EXAMPLE 18

1-[2-Fluoro-4-methyl-5-(2-methylaminopyrido[2,3-d]pyrimidin-6-yl)phenyl]-3-[(2R)-2-hydroxy-3,3-dimethyl-butyl]urea Purify 1-[2-fluoro-4-methyl-5-(2-methylaminopyrido[2,3-d]pyrimidin-6-yl)phenyl]-3-(2-hydroxy-3,3-dimethyl-butyl)urea (100 mg) on a Chiralpak AS-H column eluting with 40% MeOH(0.2% IPA)/CO$_2$ to obtain separated isomer. Elute through an SCX column eluting with MeOH/MeOH (NH$_3$). Dissolve residue in 20% IPA/CHCl$_3$, wash with saturated. Aqueous NaHCO$_3$ solution, dried over MgSO$_4$, filtered and concentrated to obtain the title compound (16 mg, 16%). MS (m/z): 427.2 (M+1).

The following compound is prepared essentially by the procedure of Example 18.

EXAMPLE 20

1-(5-(2-Amino-7-methylpyrido[2,3-d]pyrimidin-6-yl)-2-fluoro-4-methylphenyl)-3-(3,3-dimethylbutyl)urea Treat a suspension of 1-(3,3-dimethylbutyl)-3-(2-fluoro-4-methyl-5-(7-methyl-2-(methylthio)pyrido[2,3-d]pyrimidin-6-yl)phenyl)urea (0.248 g, 0.562 mmol) in DCM (20 mL) with 70 wt % mCPBA (0.208 g, 0.842 mmol) and stir the mixture at RT for 2 h. Add ammonia (0.5N in dioxane, 8.99 mL, 4.49 mmol) and stir the mixture at RT overnight. Add additional ammonia (7N in MeOH, 5 mL, 35 mmol) and stir at RT overnight. Concentrate the mixture to dryness, treat with saturated. Na$_2$CO$_3$ and extract with DCM (4×). Dry the combined organics over MgSO$_4$, concentrate to dryness and purify via silica gel chromatography (50-100% EtOAc/Hex,

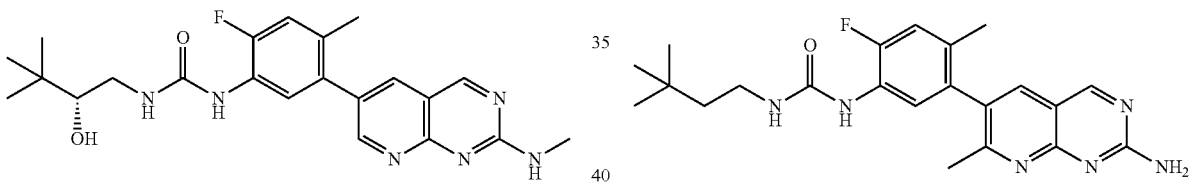

| Ex No. | Chemical Name | Structure | | Physical data MS (ESI) m/z: |
|---|---|---|---|---|
| 19 | 1-[2-fluoro-4-methyl-5-(2-methylaminopyrido[2,3-d]pyrimidin-6-yl)phenyl]-3-[(2S)-2-hydroxy-3,3-dimethyl-butyl]urea | | Chiral | 427.2 (M + 1) | then 0-10% MeOH/EtOAc) to afford the title compound as an off-white solid (57 mg, 24%). MS (m/z): 411.2 (M+1).

The following compounds are prepared essentially by the method of Example 20.

| Ex | Chemical Name | Structure | Physical data MS (m/z): |
|---|---|---|---|
| 21 | 1-(3,3-Dimethylbutyl)-3-(2-fluoro-4-methyl-5-(7-methyl-2-((2-morpholinoethyl)amino)pyrido[2,3-d]pyrimidin-6-yl)phenyl)ure | 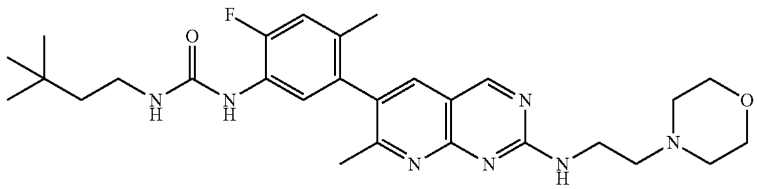 [SMILES: Cc1cc(F)c(NC(=O)NCCC(C)(C)C)cc1-c1cc2cnc(NCCN3CCOCC3)nc2nc1C] | 524.3 (M + 1) |
| 22 | 1-(3,3-Dimethylbutyl)-3-(2-fluoro-4-methyl-5-(7-methyl-2-(((1-methyl-1H-imidazol-4-yl)methyl)amino)pyrido[2,3-d]pyrimidin-6-yl)phenyl)urea | 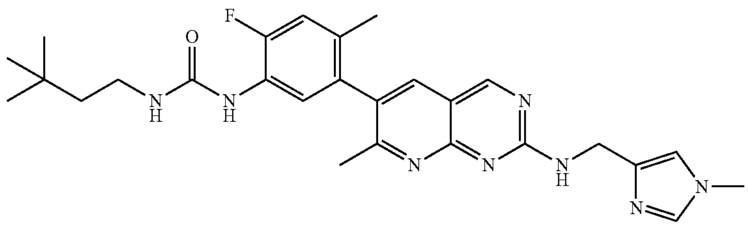 [SMILES: Cc1cc(F)c(NC(=O)NCCC(C)(C)C)cc1-c1cc2cnc(NCc3cn(C)cn3)nc2nc1C] | 505.3 (M + 1) |
| 23 | 1-(5-(2-Amino-7-methylpyrido[2,3-d]pyrimidin-6-yl)-2-fluoro-4-methylphenyl)-3-(2-(1-methylcyclopropyl)ethyl)urea | 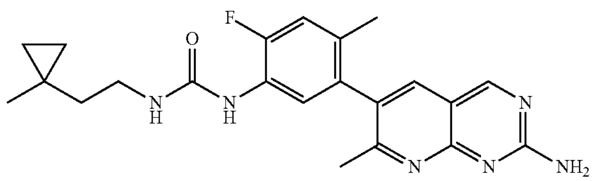 [SMILES: Cc1cc(F)c(NC(=O)NCCC2(C)CC2)cc1-c1cc2cnc(N)nc2nc1C] | 409.2 (M + 1) |
| 24 | 1-(2-Fluoro-4-methyl-5-(7-methyl-2-(methylamino)pyrido[2,3-d]pyrimidin-6-yl)phenyl)-3-(2-(1-methylcyclopropyl)ethyl)urea | 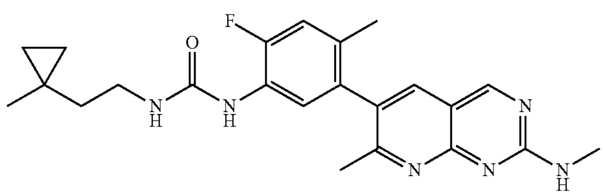 | 423.2 (M + 1) |
| 25 | 1-(3-Fluoro-3-methylbutyl)-3-(2-fluoro-4-methyl-5-(7-methyl-2-(oxetan-3-ylamino)pyrido[2,3-d]pyrimidin-6-yl)phenyl)urea | 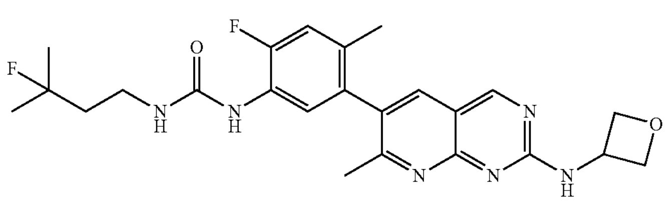 [SMILES: Cc1cc(F)c(NC(=O)NCCC(C)(C)F)cc1-c1cc2cnc(NC3COC3)nc2nc1C] | 471.2 (M + 1) |
| 26 | 1-(5-(2-(Ethylamino)-7-methylpyrido[2,3-d]pyrimidin-6-yl)-2-fluoro-4-methylphenyl)-3-(3-fluoro-3-methylbutyl)urea | 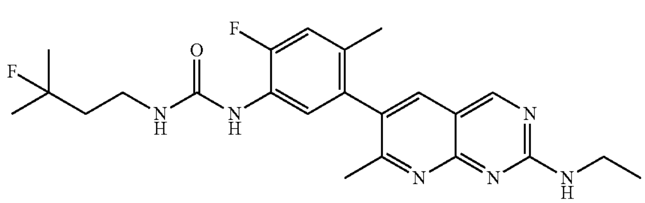 [SMILES: CCNc1ncc2cc(-c3cc(NC(=O)NCCC(C)(C)F)c(F)cc3C)c(C)nc2n1] | 443.2 (M + 1) |
| 27 | 1-(2-Fluoro-4-methyl-5-(7-methyl-2-(methylamino)pyrido[2,3-d]pyrimidin-6-yl)phenyl)-3-(4,4,4-trifluoro-3,3-dimethylbutyl)urea | 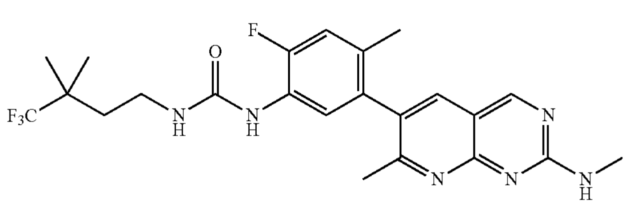 [SMILES: CNc1ncc2cc(-c3cc(NC(=O)NCCC(C)(C)C(F)(F)F)c(F)cc3C)c(C)nc2n1] | 479.2 (M + 1) |

| Ex | Chemical Name | Structure | Physical data MS (m/z): |
|----|---------------|-----------|-------------------------|
| 28 | 1-(5-(2-Amino-7-methylpyrido[2,3-d]pyrimidin-6-yl)-2-fluoro-4-methylphenyl)-3-(3-fluoro-3-methylbutyl)urea | 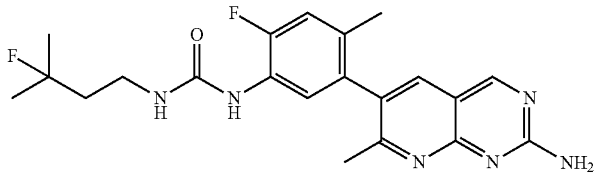 [SMILES: Cc1cc(F)c(NC(=O)NCCC(C)(C)F)cc1-c1cc2cnc(N)nc2nc1C] | 415.2 (M + 1) |
| 29 | 1-(3-Fluoro-3-methylbutyl)-3-(2-fluoro-5-(2-((2-hydroxyethyl)amino)-7-methylpyrido[2,3-d]pyrimidin-6-yl)-4-methylphenyl)urea | 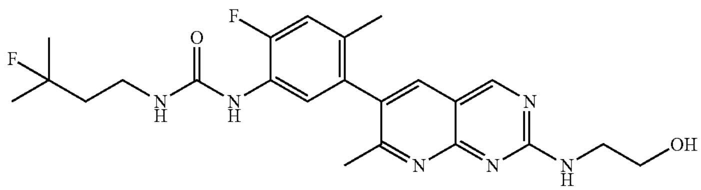 [SMILES: Cc1cc(F)c(NC(=O)NCCC(C)(C)F)cc1-c1cc2cnc(NCCO)nc2nc1C] | 459.2 (M + 1) |

EXAMPLE 30

1-(2-Fluoro-4-methyl-5-(7-methyl-2-(methylamino)pyrido[2,3-d]pyrimidin-6-yl)phenyl)-3-(2-(1-(trifluoromethyl)cyclopropyl)ethyl)urea

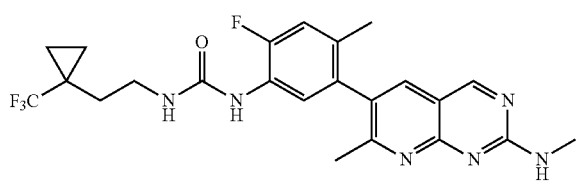 [SMILES: CNc1ncc2cc(-c3cc(NC(=O)NCCC4(C(F)(F)F)CC4)c(F)cc3C)c(C)nc2n1]

Treat a mixture of prop-1-en-2-yl(2-fluoro-4-methyl-5-(7-methyl-2-(methylamino)pyrido[2,3-d]pyrimidin-6-yl)phenyl)carbamate (1.09 g, 2.86 mmol) and 2-(1-(trifluoromethyl)cyclopropyl)ethanamine hydrochloride (0.542 g, 2.86 mmol) in THF (30 mL) with 1-methylpyrrolidine (1.52 mL, 14.3 mmol) and heat at 65° C. for 4 h. Cool the mixture to RT, dilute with EtOAc, wash with brine (2×), dry over MgSO₄, concentrate to dryness and purify via silica gel chromatography (MeOH/EtOAc). Treat the resulting material with acetonitrile, cool to −20° C. for 2 h, collect the solids via filtration, rinse with acetonittrile (−20° C.) and dry to afford the title compound as a pale yellow solid (570 mg, 42% yield). MS (m/z): 477.2 (M+1).

EXAMPLE 31

1-(3,3-Dimethylcyclobutyl)-3-(2-fluoro-5-(2-((2-methoxyethyl)amino)-7-methylpyrido[2,3-d]pyrimidin-6-yl)-4-methylphenyl)urea

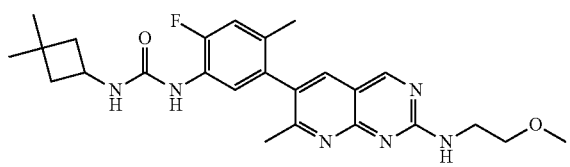

Treat a solution of 6-(5-amino-4-fluoro-2-methylphenyl)-N-(2-methoxyethyl)-7-methylpyrido[2,3-d]pyrimidin-2-amine (0.270 g, 0.791 mmol) in dioxane (5 mL) with 3,3-dimethylcyclobutane carboxylic acid (0.122 g, 0.949 mmol) followed by DPPA (0.261 g, 0.949 mmol) and TEA (0.160 g, 1.582 mmol), stir at RT for 20 minutes, heat to 90° C. for 2 h and then cool to RT overnight. Concentrate the mixture to dryness, purify via silica gel chromatography (20-100% EtOAc/Hexanes) and triturate with MeCN. Collect the resulting material via filtration and re-purify via silica gel chromatography (20-100% EtOAc/Hexanes) to afford the title compound as a yellow solid (55 mg, 13% yield). MS (m/z): 467.3 (M+1).

EXAMPLE 32

1-(4-Bromo-2-fluoro-5-(7-methyl-2-(methylamino)pyrido[2,3-d]pyrimidin-6-yl)phenyl)-3-(3,3-dimethylbutyl)urea

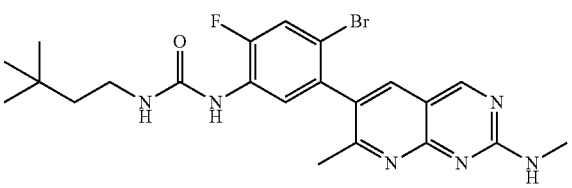

Add mCPBA (0.152 g, 0.616 mmol) portion wise to a solution of 1-(4-bromo-2-fluoro-5-(7-methyl-2-(methylthio)pyrido[2,3-d]pyrimidin-6-yl)phenyl)-3-(3,3-dimethylbutyl)urea (0.26 g, 0.513 mmol) in DCM (10 mL) and stir at RT for 2 h. Add methylamine in THF (2.0M, 1.027 mL, 2.054 mmol) and stir at RT overnight. Add water, extract with DCM (3×), wash the combined organics with saturated. NaHCO₃, then brine, dry over MgSO₄, concentrate to dryness and purify via reverse-phase chromatography (MeCN/H₂O with 0.1% TFA). Combine fractions, remove the organics under reduced pressure and neutralize the resulting aqueous residue with NaHCO₃. Extract the mixture with EtOAc (2×), wash the combined organics with saturated. NaHCO₃, then brine, dry over Na₂SO₄, concentrate to dryness, treat with 1:1 MeCN/

H₂O, freeze and lyophilize to afford the title compound as a pale yellow solid (34 mg, 13% yield). MS (m/z): 489.1 (M+1)/491.1 (M+3).

EXAMPLE 33

N-(6-(5-(3-(3,3-Dimethylbutyl)ureido)-4-fluoro-2-methylphenyl)-7-methylpyrido[2,3-d]pyrimidin-2-yl)acetamide

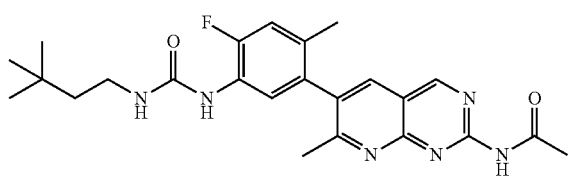 [SMILES: CC(=O)Nc1ncc2cc(-c3cc(NC(=O)NCCC(C)(C)C)c(F)cc3C)c(C)nc2n1]

Treat a cooled solution (0° C.) of 1-(5-(2-amino-7-methylpyrido[2,3-d]pyrimidin-6-yl)-2-fluoro-4-methylphenyl)-3-(3,3-dimethylbutyl)urea (0.167 g, 0.407 mmol) and catalytic dimethylaminopyridine (0.005 g, 0.041 mmol) in pyridine (4 mL) with acetic anhydride (0.269 ml, 2.85 mmol) and stir at RT overnight. Add saturated. Na₂CO₃ and MeOH and heat at 45° C. overnight. Treat the mixture with water, extract with 4:1 EtOAc/THF (3×), wash the combined organics with saturated. Na₂CO₃, then brine, dry over MgSO₄, concentrate to dryness and purify via silica gel chromatography (15-100% EtOAc/Hexanes). Dissolve the resulting material in acetonitrile/H₂O, freeze and lyophilize to afford the title compound as an off-white solid (55 mg, 30% yield). MS (m/z): 453.2 (M+1).

EXAMPLE 34

1-(3-Fluoro-3-methyl-butyl)-3-[2-fluoro-4-methyl-5-(2-methylaminopyrido[2,3-d]pyrimidin-6-yl)phenyl]urea

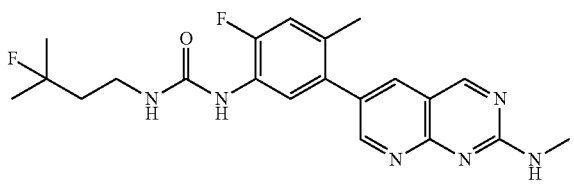 [SMILES: CNc1ncc2cc(-c3cc(NC(=O)NCCC(C)(C)F)c(F)cc3C)cnc2n1]

Add 3-fluoro-3-methyl-butan-1-amine hydrochloride (88 mg, 0.62 mmol) followed by N-methylpyrrolidine (0.065 mL, 0.62 mmol) to a stirred solution of isopropenyl N-[2-fluoro-4-methyl-5-(2-methylaminopyrido[2,3-d]pyrimidin-6-yl)phenyl]carbamate (184 mg, 0.50 mmol) in 1,4-dioxane (5 mL) and heat at 80° C. under N₂ overnight. Concentrate and purify on silica eluting with 0-5% MeOH (2N NH₃)/ DCM. Purify on SCX column eluting with NH₃/MeOH to obtain the title compound (219 mg, 70%). MS (m/z): 414.8 (M+1).

EXAMPLE 35

1-(3,3-Dimethylbutyl)-3-[2-fluoro-4-methyl-5-(2-methylaminopyrido[2,3-d]pyrimidin-6-yl)phenyl]urea

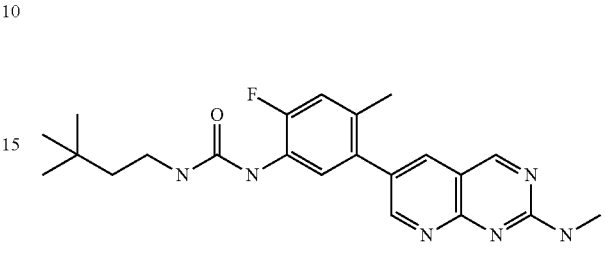

Add ice cold trifluoroacetic acid (100 mL, 1.32 mol) to a N₂ flushed vessel containing 1-(3,3-dimethylbutyl)-3-[2-fluoro-5-[2-[(4-methoxyphenyl)methyl-methyl-amino]pyrido[2,3-d]pyrimidin-6-yl]-4-methyl-phenyl]urea (22.4 g, 42.2 mmol) cap and allow to warm to RT overnight. Concentrate, dilute with CHCl₃ and basify to pH 8-9 with saturated NaHCO₃ solution. Extract with 20% IPA/CHCl₃ (3×), dry over MgSO₄, filter and concentrate. Purify on silica eluting with 0-5% MeOH (2N NH₃)/DCM to obtain the title compound (23.7 g, 81%). MS (m/z): 411.2 (M+1).

EXAMPLE 36

1-(2,4-Difluoro-5-(2-(methylamino)pyrido[2,3-d]pyrimidin-6-yl)phenyl)-3-(3,3-dimethylbutyl)urea methanesulfonate

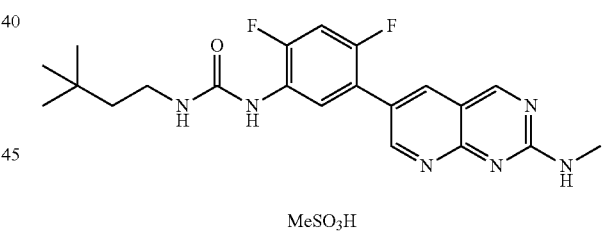

Treat a solution of prop-1-en-2-yl (3,3-dimethylbutyl)carbamate (0.039 g, 0.209 mmol) and 6-(5-amino-2,4-difluorophenyl)-N-methylpyrido[2,3-d]pyrimidin-2-amine (0.060 g, 0.209 mmol) in dioxane (5 mL) with catalytic 1-methylpyrrolidine (1.8 mg, 0.021 mmol) and heat at 65° C. overnight. Add 2,3,4,6,7,8,9,10-Octahydropyrimidol[1,2-a]azepine (0.1 mL) and additional prop-1-en-2-yl (3,3-dimethylbutyl) (25 mg, 0.135 mmol) and heat the mixture at 85° C. overnight. Add additional 2,3,4,6,7,8,9,10-Octahydropyrimidol[1,2-a]azepine (0.1 mL) and prop-1-en-2-yl (3,3-dimethylbutyl) (25 mg, 0.135 mmol) and heat the mixture at 85° C. for another 24 h. Cool the mixture to RT, concentrate to dryness and purify via silica gel chromatography (EtOAc/Hexane). Treat the resulting material with DCM, allow to stand at RT overnight, and collect the solid via filtration to afford 1-(2,4-difluoro-5-(2-(methylamino)pyrido[2,3-d]pyrimidin-6-yl)phenyl)-3-(3,3-dimethylbutyl)urea (30 mg, 35% yield). MS (m/z): 415.2 (M+1).

Treat a solution of 1-(2,4-difluoro-5-(2-(methylamino)pyrido[2,3-d]pyrimidin-6-yl)phenyl)-3-(3,3-dimethylbutyl) urea (0.030 g, 0.072 mmol) in hot MeOH (5 mL) with methanesulfonic acid (0.072 mL, 0.072 mmol) and cool to RT. Concentrate the mixture to dryness, treat with 1:1 MeCN/$H_2O$ (4 mL), freeze and lyophilize to afford the title compound as a pale yellow solid (68 mg, 178%, excess $MeSO_3H$). MS (m/z): 415.2 (M+1).

It is generally known that bioavailability of a poorly soluble compound may be enhanced, for example, by formulating it as a solid dispersion in a polymer matrix. Such solid dispersions are dispersions of drug in an inert carrier matrix prepared by melting (fusion) of drug-polymer mixtures followed by solidification of the homogeneous molten mixture by rapid cooling (for example using processes such as hot melt extrusion), or by dissolving the drug and polymer in appropriate organic solvent followed by either solvent removal by evaporation (for example spray-drying) or by precipitation using antisolvent. Solid dispersions typically render the drug in an amorphous form which results in faster dissolution rate and/or higher degree (extent) and duration of supersaturation leading to enhanced oral bioavailability of poorly soluble compounds relative to the undispersed crystalline drug. Polymers that have been successfully used for solid dispersions include (but are not limited to) polyvinyl pyrrolidone (PVP), polyvinyl pyrrolidone-vinyl acetate (PVP-VA), hydroxypropyl methylcellulose (HPMC), hydroxypropyl methylcellulose acetate succinate (HPMCAS), hydroxypropyl methylcellulose phthalate (HPMCP-55), cellulose acetate phthalate (CAP), and Eudragit® EPO.

Physical and chemical stability of a solid dispersion are factors in the suitability of such formulations. Drug loading is another variable that can impact physical stability of the metastable amorphous form of drug as well as its in vivo performance. A preferred way to administer a solid dispersion in humans is by further formulating it as a capsule, a tablet, or other solid oral dosage form by adding a pharmaceutically acceptable carrier, and optionally other excipients, suitable for such dosage form manufacturing and performance. Solid Dispersions may be dosed by filling the powder or granulated blend into capsules, as a suspension in suitable vehicle, or any other suitable oral pharmaceutical dosage form such as (but not limited to) tablets, sachets, granules, sprinkles, etc.

Cancer is increasingly recognized as a heterogeneous collection of diseases whose initiation and progression are induced by the aberrant function of one or more genes that regulate DNA repair, genome stability, cell proliferation, cell death, adhesion, angiogenesis, invasion, and metastasis in cell and tissue microenvironments. Variant or aberrant function of the "cancer" genes may result from naturally occurring DNA polymorphism, changes in genome copy number (through amplification, deletion, chromosome loss, or duplication), changes in gene and chromosome structure (through chromosomal translocation, inversion, or other rearrangement that leads to deregulated gene expression), and point mutations. Cancerous neoplasms may be induced by one aberrant gene function, and maintained by the same aberrant gene function, or maintenance and progression exacerbated by additional aberrant gene functions.

Beyond the genetic chromosomal aberrations mentioned above, each of the cancers may also include epigenetic modifications of the genome including DNA methylation, genomic imprinting, and histone modification by acetylation, methylation, or phosphorylation. An epigenetic modification may play a role in the induction and/or maintenance of the malignancy.

Extensive catalogues of the cytogenetic aberrations in human cancer have been compiled and are maintained and regularly updated online (see The Mitelman Database of Chromosome Aberrations in Cancer at the US National Cancer Institute (NCI) Cancer Genome Anatomy Project (CGAP) Web site: http://cgap.nci.nih.gov). The database includes chromosomal aberrations for at least some of the malignancies of the present invention. The Wellcome Trust Sanger Institute Cancer Genome Project maintains a detailed online "Cancer Gene Census" of all human genes that have been causally linked to tumorigenesis (see http://www.sanger.ac.uk/genetics/CGP/Census) as well as the COSMIC (Catalogue of Somatic Mutations in Cancer) database of somatic mutations in human cancer (see http://www.sanger.ac.uk/genetics/CGP/cosmic). A further source containing abundant information on cytogenetic changes causally linked to various cancers is the Atlas of Genetics and Cytogenetics in Oncology and Haematology (http://atlasgeneticsoncology.org//Anomalies/Anomliste.html#MDS). These databases also include chromosomal aberrations for at least some of the malignancies of the present invention.

Diagnosis of cancerous malignancies by biopsy, immunophenotyping and other tests are known and routinely used. In addition to high resolution chromosome banding and advanced chromosomal imaging technologies, chromosome aberrations in suspected cases of cancer can be determined through cytogenetic analysis such as fluorescence in situ hybridization (FISH), karyotyping, spectral karyotyping (SKY), multiplex FISH (M-FISH), comparative genomic hybridization (CGH), single nucleotide polymorphism arrays (SNP Chips) and other diagnostic and analysis tests known and used by those skilled in the art.

The Ras/Raf/MEK/MAPK signaling pathway relays extracellular stimuli to the nucleus, thereby regulating diverse cellular responses including cell proliferation, differentiation and apoptosis. Perturbation of these processes by aberrant MAPK signaling such as genetic alterations often leads to malignant transformation. The importance of this signaling pathway in neoplasms is evident through the discovery of many mutant alleles that activate this pathway in a variety of human malignancies. Oncogenic mutations in receptor tyrosine kinases (RTKs), such as EGFR and cMet, or overexpression of RTKs and their ligands abnormally activate Ras and its downstream components. Activating Ras mutations have been detected in approximately 30% of human cancers. These mutations markedly diminish GTPase activity, thereby rendering Ras in the GTP-bound and active state. In mammals, the Ras family consists of three genes: K-Ras, N-Ras and H-Ras. K-Ras is often mutated in epithelial cancers, such as pancreatic, lung and colorectal cancer, while N-Ras mutations often occur in melanoma, liver and myeloid (AML, CML) malignancies. Activating mutations of B-Raf, a member of Raf family, have been discovered with high frequency in melanoma and thyroid carcinoma and, to a lesser extent, in colorectal, ovarian and lung cancer. Somatic mutations of MEK1 and MEK2 have been identified in melanoma patients. Finally, loss of negative regulators, such as members of the Sprouty family and GAPs (GTPase-activating proteins) such as NF1, can indirectly activate this pathway. It is believed that many tumors exhibit deregulation of Ras/Raf/MEK/MAPK pathway, making it an attractive target for therapeutic intervention.

The Raf proteins are composed of three members, A-Raf, B-Raf and C-Raf (also called Raf1), that play a pivotal role in transducing signals from Ras to downstream components MEK1/2 and ERK1/ERK2. Raf protein kinases have been shown to play a role in tumorigenesis including tumor cell proliferation, survival, invasion and angiogenesis, Sebolt-Leopold et al, *Nat Rev Cancer,* 2004, 4: 937-947; Wellbrock et al, *Nat Rev Mol Cell Biol,* 2004, 5: 875-885. MAPK pathway activation in tumor cells by multiple mechanisms such as mutations or overexpression of RTKs and Ras mutations, all go through Raf proteins. More importantly, activating mutations of B-RAF, Davies et al, *Nature,* 2002, 417: 949-954, are often observed in several malignancies including melanoma, colorectal, lung, ovarian and thyroid carcinomas. Almost 90% of the B-Raf mutations are a T1799A change in exon 15 which results is a Val to Glu amino acid substitution (B-Raf V600E). This mutation in B-Raf leads to constitutive kinase activity approximately 500 fold greater than that of wild type protein, and malignant transformation. Additional mutations, such as T529I, a threonine to isoleucine B-Raf gatekeeper mutation and G468A, a B-Raf secondary mutation at G1403C in exon 11 are also known and believed to play a role in causing, maintaining, or exacerbating malignant transformation, Whittaker et al, *Sci. Transl. Med.,* 2010, 2(35) ra41; Wan et al, *Cell,* 2004, 116: 855-867.

Recently, a B-Raf specific kinase inhibitor vemurafenib (also called PLX-4032) was approved by the United States Food and Drug Administration (FDA) for treatment of melanoma patients with B-Raf V600E mutation. Vemurafenib is efficacious and provides survival benefit in these patients. However, patients responsive to this drug generally develop drug resistance which leads to disease relapse in an average of 7 months. Similar to many other targeted therapies, the acquired resistance to B-RAF inhibition presents a therapeutic challenge to long-term survival benefit in this patient population.

To improve the benefit of B-Raf inhibitors, research continues to identify the mechanisms which render mutant B-RAF expressing melanoma cells resistant to vemurafenib. Recent studies have indicated that reactivation of the MAPK pathway is a mechanism of resistance to B-RAF inhibition. Resistant mechanisms primarily involve reactivation of ERK signaling through bypass mechanisms that are either Ras/RAF dependent, such as N-Ras activation, Nazarian et al, *Nature.* 2010, 468: 973-7, H-Ras activation (Su et al, *New England Journal of Medicine.* 2012, 366: 207-215) or C-RAF upregulation, (Johannessen et al, *Nature.* 2010, 468: 968-72; Montagut et al, *Cancer Res.* 2008, 68: 4853-61), aberrantly spliced variants of B-RAF V600E (Poulikakos et al, *Nature.* 2011, 480: 387-390, or Ras/RAF independent (Tpl2/COT overexpression) Johannessen et al, *Nature.* 2010, 468: 968-72. Consequently, multiple mechanisms could attenuate the effect of B-RAF inhibition on MAPK signaling in B-RAF mutant cancers. Although a gatekeeper mutation of B-RAF (T529I) that could cause resistance to BRAF inhibition has not yet been clinically identified, such a mutation has been experimentally demonstrated to cause resistance, Whittaker et al, *Sci Transl Med.* 2010, 2(35): ra41. Recent studies have also suggested that activation of MAPK-redundant signaling pathways by RTKs such as IGF-1R or PDGFRβ could play a role in acquired resistance to B-RAF inhibition; Nazarian et al, *Nature.* 2010, 468: 973-7; Villanueva et al, *Cancer Cell.* 2010, 18: 683-95; Shi et al, *Cancer Res.* 2011, 71: 5067-74. It is clear that MAPK reactivation is involved in many of these resistance mechanisms. A pan Raf inhibitor is expected to block MAPK reactivation.

Additionally, B-Raf specific inhibitors including vemurafenib and its close analogue N-[3-(5-chloro-1H-pyrrolo [2,3-1)]pyridine-3-carbonyl)-2,4-difluorophenyl]propane-1-sulfonamide (PLX4720; a commercially available selective B-Raf inhibitor) were demonstrated to induce paradoxical pathway activation through dimerization with other Raf isoforms in a B-Raf wild type background, Hatzivassiliou G, et al. *Nature,* 2010, 464: 431-435; Poulikakos et al, *Nature,* 2010, 464: 427-430; Heidorn, et al, *Cell,* 2010, 140: 209-221. Vemurafenib is believed to activate the Raf/MEK/ERK pathway through binding B-Raf wild type and stimulating B-Raf-C-Raf dimerization. This paradoxical pathway activation by B-Raf specific inhibition is believed to be a major reason of skin side effects (such as squamous cell carcinoma) in some melanoma patients treated with vemurafenib. Vemurafenib is not approved for treatment of cancer patients with B-Raf wild type genetic background due to its paradoxical pathway activation activity in this genetic background.

The tested exemplified compounds of Formula I are Raf kinase inhibitors inhibiting all isoforms of Raf proteins including A-Raf, B-Raf, C-Raf, and B-Raf V600E mutation. Due to their pan Raf activities, the tested exemplified compounds of Formula I are active against tumor cells with MAPK pathway activation by upstream signaling such as N-Ras mutation and K-Ras mutation, both with B-Raf wild type genetic background. Therefore, the tested exemplified compounds of Formula I have the potential for treating cancer patients with B-Raf mutation (such as melanoma, colorectal, lung, ovarian and thyroid carcinoma), N-Ras mutation, B-Raf wild type (such as melanoma, AML, CML, ALL, CLL, liver cancer), (Schubbert et al, *Nature Reviews Cancer,* 2007, 7: 295; Pylayeva-Gupta et al, *Nature Reviews Cancer,* 2011, 11: 761); or K-Ras mutation, B-Raf wild type (such as biliary tract, cervical, colorectal, endometrial, lung, ovarian, pancreatic, and liver; Schubbert et al, *Nature Reviews Cancer,* 2007, 7: 295; Pylayeva-Gupta et al, *Nature Reviews Cancer,* 2011, 11: 761) or other mechanism of Raf activation including upstream activating RTK mutation/overexpression. The tested exemplified compounds of Formula I are also active against melanoma tumor cells which developed resistance to vemurafenib. Therefore, it is believed that the tested exemplified compounds will be effective for melanoma patients who have failed vemurafenib or other B-Raf inhibitors.

The tested exemplified compounds of Formula I are also inhibitors of c-Kit. C-Kit is a receptor tyrosine kinase that normally controls the function of primitive hematopoietic cells, melanocytes and germ cells. Following binding with its ligand stem cell factor (SCF), c-Kit undergoes dimerization/oligomerization and autophosphorylation. Genetic mutations (such as L576P, K642E, T670I, and V654A) of c-Kit that constitutively activate c-Kit can lead to melanoma, acute myelogenous leukemia, and gastrointestinal stromal tumors (GIST), therefore, the tested exemplified compounds have the potential to treat melanoma, acute myelogenous leukemia and GIST patients, Lennartsson et al, *Current Cancer Drug Targets,* 2006, 6: 65.

Exemplified compounds of Formula I can be used as a single agent or in combination with one or more other approved drugs for treatment of cancer patients. These cancer patients include: melanoma patients with B-Raf V600E mutation, melanoma patients who failed vemurafenib or other B-Raf inhibitors, melanoma patients with N-Ras mutation B-Raf wild type, melanoma patients with c-Kit overexpression or cKit mutation; colorectal cancer patients with B-Raf V600E mutation or K-Ras mutation B-Raf wild type; ovarian cancer patients with B-Raf V600E mutation or K-Ras mutation B-Raf wild type; lung cancer patients with B-Raf V600E mutation or K-Ras mutation B-Raf wild type; myeloid leukemia patients with N-Ras mutation B-Raf wild type, or c-Kit overexpression or c-Kit mutation; liver cancer patients with N-Ras or K-Ras mutation B-Raf wild type; pancreatic cancer patients with K-Ras mutation B-Raf wild type; thyroid carcinoma patients with B-Raf V600E or N-Ras mutation B-Raf wild type; biliary tract cancer patients with K-Ras mutation B-Raf wild type; GIST patients with c-Kit mutation or overexpression.

The following in vitro studies demonstrate the Ras/Raf/MEK/ERK pathway signaling inhibitory activity of the exemplified compounds of Formula I. These assays are generally recognized by those skilled in the art as indicative of human clinical chemotherapeutic activity. Assays evidencing pan Raf inhibition and pathway signaling inhibitory activity may be carried out substantially as follows or by similar assays affording similar data. Unless otherwise stated, reported $IC_{50}$ values are absolute.

Enzymatic Assays of Kinase Activities of B-Raf, C-Raf and B-Raf Mutations

Test compounds are evaluated for their inhibitory activities against one or more of human wild type B-Raf, human wild type C-Raf, human B-Raf V600E, human B-Raf V600E+T529I or human B-Raf V600E+G468A. T529I is a threonine to isoleucine B-Raf gatekeeper mutation and G468A is a B-Raf secondary mutation at G1403C in exon 11. The enzymatic assays of B-Raf, C-Raf and B-Raf mutations evaluate a property of Raf and MEK1 complex, which in the presence of ATP, catalyzes an enhanced ATP hydrolysis (Rominger, et al, *Arch. Biochem. Biophys.* 2007, 464: 130-137; US Patent Publication No. 2006/0211073). The ADP formed is monitored by the well-known coupled PK/LDH (pyruvate kinase/lactate dehydrogenase) system in the form of NADH oxidation, which can be monitored and detected spectrophotometrically by absorbance at 340 nm (A340; for principal of the method see Schindler et al, *Science,* 2000, 289: 1938-1942). Raf activated MEK1 ATPase activity is a property shared by all forms of Raf proteins.

Expression and Purification of Raf Proteins

Generally, cell lines are generated using commercially available materials by procedures known to and routinely used by those skilled in the art. The nucleotide sequences encoding full-length B-Raf wild type DNA (National Center for Biotechnology Information (NCBI), Reference Sequence NC_000007.13), C-Raf (National Center for Biotechnology Information (NCBI), Reference Sequence NC_000003.11) and A-Raf (National Center for Biotechnology Information (NCBI), Reference Sequence NC 000023.10) are known. See also, e.g., for B-Raf: S. Ikawa, et al., "B-raf, a new member of the raf family, is activated by DNA rearrangement," *Mol Cell Biol,* 8(6):2651-4 (1988); for C-Raf: M. Fukui, et al., "Molecular cloning and characterization of an activated human c-raf-1 gene," *Mol Cell Biol,* 7(5):1776-81 (1987); Bonner, et al., "The complete coding sequence of the human raf oncogene and the corresponding structure of the c-raf-1 gene," *Nucleic Acids Res.,* 14 (2), 1009-1015 (1986); for MEK1: C. F. Zheng, et al., "Cloning and characterization of two distinct human extracellular signal-regulated kinase activator kinases, MEK1 and MEK2," *J. Biol. Chem.,* 268 (15), 11435-11439 (1993); for tag information: J. Tsai, et al., "Discovery of a selective inhibitor of oncogenic B-Raf kinase with potent antimelanoma activity," *Proc. Natl. Acad. Sci. U.S.A.,* 105(8), 3041-3046 (2008); G. Hatzivassiliou, et al., "RAF inhibitors prime wild-type RAF to activate the MAPK pathway and enhance growth," *Nature,* 464 (7287), 431-435 (2010).

B-RafV600E (residues 433-726 containing V600E mutation) containing an N-terminal purification tag is expressed and purified essentially as described previously (Wan et al, *Cell,* 2004, 116, 855-867).

B-Raf V600E constructs containing a secondary T529I mutation or G468A mutation are generated by site directed mutagenesis (Quikchange, Strategene) of the base bRaf (433-726, V600E) construct.

Sequences that are used herein include:B-RafV600E (residues 433-726 containing V600E mutation) without N-terminal purification tag; B-RafV600E (residues 433-726 containing V600E and T529I mutations) without N-terminal purification tag; B-RafV600E (residues 433-726 containing V600E and G468A mutations) without N-terminal purification tag; BRAF-V600E; BRAF-V600E+T529I; BRAF-V600E+G468A; BRAF-wild type, full length; C-RAF; MEK1 protein sequence used for screening.

Enzymatic Assays Measuring Raf Kinase Activity

Test compounds are evaluated for their inhibitory activities against one or more of wild type B-Raf, wild type C-Raf, B-Raf V600E, B-Raf V600E+T529I and B-Raf V600E+G468A. T529I is a B-Raf gatekeeper mutation and G468A is a B-Raf secondary mutation. The enzymatic assays of B-Raf, C-Raf and B-Raf mutations evaluate a property of Raf and MEK1 complex, which in the presence of ATP, catalyzes an enhanced ATP hydrolysis (Rominger, et al, *Arch. Biochem. Biophys.* 2007, 464: 130-137). The ADP formed is monitored by the well-known coupled PK/LDH (pyruvate kinase/lactate dehydrogenase) system in the form of NADH oxidation, which can be monitored and detected by absorbance at 340 nm (A340; for principal of the method see Schindler et al, *Science,* 2000, 289: 1938-1942). Raf activated MEK1 ATPase activity is a property shared by all forms of Raf proteins. In the B-Raf wild type enzymatic assay, the reaction mixture contains 1.2 nM B-Raf, 30 nM MEK1, 1000 uM ATP, 3.5 units (per 100 ul) of PK, 5 units (per 100 ul) of LDH, 1 mM phosphoenol pyruvate (PEP), and 280 uM of NADH. In the C-Raf assay, the reaction mixture contains 0.6 nM C-Raf, 26 nM MEK1, 2000 uM ATP, and the same amount of PK, LDH, PEP and NADH as above. In the B-Raf V600E assay, the reaction mixture contains 1.6 uM B-Raf V600E, 26 nM MEK1, 200 uM ATP and the same amount of PK, LDH, PEP and NADH as above. In the B-RafV600E+T529I assay, the reaction mixture contains 6.2 nM B-Raf V600E+T529I, 30 nM MEK1, 200 uM ATP and the same amount of PK, LDH, PEP and NADH as above. In the B-RafV600E+G468A assay, the reaction mixture contains 3.5 nM B-Raf, 30 nM MEK1, 200 uM ATP and the same amount of PK, LDH, PEP and NADH as above. All assays are started by mixing the above mixture with test compound and monitoring at A340 continuously for approximately 5 hr. Reaction data at the 3 to 4 hour time frame are collected to calculate $IC_{50}$ values. In the aforementioned assays, the enzyme constructs can be screened prior to or after cleavage of the N-terminal purification tag.

TABLE 1

| | Enzyme $IC_{50}$, nM | |
|---|---|---|
| Example No. | B-Raf V600E | C-Raf |
| 1 | + | + |
| 2 | + | + |
| 3 | + | + |
| 4 | + | + |
| 5 | + | + |
| 6 | + | + |
| 7 | + | + |
| 8 | + | + |
| 9 | + | + |

TABLE 1-continued

| Example No. | Enzyme IC$_{50}$, nM | |
|---|---|---|
| | B-Raf V600E | C-Raf |
| 10 | + | + |
| 11 | + | + |
| 12 | + | + |
| 13 | + | + |
| 14 | + | + |
| 15 | + | + |
| 16 | + | + |
| 17 | + | + |
| 18 | + | + |
| 19 | + | + |
| 20 | + | + |
| 21 | + | + |
| 22 | + | + |
| 23 | + | + |
| 24 | + | + |
| 25 | + | + |
| 26 | + | + |
| 27 | + | + |
| 28 | + | + |
| 29 | + | + |
| 30 | + | + |
| 31 | + | + |
| 32 | + | + |
| 33 | + | + |
| 34 | + | + |
| 35 | + | + |
| 36 | + | + |

Wherein "+" indicates IC$_{50}$ < 150 nM for inhibition of B-Raf V600E or C-Raf. These data evidence that the exemplified compounds of Formula I inhibit B-Raf V600E and C-Raf in these assays.

Enzymatic Assay of c-Kit Kinase Activity c-Kit is an important oncogene, and its overexpression and genetic mutations often occur in melanoma and gastrointestinal stromal tumor (GIST) patients. In the c-Kit enzymatic assay, the phosphorylation of poly E4Y by ATP catalyzed by human c-Kit is monitored spectrophotometrically. The ADP produced from the kinase reaction is coupled to pyruvate kinase/lactate dehydrogenase (PK/LDH) reactions where NAD is formed from pyruvate and NADH. NADH can be detected by absorbance at 340 nm, as described above for enzymatic assays of kinase activities of B-Raf, C-Raf and B-Raf mutations.

Expression and Purification of c-Kit Wild Type Receptor

Generally, cell lines are generated using commercially available materials by procedures known to and routinely used by those skilled in the art.

The nucleotide sequence encoding full-length human wild type c-Kit receptor DNA (National Center for Biotechnology Information (NCBI) Reference Sequence NC_000004.11), is known. See also, e.g., for human cKit protein sequence: Y. Yarden, Y., et al., "Human proto-oncogene c-kit: a new cell surface receptor tyrosine kinase for an unidentified ligand," EMBO J. 6 (11), 3341-3351 (1987); for GST fusion proteins: D. B. Smith, et al., "Single-step purification of polypeptides expressed in Escherichia coli as fusions with glutathione S-transferase," Gene 67 (1988) 31-40; D. B. Smith, "Purification of glutathione S-transferase fusion proteins," Methods Mol. Cell. Biol. 4 (1993) 220-229.

c-Kit Assays

The assay reaction mixture includes 6 nM human wild type c-KIT, 1 mg/mL Poly (Glu,Tyr) (Sigma), 1 mM Phosphoenol-pyruvate, 280 µM NADH, 5 U/3.5 U (per 100 ul) Pyruvate Kinase/Lactate Dehydrogenase, 85 mM Tris, pH 7.5, 17 mM MgCl$_2$, 0.0042% Triton® X-100, 0.005% BSA, 1% DMSO. Test compound is incubated with the reaction mixture for 0.5 hour before adding 200 µM ATP to start the reaction at 30° C. Reaction rates at 0.5 to 1 h are used to calculate % inhibition and IC$_{50}$'s.

A sequence that is used herein includes c-KIT with N-terminal GST fusion.

TABLE 2

Human c-Kit Inhibition
c-Kit Inhibition

| Example No. | c-Kit IC$_{50}$ (nM) |
|---|---|
| 1 | + |
| 2 | + |
| 3 | + |
| 4 | + |
| 5 | + |
| 6 | + |
| 7 | + |
| 8 | + |
| 9 | + |
| 10 | + |
| 11 | + |
| 12 | + |
| 13 | + |
| 14 | + |
| 15 | + |
| 16 | + |
| 17 | + |
| 18 | Not Tested |
| 19 | Not Tested |
| 20 | + |
| 21 | + |
| 22 | + |
| 23 | + |
| 24 | + |
| 25 | + |
| 26 | + |
| 27 | + |
| 28 | + |
| 29 | + |
| 30 | + |
| 31 | + |
| 32 | + |
| 33 | + |
| 34 | + |
| 35 | + |
| 36 | + |

Wherein "+" indicates IC$_{50}$ < 150 nM for inhibition of c-Kit. This data evidences the tested exemplified compounds are human wild type c-Kit inhibitors in this assay.

CellTiter-Blue Cell Proliferation and Viability Assay

A375 Cell Proliferation Assay

A375 cells (catalog #CRL-1619) are obtained from the American Type Culture Collection (ATCC, Manassas, Va.). Briefly, cells are grown in DMEM High Glucose supplemented with 10% characterized fetal bovine serum (Invitrogen, Carlsbad, Calif.) and 1% Penicillin/Streptomycin/L-Glutamine at 37 degrees Celsius, 5% CO$_2$, and 95% humidity. Cells are allowed to expand until reaching 70-95% confluency at which point they are subcultured or harvested for assay use. A serial dilution of test compound is dispensed into a 384-well black clear bottom plate in triplicate. Six hundred twenty-five cells are added per well in 50 µL complete growth medium in the 384-well plate. Plates are incubated for 67 hours at 37 degrees Celsius, 5% CO$_2$, and 95% humidity. At the end of the incubation period, 10 µL of a 440 µM solution of resazurin (Sigma, St. Louis, Mo.) in PBS is added to each well of the plate and plates are incubated for an additional 5 hours at 37 degrees Celsius, 5% CO$_2$, and 95% humidity. Plates are read on a Synergy2 reader (Biotek, Winooski, Vt.) using an excitation of 540 nm and an emission of 600 nm. Data is analyzed using Prism software (Graphpad, San Diego, Calif.) to calculate IC$_{50}$ values.

Colo-205 Cell Proliferation Assay

Colo205 cells (catalog #HB-8307) are obtained from the American Type Culture Collection (ATCC, Manassas, Va.). Briefly, cells are grown in RPMI 1640 supplemented with 10% characterized fetal bovine serum (Invitrogen, Carlsbad, Calif.), 1 mM sodium pyruvate, and 1% Penicillin/Streptomycin/L-Glutamine at 37 degrees Celsius, 5% $CO_2$, and 95% humidity. Cells are allowed to expand until reaching 30-60% confluency at which point they are subcultured or harvested for assay use. A serial dilution of test compound is dispensed into a 384-well black clear bottom plate in triplicate. One thousand two-hundred fifty cells are added per well in 50 µL complete growth medium in the 384-well plate. Plates are incubated for 67 hours at 37 degrees Celsius, 5% $CO_2$, and 95% humidity. At the end of the incubation period, 10 µL of a 440 µM solution of resazurin (Sigma, St. Louis, Mo.) in PBS is added to each well of the plate and plates are incubated for an additional 5 hours at 37 degrees Celsius, 5% $CO_2$, and 95% humidity. Plates are read on a Synergy2 reader (Biotek, Winooski, Vt.) using an excitation of 540 nm and an emission of 600 nm. Data is analyzed using Prism software (Graphpad, San Diego, Calif.) to calculate $IC_{50}$ values.

HT-29 Cell Proliferation Assay

HT-29 cells (catalog #HTB-38) are obtained from the American Type Culture Collection (ATCC, Manassas, Va.). Briefly, cells are grown in McCoy's 5A supplemented with 10% characterized fetal bovine serum (Invitrogen, Carlsbad, Calif.), and 1% Penicillin/Streptomycin/L-Glutamine at 37 degrees Celsius, 5% $CO_2$, and 95% humidity. Cells are allowed to expand until reaching 75-90% confluency at which point they are subcultured or harvested for assay use. A serial dilution of test compound is dispensed into a 384-well black clear bottom plate in triplicate. One thousand two-hundred fifty cells are added per well in 50 µL complete growth medium in the 384-well plate. Plates are incubated for 67 hours at 37 degrees Celsius, 5% $CO_2$, and 95% humidity. At the end of the incubation period, 10 µL of a 440 µM solution of resazurin (Sigma, St. Louis, Mo.) in PBS is added to each well of the plate and plates are incubated for an additional 5 hours at 37 degrees Celsius, 5% $CO_2$, and 95% humidity. Plates are read on a Synergy2 reader (Biotek, Winooski, Vt.) using an excitation of 540 nm and an emission of 600 nm. Data is analyzed using Prism software (Graphpad, San Diego, Calif.) to calculate $IC_{50}$ values.

HCT-116 Cell Proliferation Assay

HCT-116 cells (catalog #CCL-247) are obtained from the American Type Culture Collection (ATCC, Manassas, Va.). Briefly, cells are grown in McCoy's 5A supplemented with 10% characterized fetal bovine serum (Invitrogen, Carlsbad, Calif.), and 1% Penicillin/Streptomycin/L-Glutamine at 37 degrees Celsius, 5% $CO_2$, and 95% humidity. Cells are allowed to expand until reaching 75-90% confluency at which point they are subcultured or harvested for assay use. A serial dilution of test compound is dispensed into a 384-well black clear bottom plate in triplicate. Six hundred twenty-five cells are added per well in 50 µL complete growth medium in the 384-well plate. Plates are incubated for 67 hours at 37 degrees Celsius, 5% $CO_2$, and 95% humidity. At the end of the incubation period, 10 µL of a 440 µM solution of resazurin (Sigma, St. Louis, Mo.) in PBS is added to each well of the plate and plates are incubated for an additional 5 hours at 37 degrees Celsius, 5% $CO_2$, and 95% humidity. Plates are read on a Synergy2 reader (Biotek, Winooski, Vt.) using an excitation of 540 nm and an emission of 600 nm. Data is analyzed using Prism software (Graphpad, San Diego, Calif.) to calculate $IC_{50}$ values.

SK-Mel-2 Cell Proliferation Assay

Sk-Mel-2 cells (catalog #HTB-68) are obtained from the American Type Culture Collection (ATCC, Manassas, Va.). Briefly, cells are grown in MEM supplemented with 10% characterized fetal bovine serum (Invitrogen, Carlsbad, Calif.), 1 mM sodium pyruvate, 0.1 mM non-essential amino acids, and 1% Penicillin/Streptomycin/L-Glutamine at 37 degrees Celsius, 5% $CO_2$, and 95% humidity. Cells are allowed to expand until reaching 70-95% confluency at which point they are subcultured or harvested for assay use. A serial dilution of test compound is dispensed into a 384-well black clear bottom plate in triplicate. One thousand two-hundred fifty cells are added per well in 50 µL complete growth medium in the 384-well plate. Plates are incubated for 67 hours at 37 degrees Celsius, 5% $CO_2$, and 95% humidity. At the end of the incubation period, 10 µL of a 440 µM solution of resazurin (Sigma, St. Louis, Mo.) in PBS is added to each well of the plate and plates are incubated for an additional 5 hours at 37 degrees Celsius, 5% $CO_2$, and 95% humidity. Plates are read on a Synergy2 reader (Biotek, Winooski, Vt.) using an excitation of 540 nm and an emission of 600 nm. Data is analyzed using Prism software (Graphpad, San Diego, Calif.) to calculate $IC_{50}$ values.

The A375, HT-29, and Colo-205 cells (ATCC) harbor a V600E mutation. The HCT-116 cells (ATCC) harbor a K-Ras mutation B-Raf wild type, and the SK-Mel-2 cells (ATCC) harbor an N-Ras mutation B-Raf wild type.

TABLE 3

Cell Proliferation and Viability Inhibition

| Example No. | Cell Proliferation Inhibition $IC_{50}$, nM | | | | |
|---|---|---|---|---|---|
| | A375 | HT-29 | Colo-205 | HCT-116 | SK-Mel-2 |
| 1 | + | + | + | ++ | ++ |
| 2 | + | + | + | ++ | + |
| 3 | + | + | + | ++ | ++ |
| 4 | ++ | + | ++ | ++ | ++ |
| 5 | + | + | + | ++ | ++ |
| 6 | + | + | + | ++ | + |
| 7 | + | + | + | ++ | + |
| 8 | ++ | ++ | + | +++ | ++ |
| 9 | ++ | ++ | ++ | +++ | ++ |
| 10 | ++ | ++ | ++ | +++ | +++ |
| 11 | ++ | ++ | ++ | +++ | ++ |
| 12 | +++ | ++ | ++ | +++ | ++ |
| 13 | +++ | ++ | ++ | +++ | ++ |
| 14 | ++ | + | + | ++ | +++ |
| 15 | + | + | + | ++ | ++ |
| 16 | + | + | + | ++ | ++ |
| 17 | + | + | + | ++ | ++ |
| 18 | ++ | + | + | ++ | ++ |
| 19 | ++ | ++ | ++ | +++ | ++ |
| 20 | + | + | + | ++ | + |
| 21 | + | + | + | ++ | ++ |
| 22 | + | + | + | ++ | ++ |
| 23 | ++ | + | + | ++ | ++ |
| 24 | + | + | + | ++ | ++ |
| 25 | + | + | + | ++ | ++ |
| 26 | ++ | + | ++ | +++ | ++ |
| 27 | + | + | + | ++ | ++ |
| 28 | +++ | ++ | ++ | +++ | +++ |
| 29 | +++ | ++ | ++ | +++ | +++ |
| 30 | + | + | + | ++ | ++ |
| 31 | + | + | + | ++ | ++ |
| 32 | + | + | + | ++ | ++ |
| 33 | + | + | + | ++ | ++ |
| 34 | ++ | + | ++ | ++ | ++ |
| 35 | + | + | + | ++ | + |
| 36 | +++ | ++ | +++ | +++ | +++ |

Wherein "+" indicates $IC_{50}$ < 100 nM; "++" indicates 100 nM ≤ $IC_{50}$ < 1000 nM; "+++" indicates 1,000 nM ≤ $IC_{50}$ < 10,000 nM.

The data in Table 3 evidences the exemplified compounds of Formula I inhibit proliferation and viability of the specified cells harboring the identified mutations in this assay.

Inhibition in Vemurafenib-Resistant Melanoma Cells

Vemurafenib (PLX4032) and PLX4720 are inhibitors of mutant B-RAF V600E (Johannessen et al, *Nature*, 2010, 468: 968-72; Montagut et al, *Cancer Res.* 2008, 68: 4853-61; Wagle et al, *Journal of Clinical Oncology*, 2011, 29: 3085-96). Some of the patients who initially respond to vemurafenib therapy develop drug resistance and become refractory within an average of 7 months, Whittaker et al, *Sci Transl Med.* 2010, 2: 35-41. A vemurafenib-resistant cell line is generated by chronic treatment of the human melanoma cell line A375 (ATCC) harboring the B-RAF V600E mutation with increasing concentrations PLX4720.

Generation of B-RAF V600E Melanoma Cell Lines Resistant to B-RAF Inhibition

To generate resistant cells, A375 cells are cultured in growth medium, essentially as described above for the A375 cell proliferation assay, in the presence of gradually increasing concentrations of N-[3-(5-chloro-1H-pyrrolo [2, 3-1)] pyridine-3-carbonyl)-2,4-difluorophenyl]propane-1-sulfonamide (PLX4720; a commercially available selective B-Raf inhibitor) from 0.02 to 2 μM through approximately 4 months and 30 passages to afford a resistant cell line designated as A375res. The resistance of A375res to vemurafenib and PLX4720 is confirmed by the shift of $IC_{50}$ values in Cell Titer Blue cell proliferation assay.

In these A375res cells, PLX4720 loses much of its activity shifting more than 27-fold from an $IC_{50}$ of 369 nM to greater than 10 uM in a 72 hour proliferation assay performed essentially as described above for the A375 cell line. Similarly, the $IC_{50}$ of vemurafenib shifts from 175 nM to greater than 10 uM, a change of more than 57-fold. In contrast, the $IC_{50}$ shift of tested examples 4, 15, 16, 17, 20, 21, 24, 25, 26, 27, 28, 30, 34, and 35 falls in a narrow range between 0.6 to 1.9 fold, with absolute $IC_{50}$ values between 15 nM and 1100 nM. These data evidence that the examples of the invention inhibit cell proliferation in A375res cells in this assay.

Utility of Compounds of Formula I in the Treatment of Wt BRAF Tumor Cells

Recent published studies (see above) suggest that B-Raf specific inhibitors, such as vemurafenib (PLX-4032) induce "paradoxical pathway activation" through B-Raf dimerization with other Raf isoforms in B-Raf wild type backgrounds. Vemurafenib is not approved for treatment of melanoma cancer patients with B-Raf wild type genetic background. This paradoxical pathway activation is also believed to be a cause of skin side effects (such as squamous cell carcinoma) in some melanoma patients treated with vemurafenib.

Examples of Formula I are tested against HCT-116 cells harboring wild type B-Raf and K-Ras mutation. The phospho-ERK activities are evaluated as described below.
HCT-116 Cell pERK Assay HCT-116 cells (catalog #CCL-247) are obtained from the American Type Culture Collection (ATCC, Manassas, Va.). Briefly, cells are grown in McCoy's 5A supplemented with 10% characterized fetal bovine serum (Invitrogen, Carlsbad, Calif.), and 1% Penicillin/Streptomycin/L-Glutamine at 37 degrees Celsius, 5% $CO_2$, and 95% humidity. Cells are allowed to expand until reaching 75-90% confluency at which point they are subcultured or harvested for assay use. HCT-116 cells suspended in complete media are added to 384-well tissue culture treated plates ($3 \times 10^5$ cells/mL; 7,500 cells per well). The cells are incubated overnight at 37 degrees Celsius, 5% $CO_2$, and 95% humidity. Next, test compound or DMSO diluted in complete media is added to the wells (0.25% final DMSO concentration). The plates are then incubated for 4 hours at 37 degrees Celsius, 5% $CO_2$, and 95% humidity. Following compound incubation, the cells are lysed at 4° C. for 20 minutes with shaking. Cell lysates are centrifuged and the supernatant is transferred to a new plate. An aliquot of each lysate is transferred to a white 384-well assay plate. Using the AlphaScreen SureFire pERK kit (Perkin-Elmer, Waltham, Mass.), an acceptor bead mixture is added to each well and incubated for 2 h at room temperature in the dark. A donor bead mixture is then added to each well and incubated for 2 h at room temperature in the dark. Plates are read using a Synergy2 plate reader (Biotek, Winooski, Vt.) in Plate Mode with Timing Control. Read: (F)1: excitation: 680/30 nm, emission: Plug. 2: Excitation: Plug, emission: 570/100 nm. Top mirror 635 nm. Data is analyzed using Prism software (Graphpad, San Diego, Calif.) to calculate $IC_{50}$ values and Excel software (Microsoft, Redmond, Wash.) to calculate stimulation compared to control.

Examples of Formula I have Minimal Paradoxical Pathway Activation in HCT-116 Cells Examples of the invention evidence minimal paradoxical pathway stimulation, and maintain phospho-ERK inhibiting activities in HCT-116 cells harboring B-Raf wild type and K-Ras genetic background. Tested examples 24, 25 and 35 substantially reduce phospho-ERK signal with $IC_{50}$'s between 2 nM and 472 nM in this assay. In contrast, vemurafenib stimulates the pERK signal in this assay at concentrations up to about 3 uM. Since compounds of Formula I also evidence c-Raf inhibition (prior assays, above) it is believed that paradoxical pathway activation will be minimal, or will occur at only very low inhibitor concentrations, consistent with the potent suppression of pERK measured in the HCT-116 cells.

In Vivo Activity

A375 Mouse Xenograft Pharmacodynamic Assay

To evaluate the in vivo pharmacodynamic (PD) effects of compounds of Formula I, an A375 (BRAF V600E) xenograft model is employed. Briefly, $10 \times 10^6$ A375 tumor cells (ATCC) are prepared in a 1:1 matrigel mix (0.2 mL total volume) and implanted by subcutaneous injection in hind leg of nude female mice. A total of 4 mice each for each dosing group are employed. Treatment is initiated with oral administration (gavage) of test compound or vehicle (20% captisol, 25 mM phosphate, pH2.0) in 0.2 mL volume when average tumor size reaches approximately 300 mg. After a fixed time interval, the tumors are harvested and the phospho-ERK levels are measured by ELISA (Enzyme-linked immunosorbent assay). Treated groups are compared to the vehicle control group to calculate % inhibition. Data for compounds of Formula I are presented in table 4.

TABLE 4

Inhibition of tumor pERK levels in A375 xenografts 2 h post dose

| Example | Dose | Measured pERK inhibition 2 h post dose |
|---|---|---|
| Ex 1 | 20 mg/kg | 54% inhibition |
| Ex 2 | 20 mg/kg | 38% inhibition |
| Ex 4 | 20 mg/kg | 84% inhibition |
| Ex 5 | 20 mg/kg | 77% inhibition |
| Ex 24 | 20 mg/kg | 88% inhibition |
| Ex 34 | 20 mg/kg | 72% inhibition |
| Ex 35 | 20 mg/kg | 79% inhibition |

To further evaluate in vivo activity of compounds of Formula I, A375 V600E (ATCC) and HCT-116 K—Ras mutant B-Raf wild type (ATCC) xenograft tumor models are used. Briefly, $10 \times 10^6$ cells (A375) or $5 \times 10^6$ cells (HCT-116) in a 1:1 medium and matrigel mix (0.2 mL total volume) are implanted by subcutaneous injection in the hind leg of nude female rats (NIH model No. NIHRNU-M from Taconic). A total of 8 rats in each group are used for the efficacy study, and a total of 3-4 rats in each group are used for a pharmacodynamic study. Treatment is initiated with oral administration (gavage) of test compound or vehicle (20% Captisol®, 25 mM phosphate, pH 2.0) in 0.6 mL volume when tumor size reaches approximately 500 mg. Test compound is orally dosed twice a day for 21 days. Tumor growth and body weight are monitored over time to evaluate activity and signs of toxicity. Bidimensional measurements of tumors are performed twice a week and tumor volumes are calculated based on mid-axis length and mid-axis width. Tumor volume data are transformed to a log scale to equalize variance across time and treatment groups. The log volume data are analyzed with a two-way repeated measures analysis of variance by time and treatment using the MIXED® procedures in SAS® software (version 8.2). The correlation model for the repeated measures is spatial power. Treated groups are compared to the control group at each time point. The MIXED® procedure is also used separately for each treatment group to calculate adjusted means and standard errors at each time point. Both analyses account for the autocorrelation within each animal and the loss of data that occurs when animals with large tumors are removed from the study early. The adjusted means and standard errors are plotted for each treatment group versus time. Example 24 was orally dosed twice a day at 10 and 20 mg/kg for 21 days in the A375 rat xenograft efficacy model. Both dosing groups evidenced tumor growth inhibition and tumor growth regression, and there was no animal body weight loss in either group. These data evidence in vivo activity by Example 24 and support that the enzymatic, cell lysate and cell proliferation data correlates to in vivo activity.

We claim:

1. A compound of the formula:

Formula IA

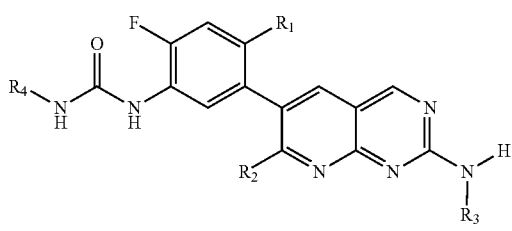

wherein:
R₁ is hydrogen, Ci-C₄alkyl, or halo;
R₂ is Ci-C₄alkyl or hydrogen;
R₃ is Ci-C₄ alkyl, hydrogen, —C(O)R₈, oxetanyl, tetrahydrofuranyl, or tetrahydropyranyl; and wherein the C₁-C₄ alkyl is optionally substituted with hydroxyl, C₁-C₂ alkoxy, oxetanyl, tetrahydrofuranyl, tetrahydropyranyl, N-azetidinyl, N-piperazinyl, C5-C₆ heteroaryl, N-morpholino, N-piperidinyl, N-pyrrolidinyl, or (C₁-C₄ alkyl)ₙ amino- wherein n is 0, 1, or 2; and wherein each of the rings as substituents on a C₁-C₄ alkyl are further optionally substituted with one to three of the same or different C₁-C₄ alkyl, fluoro, C1-C4 alkoxy, —C(0)Rg, or (C1-C4 alkyl)ₘamino, where m is 0, 1 or 2;
Rt is R5-(CH₂)—, or C₄-C₆ cycloalkyl optionally substituted with one or two of the same or different methyl, ethyl, or fluoro;
Rs is —CHR₆R7 or C3-C₆ cycloalkyl optionally substituted with one or two of the same or different C₁-C₂ alkyl;
R6 is hydrogen or hydroxyl, or C₁-C₄ alkoxy;
R₇ is isopropyl, t-butyl, 1-fluoro-1-methyl-ethyl, 1-cyano-1-methyl-ethyl, 1-(Ci-C₄ alkoxy)-1-methyl-ethyl, 1-(Ci-C₄ alkyl)-cycloprop-1-yl, 1-(fluoro(Ci-C₂ alkyl) cycloprop-1-yl, or 2,2,2-trifluoro-1,1-dimethyl-ethyl where fluoro(Ci-C₂ alkyl) has one to five fluoro substituents;
Rs is hydrogen, Ci-C₆ linear or branched alkyl, or (Ci-C₄)ₚ amino where p is 0, 1, or 2, and each alkyl is optionally substituted with the same or different Ci-C₄ alkoxy, hydroxyl, or (Ci-C₄ alkyl)ᵩamino and q is 0, 1, or 2;
provided that the following substituents as a group are not simultaneously allowed:
Ri is methyl;
R₂ is methyl;
R₃ is methyl;
R, is R₅—(CH₂)—;
R₅ is —CHR₆R₇;
Re is hydrogen;
R₇ is t-butyl;
or a pharmaceutically acceptable salt thereof.

2. A compound of claim 1 wherein:
Ri is hydrogen, methyl, fluoro or bromo;
R₂ is hydrogen or methyl;
R3 is hydrogen, methyl, ethyl, acetyl, 2-methoxy ethyl, 2-hydroxy ethyl, oxetan-3-yl, 2-dimethylaminoethyl, N-morpholinoethyl, (1-methylimidazol-4-yl)methyl;
R4 is R₅—(CH₂)—, or 3,3-dimethylcyclobutyl;
R₅ is —CHR₆R₇, or 2,2-dimethylcycloprop-1-yl);
Re is hydrogen or hydroxyl;
R₇ is t-butyl, 1-fluoro-1-methyl-ethyl, 1-cyano-1-methyl-ethyl, 1-methoxy-1-methyl-ethyl, 1-methylcycloprop-1-yl, 1-trifluoromethylcycloprop-1-yl, or 2,2,2-trifluoro-1,1-dimethyl-ethyl;
or a pharmaceutically acceptable salt thereof.

3. A compound of claim 1 wherein:
Ri is hydrogen, methyl or fluoro;
R₂ is hydrogen or methyl;
R₃ is hydrogen, methyl, acetyl, 2-hydroxyethyl, or N-morpholinoethyl;
R₄ is R₅—(CH₂)—, or 3,3-dimethylcyclobutyl;
R₅ is —CHR₆R₇;
Re is hydrogen or hydroxyl;
R₇ is t-butyl, 1-cyano-1-methyl-ethyl, 1-methylcycloprop-1-yl, 1-trifluoromethylcycloprop-1-yl, or 2,2,2-trifluoro-1,1-dimethyl-ethyl;
or a pharmaceutically acceptable salt thereof.

4. A compound of any one of claims 1 to 3 wherein:
Ri is hydrogen;
$R_2$ is methyl;
$R_3$ is methyl;
$R_4$ is $R_5$—$(CH_2)$—;
$R_5$ is —$CHR_6R_7$;
Re is hydrogen;
$R_7$ is t-butyl;
or a pharmaceutically acceptable salt thereof.

5. A compound of any one of claims 1 to 3 wherein:
Ri is methyl;
$R_2$ is methyl;
$R_3$ is hydrogen;
$R_4$ is $R_5$—$(CH_2)$—;
$R_5$ is —$CHR_6R_7$;
Re is hydrogen;
$R_7$ is t-butyl;
or a pharmaceutically acceptable salt thereof.

6. A compound of any one of claims 1 to 3 wherein:
Ri is fluoro;
$R_2$ is methyl;
$R_3$ is methyl;
$R_4$ is $R_5$—$(CH_2)$—;
$R_5$ is —$CHR_6R_7$;
Re is hydrogen;
$R_7$ is t-butyl;
or a pharmaceutically acceptable salt thereof.

7. A compound of any one of claims 1 to 3 wherein: Ri is methyl;
$R_2$ is hydrogen;
$R_3$ is methyl;
$R_4$ is $R_5$—$(CH_2)$—;
$R_5$ is —$CHR_6R_7$;
Re is hydrogen;
$R_7$ is t-butyl;
or a pharmaceutically acceptable salt thereof.

8. A compound of any one of claims 1 to 3 wherein: Ri is hydrogen, methyl, or fluoro;
$R_2$ is methyl;
$R_3$ is methyl;
$R_4$ is $R_5$—$(CH_2)$—;
$R_5$ is —$CHR_6R_7$;
Re is hydrogen;
$R_7$ is 1-cyano-1-methyl-ethyl;
or a pharmaceutically acceptable salt thereof.

9. A compound of any one of claims 1 to 3 wherein:
Ri is hydrogen, methyl, or fluoro;
$R_2$ is methyl;
R3 is methyl;
$R_4$ is 3,3-dimethylcyclobutyl;
or a pharmaceutically acceptable salt thereof.

10. A compound of any one of claims 1 to 3 wherein: Ri is hydrogen, methyl, or fluoro;
$R_2$ is methyl;
$R_3$ is methyl;
$R_4$ is $R_5$—$(CH_2)$—;
$R_5$ is —$CHR_6R_7$;
Re is hydrogen;
$R_7$ is 1-methylcycloprop-1-yl;
or a pharmaceutically acceptable salt thereof.

11. A compound of any one of claims 1 to 3 wherein: Ri is hydrogen, methyl, or fluoro;
$R_2$ is methyl;
$R_3$ is methyl;
$R_4$ is $R_5$—$(CH_2)$—;
$R_5$ is —$CHR_6R_7$;
Re is hydrogen;
$R_7$ is 1-trifluoromethylcycloprop-1-yl;
or a pharmaceutically acceptable salt thereof.

12. A compound of any one of claims 1 to 3 wherein:
Ri is hydrogen, methyl, or fluoro;
$R_2$ is methyl;
$R_3$ is methyl;
$R_4$ is $R_5$—$(CH_2)$—;
$R_5$ is —$CHR_6R_7$;
Re is hydrogen;
$R_7$ is 2,2,2-trifluoro-1,1-dimethyl-ethyl;
or a pharmaceutically acceptable salt thereof.

13. A compound of any one of claims 1 to 3 wherein:
Ri is hydrogen, methyl, or fluoro;
$R_2$ is methyl;
$R_3$ is 2-hydroxyethyl;
R4 is $R_5$—$(CH_2)$—;
$R_5$ is —$CHR_6R_7$;
Re is hydrogen;
$R_7$ is t-butyl;
or a pharmaceutically acceptable salt thereof.

14. A compound of any one of claims 1 to 3 wherein:
Ri is hydrogen, methyl, or fluoro;
$R_2$ is methyl;
R3 is methyl;
$R_4$ is $R_5$—$(CH_2)$—;
$R_5$ is —$CHR_6R_7$;
Re is hydroxyl;
$R_7$ is t-butyl;
or a pharmaceutically acceptable salt thereof.

15. A pharmaceutical composition comprising a compound of claim 1, or a pharmaceutically acceptable salt thereof, in association with a pharmaceutically acceptable carrier.

16. A method of treating a cancer which is thyroid cancer, ovarian cancer, melanoma, AML or colorectal cancer in a patient comprising administering to a patient in need thereof a therapeutically effective amount of a compound of claim 1, or a pharmaceutically acceptable salt thereof.

17. A method of treating melanoma in a patient comprising administering to a patient in need thereof a therapeutically effective amount of a compound of claim 1, or a pharmaceutically acceptable salt thereof.

* * * * *